United States Patent
Magliery et al.

(10) Patent No.: US 11,787,872 B2
(45) Date of Patent: *Oct. 17, 2023

(54) METHODS AND COMPOSITIONS RELATED TO ANTIBODY FRAGMENTS THAT BIND TO TUMOR-ASSOCIATED GLYCOPROTEIN 72 (TAG-72)

(71) Applicant: OHIO STATE INNOVATION FOUNDATION, Columbus, OH (US)

(72) Inventors: Thomas J. Magliery, Columbus, OH (US); Brandon J. Sullivan, Gahanna, OH (US); Nicholas E. Long, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/694,052

(22) Filed: Nov. 25, 2019

(65) Prior Publication Data
US 2020/0255538 A1    Aug. 13, 2020

Related U.S. Application Data

(63) Continuation of application No. 15/328,222, filed as application No. PCT/US2015/041809 on Jul. 23, 2015, now Pat. No. 10,487,151.

(60) Provisional application No. 62/028,003, filed on Jul. 23, 2014.

(51) Int. Cl.
| | |
|---|---|
| *C07K 16/30* | (2006.01) |
| *A61K 51/10* | (2006.01) |
| *A61K 39/395* | (2006.01) |
| *G01N 33/574* | (2006.01) |
| *A61K 47/60* | (2017.01) |
| *A61K 39/00* | (2006.01) |

(52) U.S. Cl.
CPC .... *C07K 16/3092* (2013.01); *A61K 39/39558* (2013.01); *A61K 39/39591* (2013.01); *A61K 47/60* (2017.08); *A61K 51/1045* (2013.01); *A61K 51/1093* (2013.01); *G01N 33/57492* (2013.01); *A61K 2039/505* (2013.01); *C07K 2317/14* (2013.01); *C07K 2317/24* (2013.01); *C07K 2317/622* (2013.01); *C07K 2317/76* (2013.01); *C07K 2317/92* (2013.01); *C07K 2317/94* (2013.01); *G01N 2333/4728* (2013.01)

(58) Field of Classification Search
CPC .............. G01N 33/563; G01N 33/574; G01N 33/57492; G01N 33/577; G01N 33/58; C07K 16/3092; C07K 2317/24; C07K 2317/622; A61K 39/39558; A61K 2039/505
See application file for complete search history.

(56) References Cited

U.S. PATENT DOCUMENTS

| | | | |
|---|---|---|---|
| 9,718,888 B2 * | 8/2017 | Magliery | C12N 5/0693 |
| 10,487,151 B2 * | 11/2019 | Magliery | A61K 39/39591 |
| 10,919,979 B2 * | 2/2021 | Magliery | A61K 51/1045 |
| 2004/0259768 A1 | 12/2004 | Lauermann | |
| 2007/0244032 A1 | 10/2007 | Kim et al. | |
| 2008/0279847 A1 * | 11/2008 | Hong | A61P 35/04 424/133.1 |
| 2009/0136484 A1 * | 5/2009 | Burnie | A61P 31/10 435/69.6 |
| 2010/0113355 A1 * | 5/2010 | Chennamsetty | A61P 29/00 435/320.1 |
| 2010/0183504 A1 | 7/2010 | Chen | |
| 2011/0159525 A1 | 6/2011 | Kashmiri et al. | |
| 2012/0301899 A1 * | 11/2012 | Choo | C07K 16/28 435/7.21 |

FOREIGN PATENT DOCUMENTS

| | | |
|---|---|---|
| WO | 2005/121180 | 12/2005 |
| WO | 2015/013429 | 1/2015 |

OTHER PUBLICATIONS

Yoon et al., Construction, affinity maturation, and biological characterization of an anti-tumor-associated glycoprotein-72 humanized antibody, J Biol Chem 2006, 281, 6985-6992.*
Gero et al., CA 72-4 Radioimmunoassay for the Detection of the TAG-72 Carcinoma-Associated Antigen in Serum of Patients, J Clin Lab Anal, 1989, 3:360-369.*
Paul, Fundamental Immunology, 3rd Edition, 1993, pp. 292-295.*
Rudikoff et al., Proc. Natl. Acad. Sci. USA, 1982, 79(6):1979-1983.*
Colman, Research in Immunology, 1994, 145:33-36.*
Bendig, Methods: A Companion to Methods in Enzymology, 1995; 8:83-93.*
Khantasup et al., Monoclonal Antibodies in Immunodiagnosis and Immunotherapy, 2015, 34(6): 404-417.*
European Patent Office. Extended European Search Report. European Application No. 20194931.0, dated Jan. 27, 2021. 7 pages.
Communication Pursuant to Article 94(3) EPC, issued for Application No. 15824172.9, dated Apr. 16, 2019.
Bailey, G. S. (1996) The Iodogen Method for Radiolabeling Protein, Humana Press Inc., Totowa, NJ, 2 pages.
Bird, R. E., Hardman, K. D., Jacobson, J. W., Johnson, S., Kaufman, B. M., Lee, S. M., Lee, T., Pope, S. H., Riordan, G. S. & Whitlow, M. (1988). Single-chain antigen-binding proteins. Science 242, 423-6. Abstract.
Bork, P., Holm, L. & Sander, C. (1994). The immunoglobulin fold. Structural classification, sequence patterns and common core. J Mol Biol 242, 309-20.
Chen, C., Constantinou, A., Deonarain, M. (2011) Modulating antibody pharmacokinetics using hydrophilic polymers. Exper Opin Drug Deliv 8, 1221-36.

(Continued)

*Primary Examiner* — Hong Sang
(74) *Attorney, Agent, or Firm* — Meunier Carlin & Curfman LLC

(57) ABSTRACT

Disclosed herein are methods and compositions related to antibody fragments which specifically bind sialyl-Tn epitope of tumor-associated glycoprotein 72 (TAG-72).

10 Claims, 27 Drawing Sheets

Specification includes a Sequence Listing.

(56) References Cited

OTHER PUBLICATIONS

Cheng, Kenneth T. (2007) 99mTC-Hydrazinonicotinamide-anti-TAG-72 CC49 tetravalent single-chain Fv monoclonal antibody. Molecular Imaging and Contrast Agent Database. Jun. 19, 2007, 1-5.

Colcher, D., Minelli, M. F., Roselli, M., Muraro, R., Simpson-Milenic, D. & Schlom, J. (1988). Radioimmunolocalization of human carcinoma xenografts with B72.3 second generation monoclonal antibodies. Cancer Res 48, 4597-603.

Colcher, D., Pavlinkova, G., Beresford, G., Booth, B. J. & Batra, S. K. (1999). Single-chain antibodies in pancreatic cancer. Ann N Y Acad Sci 880, 263-80.

Denzin, L. K., Whitlow, M. & Voss, E. W., Jr. (1991). Single-chain site-specific mutations of fluorescein-amino acid contact residues in high affinity monoclonal antibody Apr. 4, 2020. J Biol Chem 266, 14095-103.

Divgi, C. R., Scott, A. M., Dantis, L., Capitelli, P., Siler, K., Hilton, S., Finn, R. D., Kemeny, N., Kelsen, D., Kostakoglu, L. & et al. (1995). Phase I radioimmunotherapy trial with iodine-131-CC49 in metastatic colon carcinoma. J Nucl Med 36, 586-92.

Durani, V., Sullivan, B.J., Magliery, T.J. (2012) Simplifying protein expression with ligation-free, traceless and tag-switching plasmids. Protein Expr Purif 85, 9-17.

Goel, A., Colcher, D., Baranowska-Kortylewicz, et al. (2000) Genetically engineered tetravalent single-chain Fv of the pancarcinoma monoclonal antibody CC49: Improved biodistribution and potential for therapeutic application. Cancer Res 60, 6964-71.

International Search Report and Written Opinion of the International Searching Authority, Application No. PCT/US2015/041809, dated Jan. 12, 2016, 18 pages.

International Preliminary Report on Patentability, Application No. PCT/US2015/041809, dated Feb. 2, 2017.

Jemal, A., Bray, F., Center, M. M., Ferlay, J., Ward, E. & Forman, D. (2011). Global cancer statistics. CA Cancer J Clin 61, 69-90.

Julien, S., Videira, P. A., & Delannoy, P. (2012). Sialyl-tn in cancer: (how) did we miss the target?. Biomolecules, 2(4), 435-466.

Kashmiri, S. V., Shu, L., Padlan, E. A., Milenic, D. E., Schlom, J. & Hand, P. H. (1995). Generation, characterization, and in vivo studies of humanized anticarcinoma antibody CC49. Hybridoma 14, 461-73.

Kjeldsen, T., Clausen, H., Hirohashi, S., Ogawa, T., Iijima, H. & Hakomori, S. (1988). Preparation and characterization of monoclonal antibodies directed to the tumor-associated O-linked sialosyl-2—6 alpha-N-acetylgalactosaminyl (sialosyl-Tn) epitope. Cancer Res 48, 2214-20.

Kortt, A.A., Dolezal, O., Power, B.E., Hudson, P.J. (2001). Dimeric and trimeric antibodies: high avidity scFv for cancer targeting. Biomol Eng 18, 95-108.

Lavinder, J. J., Hari, S. B., Sullivan, B. J. & Magliery, T. J. (2009). High-throughput thermal scanning: a general, rapid dye-binding thermal shift screen for protein engineering. J Am Chem Soc 131, 3794-5.

Maddalena, M. E., Fox, J., Chen, J., Feng, W., Cagnolini, A., Linder, K. E., Tweedle, M. F., Nunn, A. D., and Lantry, L. E. (2009) 177Lu-AMBA biodistribution, radiotherapeutic efficacy, imaging, and autoradiography in prostate cancer models with low GRP-R expression. Journal of nuclear medicine : official publication, Society of Nuclear Medicine 50, 2017-24.

Miroux, B., Walker, J.E. (1996) Over-production of proteins in *Escherichia coli*: mutant hosts that allow synthesis of some membrane proteins and globular proteins at high levels. J Mol Biol 260, 289-98.

Muraro, R., Kuroki, M., Wunderlich, D., Poole, D. J., Colcher, D., Thor, A., Greiner, J. W., Simpson, J. F., Molinolo, A., Noguchi, P. & et al. (1988). Generation and characterization of B72.3 second generation monoclonal antibodies reactive with the tumor-associated glycoprotein 7 2 antigen. Cancer Res 48, 4588-96.

Paus, E. B., O.; Nustad,K. (1982) Radioiodination of proteins with the Iodogen method, International Atomic Energy Agency, Vienna. In Radioimmunoassay and related procedures in medicine 1982.

Pavlinkova, G., Beresford, G. W., Booth, B. J., Batra, S. K. & Colcher, D. (1999). Pharmacokinetics and biodistribution of engineered single-chain antibody constructs of MAb CC49 in colon carcinoma xenografts. J Nucl Med 40, 1536-46.

Pini, A. & Bracci, L. (2000). Phage display of antibody fragments. Curr Protein Pept Sci 1, 155-69. Abstract.

Prachayasittikul, V., Isarankura-Na-Ayudhya, C., Tantimongcolwat, T., Nantasenamat, C. & Galla, H. J. (2007). EDTA-induced membrane fluidization and destabilization: biophysical studies on artificial lipid membranes. Acta Biochim Biophys Sin (Shanghai) 39, 901-13.

Sandhu, J. S. (1992). Protein engineering of antibodies. Crit Rev Biotechnol 12, 437-62. Abstarct.

Senisterra, G. A. & Finerty, P. J., Jr. (2009). High throughput methods of assessing protein stability and aggregation. Mol Biosyst 5, 217-23.

Sun, D., Bloomston, M., Hinkle, G., Al-Saif, O. H., Hall, N. C., Povoski, S. P., Arnold, M. W. & Martin, E. W., Jr. (2007). Radioimmunoguided surgery (RIGS), PET/CT image-guided surgery, and fluorescence image-guided surgery: past, present, and future. J Surg Oncol 96, 297-308.

Thor, A., Ohuchi, N., Szpak, C. A., Johnston, W. W. & Schlom, J. (1986). Distribution of oncofetal antigen tumor-associated glycoprotein-72 defined by monoclonal antibody B72.3. Cancer Res 46, 3118-24.

Thor, A., Viglione, M. J., Muraro, R., Ohuchi, N., Schlom, J. & Gorstein, F. (1987). Monoclonal antibody B72.3 reactivity with human endometrium: a study of normal and malignant tissues. Int J Gynecol Pathol 6, 235-47. Abstract.

Veronese, F.M., Mero, A. (2008) The impact of PEGylation on biological therapies. BioDrugs 22, 315-29.

Wedeking, P., and Tweedle, M. (1988) Comparison of the Biodistribution of Gd-153-Labeled Gd(Dtpa)2-, Gd(Dota)-, and Gd(Acetate)N in Mice. Nuclear medicine and biology 15, 395-402.

Yang, K., Basu, A., Wang, M., Chintala, R., Hsieh, M. C., Liu, S., Hua, J., Zhang, Z., Zhou, J., Li, M., Phyu, H., Petti, G., Mendez, M., Janjua, H., Peng, P., Longley, C., Borowski, V., Mehlig, M. & Filpula, D. (2003). Tailoring structure-function and pharmacokinetic properties of single-chain Fv proteins by site-specific PEGylation. Protein Eng 16, 761-70.

Yokota, T., Milenic, D. E., Whitlow, M. & Schlom, J. (1992). Rapid tumor penetration of a single-chain Fv and comparison with other immunoglobulin forms. Cancer Res 52, 3402-8.

Yoon, S. O., Lee, T. S., Kim, S. J., Jang, M. H., Kang, Y. J., Park, J. H., Kim, K. S., Lee, H. S., Ryu, C. J., Gonzales, N. R., Kashmiri, S. V., Lim, S. M., Choi, C. W. & Hong, H. J. (2006). Construction, affinity maturation, and biological characterization of an anti-tumor-associated glycoprotein-72 humanized antibody. J Biol Chem 281, 6985-92.

Ding, Haiming, et al. "Site specific discrete PEGylation of 124I-labeled mCC49 Fab' fragments improves tumor microPET/CT imaging in mice." Bioconjugate chemistry 24.11 (2013): 1945-1954.

Extended European Search Report and European Search Opinion, issued by the European Patent Office in Application No. EP 15824172.9 dated Jan. 3, 2018, 10 pages.

Rogers, Buck E., et al. "Intraperitoneal radioimmunotherapy with a humanized anti-TAG-72 (CC49) antibody with a deleted CH2 region." Cancer biotherapy & radiopharmaceuticals 20.5 (2005): 502-513.

Long, Nicholas E., et al. "Linker engineering in anti-TAG-72 antibody fragments optimizes biophysical properties, serum half-life, and high-specificity tumor imaging." Journal of Biological Chemistry (2018: 293(23): 9030-9040.

European Patent Office. Communication pursuant to Article 94(3) EPC. Application No. 15824172.9, dated Dec. 6, 2018. 6 pages.

Examination report No. 1 for Australian patent Application No. 2015292498, dated Mar. 27, 2020.

European Patent Office. Communication Pursuant to Article 94(3) EPC. Issued in European Application No. 20194931.0 dated Mar. 1, 2022. 6 pages.

(56) References Cited

OTHER PUBLICATIONS

Canadian Intellectual Property Office. Office Action issued in Canadian Patent Application No. 2,956,161 dated Oct. 12, 2022 4 pages.
European Patent Office. Communication pursuant to Article 94(3) EPC. Issued in European Patent Application No. 20194931.0, dated Mar. 10, 2023. 5 pages.

* cited by examiner

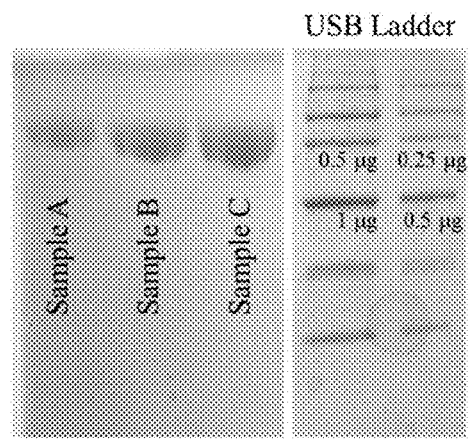
FIG.27
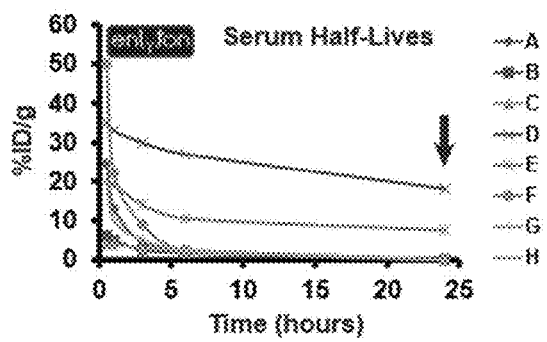 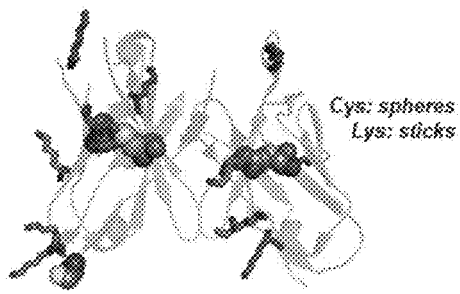
FIG.28
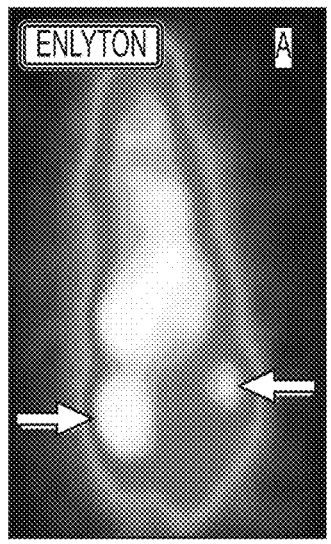 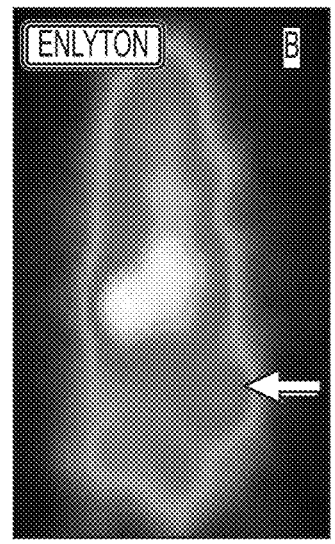 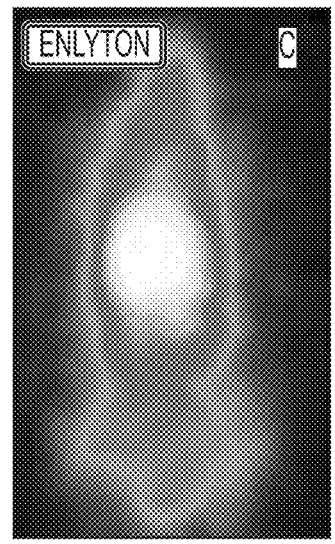
*FIG. 29A*  *FIG. 29B*  *FIG. 29C*

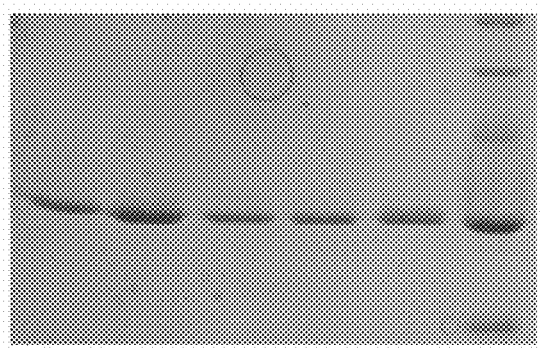
FIG.33
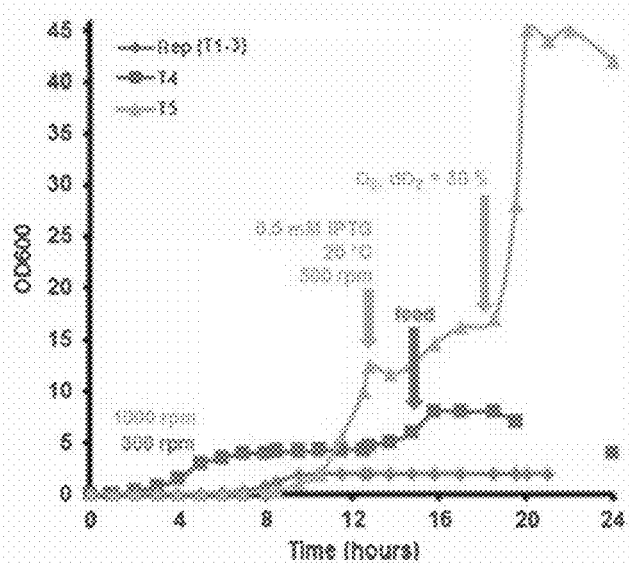
FIG.34
0 hrs 0.5 hrs 1 hrs 1.5 hrs 2 hrs 3 hrs 4 hrs 6 hrs 8 hrs
FIG.35

| | average %ID/g | sd |
|---|---|---|
| blood | 0.44% | 0.04% |
| lungs | 0.91% | 0.37% |
| heart | 0.17% | 0.03% |
| liver | 0.23% | 0.03% |
| spleen | 0.41% | 0.01% |
| pancreas | 0.13% | 0.04% |
| GI | 0.29% | 0.07% |
| Kidneys | 0.54% | 0.20% |
| muscle | 0.17% | 0.11% |
| skin | 0.19% | 0.04% |
| tail | 1.58% | 0.98% |
| carcass | 0.66% | 0.16% |

METHODS AND COMPOSITIONS RELATED TO ANTIBODY FRAGMENTS THAT BIND TO TUMOR-ASSOCIATED GLYCOPROTEIN 72 (TAG-72)

CROSS REFERENCE TO RELATED APPLICATIONS

This application is a continuation application of U.S. application Ser. No. 15/328,222, filed Jan. 23, 2017, now U.S. Pat. No. 10,487,151, issued Nov. 26, 2019, which is a National Phase Application of PCT/US2015/041809, filed Jul. 23, 2015, which claims the benefit of U.S. Provisional Patent Application Ser. No. 62/028,003, filed Jul. 23, 2014, the disclosure of which is expressly incorporated herein by reference.

SEQUENCE LISTING

A substitute Sequence Listing was filed in electronic format on Nov. 25, 2019. The Sequence Listing was provided as a file entitled 10336-101US2_2010_11_25 AS FILED Substitute Sequence Listing, created Nov. 25, 2019 which is 87.3 Kb in size. Tue information in the electronic format of the Sequence Listing is incorporated herein by reference in its entirety.

FIELD OF THE DISCLOSURE

This disclosure relates generally to antibodies, more particularly, to antibodies that are suitable for the treatment of cancer.

BACKGROUND

Greater than 10% of all deaths are caused by cancer; therefore, it is imperative that scientific research improves and innovates the state-of-the-art in prevention, diagnosis, imaging, therapeutics, and surgery (Jemal 2011). Traditional cancer imaging techniques rely on computed tomography (CT) and positron emission tomography (PET). Both methods suffer from poor resolution and weak signal-to-noise ratios. Radioimmunoguided detection and surgery (RIGS) is a powerful modality for accurately mapping the surfaces of cancerous tissue, but the current catalog of cancer-binding antibodies are not ideal for these applications (Sun 2007).

Several generations of monoclonal antibodies have been developed against the sialyl-Tn epitope. The first two, B72.3 (Thor 1986 and Thor 1987) and CC49 (Muraro 1988; Colcher 1988), entered clinical trials for radioimmunoguided surgery (RIGS), but a significant fraction of patients developed human anti-mouse antibodies (HAMA) (Dvigi 1995). In response, a humanized variant of CC49 was constructed (AKA) (Yoon 2006; Kashmiri 1995). None of the 21 patients experience HAMA when the procedure was performed with AKA, but the third generation antibody lost more than two-fold of its binding affinity. In 2008, Yoon et al. constructed a Fab library at CDR3 of AKA (Yoon 2006). This study yielded a Fab with improved binding that was later converted to a full-length IgG named 3E8.

The latest generation of sialyl-Tn IgGs (tumor-associated antigens) are nonimmunogenic and bind the sialyl-Tn epitope with remarkable affinity. However, in order to satisfy all the requirements for imaging, these full-length antibodies require reduction to the smaller scFv scaffold. This remaining step is nontrivial, which likely describes why these imaging agents are not common place in hospitals. The variable domains are stabilized by the constant domains which are void in the truncated scFv. Independently, the VH and VL domains are only weakly associated by noncovalent interactions (and possibly disulfide bonding), thus an amino acid linker is required to assemble the full antigen binding site. Often, these engineered proteins suffer from loss of affinity, heterogeneity in quaternary structure, and diminished stability. What is needed in the art is a dramatically stabilized 3E8 antibody fragment, such as those disclosed herein.

SUMMARY

Disclosed herein is an antibody fragment which specifically bind tumor-associated glycoprotein 72 (TAG-72). Disclosed herein are antibody fragments which bind the sialyl-Tn epitope of TAG-72. Examples include those found in SEQ ID NOS SEQ ID NO: 13, 15, 17, 19, 21, 23, 25, 27, 29, 31, 33, 35, 37, 39, 41, 43, or 45. The antibody fragment can comprise a heavy chain variable region comprising SEQ ID NO: 10, and a light chain variable region comprising SEQ ID NO: 11.

Also disclosed are nucleic acid sequences corresponding to the antibody fragments disclosed herein which specifically bind TAG-72. For example, disclosed are nucleic acid sequences SEQ ID NOS: 12, 14, 16, 18, 20, 22, 24, 26, 28, 30, 32, 34, 36, 38, 40, 42, and 44.

Disclosed are compositions comprising the antibody fragments disclosed herein which specifically bind TAG-72 and a pharmaceutically acceptable carrier. Disclosed are compositions suitable for the treatment of cancer comprising a therapeutically effective amount of an antibody fragment which specifically binds TAG-72.

Further disclosed is a composition suitable for the in vivo or in vitro detection of cancer comprising a diagnostically effective amount of an antibody fragment which specifically binds TAG-72.

Disclosed is a method for in vivo treatment of a mammal having a TAG-72-expressing cancer comprising a step of administering to the mammal a therapeutically effective amount of a composition comprising an antibody fragment which specifically binds TAG-72.

Disclosed is a method for in vitro immunodetection of TAG-72-expressing cancer cells comprising a step of contacting the cancer cells with a composition suitable in vitro detection of cancer comprising a diagnostically effective amount of an antibody fragment which specifically binds TAG-72.

Also disclosed is a method for in vivo immunodetection of TAG-72-expressing cancer cells comprising a step of contacting the cancer cells with a composition suitable for in vitro detection of cancer comprising a diagnostically effective amount of an antibody fragment of TAG-72.

Disclosed herein is a method of in vivo treatment of cancer comprising the steps of: (a) intravenously administering a radionuclide-labeled antibody fragment which specifically binds TAG-72; (b) detecting tumor cells using a radionuclide activity probe; and (c) removing the detected tumor cells by surgical excision.

Disclosed herein are kits comprising an antibody fragment which specifically binds TAG-72 and instructions for its use.

Disclosed are method of making an antibody fragment which specifically binds TAG-72, comprising: (a) culturing an isolated cell under conditions such that said antibody fragment is expressed; and (b) recovering said antibody fragment from the cell.

Also disclosed are methods of treating cancer comprising administering to a subject in need thereof a composition comprising an antibody fragment which specifically binds TAG-72, wherein the effector moiety is a chemotherapeutic agent.

Disclosed is a method for prognosing recurrence of cancer in a subject previously treated for the cancer, the method comprising: (a) isolating a biological sample comprising cells from a subject with a cancer; (b) contacting the biological sample with a composition comprising an antibody fragment under conditions sufficient for the composition to bind to an epitope present on a tumor and/or a cancer cell, if present, in the biological sample; and (c) identifying in the biological sample one or more cells that bind to the composition comprising an antibody fragment which specifically binds TAG-72, whereby recurrence of a cancer is prognosed in the subject.

DESCRIPTION OF DRAWINGS

FIG. 22A: Model of 3E8.scFv—The complementary determining regions are the loops responsible for binding the antigen. The C-terminal cysteine is shown opposite the binding site. FIG. 22B: PEGylation increases the hydrodynamic radius of proteins, can reduce immunogenicity, decrease aggregation, and protect the antibody fragment from serum proteases.

FIG. 27 shows 3E8cys.scFv was conjugated with a linear 30 kD PEG. Three antibody fragment aliquots were PEGylated and purified. Sample C provided the highest yield and purity, therefore, it was used for tumor imaging.

FIG. 28 shows the serum half-lives can be tuned with polyethylene glycol (PEG) conjugation. PEGylated antibody fragments are shown using lysines (NHS-ester chemistry) and cysteines (maleimide chemistry).

FIGS. 29A-C show proof-of-concept surgical resection with intraoperative imaging via the $^{123}$I-labeled antibody fragment. A. Image taken prior to surgery (tumors arrowed). B. A second image is taken to assess the surgical procedure. Note residual tumor remains on the right flank. C. Image taken after complete removal of cancerous tissue.

FIG. 33 shows two T7 expression strains tested, BLR (DE3) and HMS174(DE3). BLR(DE3) is a BL21(DE3) derivative that is recA-, resulting in improved genome and plasmid stability. HMS174(DE3) is a K12 bacteria that also contains a mutations to the recA gene.

FIG. 34 shows bioreactor optimization conditions. The two primary conditions that were optimized were dissolved oxygen percentage and source, as well as agitation speed. The standard Rushton impeller was used, but did not include baffles. Initially, baffles were used and set the agitation speed to 100 rpm based on previous experience with shake flasks—baffled flasks at 225 rpm led to cellular lysis.

FIG. 35 shows the role of induction point and the expression time course for $3E8.G^4S$. The sample was prepared identically as before, but the culture was allowed to reach OD600=45, before added 0.5 mM IPTG, shifting the temperature to 20° C., reducing agitation to 500 rpm, and adding supplemental oxygen to maintain dO2 at 30%. This culture maintained an optical density of 45-50 for nearly 24 hours post induction when the experiment was terminated. At 0.5, 1, 1.5, 2, 3, 4, 6, and 8 hours 50 mL of culture were harvested and snap frozen for further studies. Each cell pellet was resuspended to an OD600=46, and 10 mL of normalized cultures were purified in parallel.

(FIG. 38). Next, the sample is eluted with Protein L elution buffer (100 mM glycine pH 3). The SDS-PAGE gel shown to the right shows the flowthrough, wash, and elution of the hexahistidine tagged $3E8.G^4S$. Note that the desired antibody fragment is arrowed and that several proteolytic products or copurifying contaminates are bound and eluted from the Protein L column. These bands are able to be removed by ion exchange chromatography.

DETAILED DESCRIPTION

Figure 1:
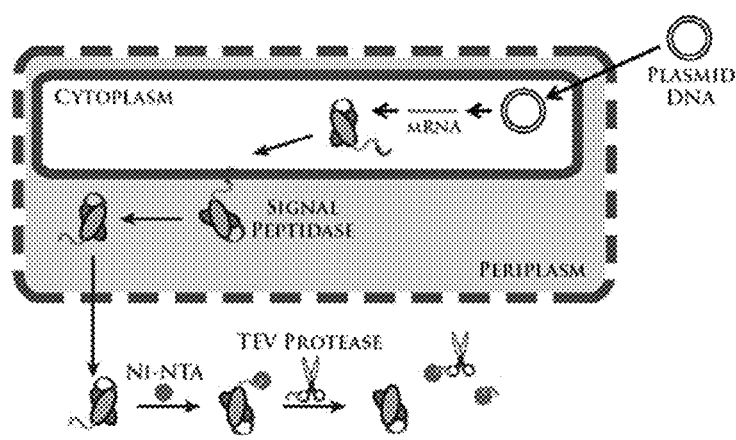
FIG. 1 shows a schematic describing the production, export and purification of scFv. Signal peptide with TEV cleavage site shown. Note that the 6×His tag and TEV protease are removed by a second Ni-NTA agarose column.
Figure 2:
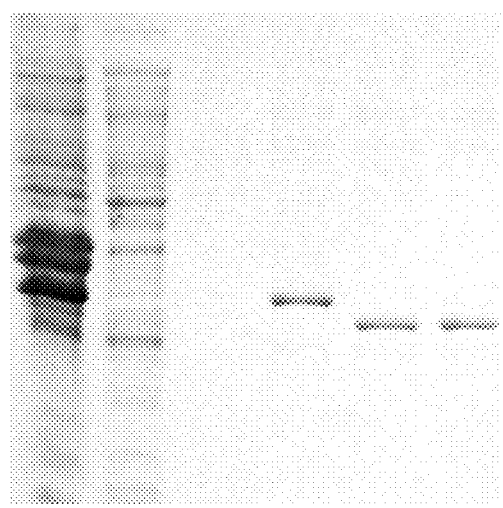
FIG. 2 shows sample purification of 3E8.scFv from pCOLD IV. Lane 1: Sphereoplasts, Lane 2: Periplasmic fraction after Ni-NTA binding, Lane 3: Wash, Lane 4: Eluted 6×His-TEV-3E8.scFv, Lane 5: 3E8.scFv after TEV protease cleavage to remove 6×His-tag, Lane 6: Ni-NTA purified protein after removal of TEV protease and 6×His-tag.

The materials, compositions, and methods described herein can be understood more readily by reference to the following detailed descriptions of specific aspects of the disclosed subject matter and the Examples and Figure included herein.

Before the present materials, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Definitions

Unless defined otherwise, all technical and scientific terms used herein have the same meaning as commonly understood by one of ordinary skill in the art. Methods and materials similar or equivalent to those described herein can be used in the practice or testing of the present disclosure. In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "an antibody" includes mixtures of two or more such antibodies; reference to "the composition" includes mixtures of two or more such compositions, and the like.

"Optional" or "optionally" means that the subsequently described event or circumstance can or cannot occur, and that the description includes instances where the event or circumstance occurs and instances where it does not.

Unless otherwise indicated, all numbers expressing quantities of ingredients, reaction conditions, and so forth used in the specification and claims are to be understood as being modified in all instances by the term "about". The term "about", as used herein when referring to a measurable value such as an amount of mass, weight, time, volume, concentration, or percentage, is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods and/or employ the disclosed compositions. Accordingly, unless indicated to the contrary, the numerical parameters set forth in this specification and attached claims are approximations that can vary depending upon the desired properties sought to be obtained by the presently disclosed subject matter.

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D.

With respect to the terms "comprising", "consisting of, and "consisting essentially of, where one of these three terms is used herein, the presently disclosed and claimed subject matter can include the use of either of the other two terms. For example, in some embodiments, the presently disclosed subject matter relates to compositions comprising antibodies. It would be understood by one of ordinary skill in the art after review of the instant disclosure that the presently disclosed subject matter thus encompasses compositions that consist essentially of the antibodies of the presently disclosed subject matter, as well as compositions that consist of the antibodies of the presently disclosed subject matter.

The term "subject" as used herein refers to a member of any invertebrate or vertebrate species. Accordingly, the term "subject" is intended to encompass in some embodiments any member of the Kingdom Animalia including, but not limited to the phylum Chordata (e.g., members of Classes Osteichythyes (bony fish), Amphibia (amphibians), Reptilia (reptiles), Ayes (birds), and Mammalia (mammals), and all Orders and Families encompassed therein.

The compositions and methods of the presently disclosed subject matter are particularly useful for warm-blooded vertebrates. Thus, in some embodiments the presently disclosed subject matter concerns mammals and birds. More particularly provided are compositions and methods derived from and/or for use in mammals such as humans and other primates, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), rodents (such as mice, rats, and rabbits), marsupials, and horses. Also provided is the use of the disclosed methods and compositions on birds, including those kinds of birds that are endangered, kept in zoos, as well as fowl, and more particularly domesticated fowl, e.g., poultry, such as turkeys, chickens, ducks, geese, guinea fowl, and the like, as they are also of economic importance to humans. Thus, also provided is the use of the disclosed methods and compositions on livestock, including but not limited to domesticated swine (pigs and hogs), ruminants, horses, poultry, and the like.

Similarly, all genes, gene names, and gene products disclosed herein are intended to correspond to homologs and/or orthologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes presented in GENBANK® Accession Nos: AAA60019 and NP_004976, the human amino acid sequences disclosed are intended to encompass homologous genes and gene products from other animals including, but not limited to other mammals, fish, amphibians, reptiles, and birds. Also encompassed are any and all nucleotide sequences that encode the disclosed amino acid sequences, including but not limited to those disclosed in the corresponding GENBANK® entries (i.e., J05582.1 and NM_004985, respectively).

The terms "cancer" and "tumor" are used interchangeably herein and can refer to both primary and metastasized solid tumors and carcinomas of any tissue in a subject, including but not limited to breast; colon; rectum; lung; oropharynx; hypopharynx; esophagus; stomach; pancreas; liver; gallbladder; bile ducts; small intestine; urinary tract including kidney, bladder, and urothelium; female genital tract including cervix, uterus, ovaries (e.g., choriocarcinoma and gestational trophoblastic disease); male genital tract including prostate, seminal vesicles, testes and germ cell tumors; endocrine glands including thyroid, adrenal, and pituitary; skin (e.g., hemangiomas and melanomas), bone or soft tissues; blood vessels (e.g., Kaposi's sarcoma); brain, nerves, eyes, and meninges (e.g., astrocytomas, gliomas, glioblastomas, retinoblastomas, neuromas, neuroblastomas, Schwannomas and meningiomas). As used herein, the terms "cancer and "tumor" are also intended to refer to multicellular tumors as well as individual neoplastic or preneoplastic cells. In some embodiments, a cancer or a tumor comprises a cancer or tumor of an epithelial tissue such as, but not limited to a carcinoma. In some embodiments, a tumor is an adenocarcinoma, which in some embodiments is an adenocarcinoma of the pancreas, breast, ovary, colon, or rectum, and/or a metastatic cell derived therefrom.

As used herein in the context of molecules, the term "effector" refers to any molecule or combination of molecules whose activity it is desired to deliver/into and/or localize at a cell. Effectors include, but are not limited to labels, cytotoxins, enzymes, growth factors, transcription factors, drugs, etc.

As used herein in the context of cells of the immune system, the term "effector" refers to an immune system cell that can be induced to perform a specific function associated with an immune response to a stimulus. Exemplary effector cells include, but are not limited to natural killer (NK) cells and cytotoxic T cells (Tc cells).

As used herein, the term "expression vector" refers to a DNA sequence capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The construct comprising the nucleotide sequence of interest can be chimeric. The construct can also be one that is naturally occurring but has been obtained in a recombinant form useful for heterologous expression.

As used herein, the term "hybridoma" refers to a cell or cell line that is produced in the laboratory from the fusion of an antibody-producing lymphocyte and a non-antibody-producing cancer cell, usually a myeloma or lymphoma cell. As would be known to those of one of ordinary skill in the art, a hybridoma can proliferate and produce a continuous supply of a specific monoclonal antibody. Methods for generating hybridomas are known in the art (see e.g., Harlow & Lane, 1988).

As used herein, the terms "operatively linked" and "operably linked" refer to transcriptional regulatory elements (such as, but not limited to promoter sequences, transcription terminator sequences, etc.) that are connected to a nucleotide sequence (for example, a coding sequence or open reading frame) in such a way that the transcription of the nucleotide sequence is controlled and regulated by that transcriptional regulatory element. Similarly, a nucleotide sequence is said to be under the "transcriptional control" of a promoter to which it is operably linked. Techniques for operatively linking a promoter region to a nucleotide sequence are known in the art.

As used herein, the term "prodrug" refers to an analog and/or a precursor of a drug (e.g., a cytotoxic agent) that substantially lacks the biological activity of the drug (e.g., a cytotoxic activity) until subjected to an activation step. Activation steps can include enzymatic cleavage, chemical activation steps such as exposure to a reductant, and/or physical activation steps such as photolysis. In some embodiments, activation occurs in vivo within the body of a subject, As used herein, the terms "antibody" and "antibodies" refer to proteins comprising one or more polypeptides substantially encoded by immunoglobulin genes or fragments of immunoglobulin genes Immunoglobulin genes typically include the kappa (κ), lambda (i), alpha (α), gamma (γ), delta (δ), epsilon (ε), and mu (μ) constant region genes, as well as myriad immunoglobulin variable region genes. Light chains are classified as either κ or λ. In mammals, heavy chains are classified as γ, μ, α, δ, or ε, which in turn define the immunoglobulin classes, IgG, IgM, IgA, IgD, and IgE, respectively. Other species have other light and heavy chain genes (e.g., certain avians produced what is referred to as IgY, which is an immunoglobulin type that hens deposit in the yolks of their eggs), which are similarly encompassed by the presently disclosed subject matter. In some embodiments, the term "antibody" refers to an antibody that binds specifically to an epitope that is present on a tumor antigen.

The term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab'), scFv, Fv, diabody, tribody, tetrabody, Fd fragments, or mixtures thereof. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex.

A typical immunoglobulin (antibody) structural unit is known to comprise a tetramer. Each tetramer is composed of two identical pairs of polypeptide chains, each pair having one "light" chain (average molecular weight of about 25 kiloDalton (kDa)) and one "heavy" chain (average molecular weight of about 50-70 kDa). The two identical pairs of polypeptide chains are held together in dimeric form by disulfide bonds that are present within the heavy chain region. The N-terminus of each chain defines a variable region of about 100 to 110 or more amino acids primarily responsible for antigen recognition (sometimes referred to as the "paratope"). The terms variable light chain (VL) and variable heavy chain (VH) refer to these light and heavy chains, respectively.

Antibodies typically exist as intact immunoglobulins or as a number of well-characterized fragments that can be produced by digestion with various peptidases. For example, digestion of an antibody molecule with papain cleaves the antibody at a position N-terminal to the disulfide bonds. This produces three fragments: two identical "Fab" fragments, which have a light chain and the N-terminus of the heavy chain, and an "Fc" fragment that includes the C-terminus of the heavy chains held together by the disulfide bonds. Pepsin, on the other hand, digests an antibody C-terminal to the disulfide bond in the hinge region to produce a fragment known as the "F(ab)'2" fragment, which is a dimer of the Fab fragments joined by the disulfide bond. The F(ab)'2 fragment can be reduced under mild conditions to break the disulfide linkage in the hinge region, thereby converting the F(ab')2 dimer into two "Fab'" monomers. The Fab' monomer is essentially an Fab fragment with part of the hinge region (see e.g., Paul, 1993, for a more detailed description of other antibody fragments). With respect to these various fragments, Fab, F(ab')2, and Fab' fragments include at least one intact antigen binding domain (paratope), and thus are capable of binding to antigens.

While various antibody fragments are defined in terms of the digestion of an intact antibody, one of skill will appreciate that various of these fragments (including, but not limited to Fab' fragments) can be synthesized de novo either chemically or by utilizing recombinant DNA methodology. Thus, the term "antibody" as used herein also includes antibody fragments produced by the modification of whole antibodies and/or synthesized de novo using recombinant DNA methodologies. In some embodiments, the term "antibody" comprises a fragment that has at least one antigen binding domain (paratope).

Antibodies can be polyclonal or monoclonal. As used herein, the term "polyclonal" refers to antibodies that are present together in a given collection of antibodies and that are derived from different antibody-producing cells (e.g., B cells). Exemplary polyclonal antibodies include, but are not limited to those antibodies that bind to a particular antigen and that are found in the blood of an animal after that animal has produced an immune response against the antigen. However, it is understood that a polyclonal preparation of antibodies can also be prepared artificially by mixing at least non-identical two antibodies. Thus, polyclonal antibodies typically include different antibodies that are directed against (i.e., bind to) the same and/or different epitopes (sometimes referred to as an "antigenic determinant" or just "determinant") of any given antigen.

As used herein, the term "monoclonal" refers to a single antibody species and/or a substantially homogeneous population of a single antibody species. Stated another way, "monoclonal" refers to individual antibodies or populations of individual antibodies in which the antibodies are identical in specificity and affinity except for possible naturally occurring mutations that can be present in minor amounts. Typically, a monoclonal antibody (mAb or moAb) is generated by a single B cell or a progeny cell thereof (although the presently disclosed subject matter also encompasses "monoclonal" antibodies that are produced by molecular biological techniques as described herein). Monoclonal antibodies (mAbs or moAbs) are highly specific, typically being directed against a single antigenic site. Furthermore, in contrast to polyclonal antibody preparations, a given mAb is typically directed against a single epitope on the antigen.

In addition to their specificity, mAbs can be advantageous for some purposes in that they can be synthesized uncontaminated by other antibodies. The modifier "monoclonal" is not to be construed as requiring production of the antibody by any particular method, however. For example, in some embodiments, the mAbs of the presently disclosed subject matter are prepared using the hybridoma methodology first described by Kohler et al., 1975, and in some embodiments are made using recombinant DNA methods in prokaryotic or eukaryotic cells (see e.g., U.S. Pat. No. 4,816,567, the entire contents of which are incorporated herein by reference). mAbs can also be isolated from phage antibody libraries.

The antibodies, fragments, and derivatives of the presently disclosed subject matter can also include chimeric antibodies. As used herein in the context of antibodies, the term "chimeric", and grammatical variants thereof, refers to antibody derivatives that have constant regions derived substantially or exclusively from antibody constant regions from one species and variable regions derived substantially or exclusively from the sequence of the variable region from another species.

The variable region allows an antibody to selectively recognize and specifically bind epitopes on antigens. That is, the VL domain and VH domain, or subsets of the complementarity determining regions (CDRs) within these variable domains, of an antibody combine to form the variable region that defines a three dimensional antigen binding site. This quaternary antibody structure forms the antigen binding site present at the end of each arm of the antibody. More specifically, the antigen binding site is defined by three CDRs on each of the VH and VL chains. In some instances (e.g., certain immunoglobulin molecules derived from camelid species or engineered based on camelid immunoglobulins), a complete immunoglobulin molecule can consist of heavy chains only with no light chains.

In naturally occurring antibodies, there are six CDRs present in each antigen binding domain that are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops that connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable domain by one of ordinary skill in the art, since they have been precisely defined (see e.g., Chothia & Lesk, 1987; Kabat et al., 1991; Martin, 1996; Johnson & Wu, 2000).

A particular kind of chimeric antibody is a "humanized" antibody, in which the antibodies are produced by substituting the CDRs of, for example, a mouse antibody, for the CDRs of a human antibody (see e.g., PCT International Patent Application Publication No. WO 1992/22653). Thus, in some embodiments, a humanized antibody has constant regions and variable regions other than the CDRs that are derived substantially or exclusively from the corresponding regions of a human antibody, and CDRs that are derived substantially or exclusively from a mammal other than a human.

Fv fragments correspond to the variable fragments at the N-termini of immunoglobulin heavy and light chains. Fv fragments appear to have lower interaction energy of their two chains than Fab fragments. To stabilize the association of the VH and VL domains, they can be linked with peptides (see e.g., Bird et al., 1988; Huston et al., 1988), disulfide bridges (see e.g., Glockshuber et at, 1990), and/or "knob in hole" mutations (see e.g., Zhu et al., 1997). ScFv fragments can be produced by methods well known to those skilled in the art (see e.g., Whitlow et al., 1991; Huston et al., 1993).

A "single-chain variable fragment" (scFv) is a fusion protein of the variable regions of the heavy (VH) and light chains (VL) of immunoglobulins, connected with a short linker peptide. The linker can be rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and the introduction of the linker. scFv can be produced in bacterial cells such as *E. coli* or in eukaryotic cells.

Methods and Compositions scFvs, Diabodies, Tribodies, and Tetrabodies, and Nucleic Acids Thereof Antibodies recognizing TAG-72 provide a novel approach for the imaging, detection, and treatment of cancer. Antibody fragments that binds specifically to the sialyl-Tn surface adhesin of TAG-72 is disclosed herein. The antibody fragment derivatives of the present invention are advantageously useful over other antibody and antibody fragments known in the art because they are easy to express in large quantities, can penetrate tissues easily and lack the constant domains that promote often unwanted and usually superfluous effector functions. ScFvs are monovalent because the heavy and light chains are joined by a flexible peptide linker, which allows the two domains to fold and interact with each other. By using antibody fragments, such as diabodies, wherein the linking peptide is shortened thereby forcing the heavy and light chain variable domains to interact to form a dimer, the drawback of using scFvs is overcome. Further, as a consequence of this interaction, the antibody fragment is bivalent like the parent immunoglobulin, and therefore has increased binding avidity.

Recombinant antibody fragments can be engineered to assemble into stable multimeric oligomers of high binding avidity and specificity (Kortt, et al. (2001) Biomol. Eng. 18:95-108). A scFv molecule joined by a linker of 3-12 residues cannot fold into a functional Fv domain and instead associates with a second scFv molecule to form a bivalent dimer (diabody, approx. 60 kDa). For the cross-linking of cell surface antigens at least two binding moieties are necessary. The diabody is the smallest bivalent antibody molecule able to fulfill this requisite.

As used herein, the term "diabody" refers to an engineered antibody construct prepared by isolating the binding domains (both heavy and light chain) of a binding antibody, and supplying a linking moiety which joins or operably links the heavy and light chains on the same polypeptide chain thereby preserving the binding function as described in detail by Holliger et al. (1993) Proc. Natl. Acad. Sci. USA 90:6444 and reviewed by Poljak (1994) Structure 2:1121-1123. This forms, in essence, a radically abbreviated antibody, having only the variable domain necessary for binding the antigen. By using a linker that is too short to allow pairing between the two domains on the same chain, the domains are forced to pair with the complementary domains of another chain and create two antigen-binding sites. These dimeric antibody fragments, or diabodies, are bivalent and bispecific. It should be clear that any method to generate diabodies, or other types of multimers, as for example described by Holliger, et al. (1993) supra, Poljak (1994) supra, Zhu, et al. (1996) Biotechnology 14:192-196, and U.S. Pat. No. 6,492,123, herein incorporated by reference, can be used. Once generated, the binding specificity can be determined by, for example, equilibrium methods (e.g., enzyme-linked immunoabsorbent assay (ELISA) or radioimmunoassay (RIA)), or kinetics (e.g. BIACORE™ analysis). Alternatively, the diabody can be subjected to other biological activity assays, e.g., bacterial aggregation or colonization assays, in order to evaluate its potency or pharmacological activity and potential efficacy as a therapeutic agent. Such assays are disclosed herein and are well-known in the art. The term "diabody," as used herein, can also generally refer to an antibody fragment that can comprise a mixture of diabodies, tribodies, tetrabodies, or other antibody fragments known in the art.

The generation of antibody fragments containing the human variable domains is described further in the Examples section of the present application.

Disclosed herein are antibody fragments which specifically bind tumor-associated glycoprotein 72 (TAG-72). Even more specifically, they can bind the sialyl-Tn epitope of TAG-72. These highly stable, high-affinity, bacterially-expressible antibody fragments are capable of specifically binding to a sialyl-Tn glycoform epitope found in TAG-72, a mucin-like glycoprotein found in human adenocarcinomas. This epitope is rarely expressed in the microenvironment of healthy tissue and thus provides a specific target for imaging and detection. Radiolabeled antibodies that specifically bind Sialyl-Tn allow one to image at the molecular level and provide the ability to improve patient care. Various molecules—B72.3, CC49, huCC49, 3E8—demonstrate the utility of anti-TAG-72 antibodies in cancer diagnosis and imaging.

3E8.G$^4$S, an antibody fragment that incorporates structural and binding site components from a CC49 scFv and the 3E8 antibody, as well as other sequence features for bacterial expression and purification, are described herein. Also described herein are the DNA sequences, protein sequences, and method of expression in and purification from *Escherichia coli*.

The antibody fragments disclosed herein have the following properties: tight and specific binding to the cancer epitope, sialyl-Tn (Thor 1986; Thor 1987), enhanced stability for longer shelf life, performance during application, resistance to serum proteases; improved expression and purification from bacteria; amenability to further engineering; reduced immunogenicity; and increased tissue penetrance over full-length antibodies (IgG) and fragment antigen binding (Fab) domains (Yokota 1992) Several of these properties exist in one or more sialyl-Tn binding proteins, but to date, no single molecule combines all desired features (Colcher 1999; Yoon 2006).

Specifically, the antibody fragments disclosed herein can have a shelf life of 1, 2, 3, 4, 5, 6, 7, 8, 9, 10, 11, or 12 weeks, or 3, 4, 5, 6, 7, 8, 9, 10, 11, or 12 months, or 1 2, 3, 4, 5, 6, 7, 8, 9, or 10 years more than a full-length antibody (IgG) or Fab domain The antibody fragments disclosed herein can be 2, 3, 4, 5, 6, 7, 8, 9, or 10 times, or any amount smaller, larger or in between, more resistance to serum proteases. They can have 2, 3, 4, 5, 6, 7, 8, 9, or 10 times, or any amount smaller, larger or in between, reduced immunogenicity when compared with a full length IgG or Fab domain They can have 2, 3, 4, 5, 6, 7, 8, 9, or 10 times, or any amount smaller, larger or in between, increased tissue penetrance compared with a full length IgG or Fab domain. They can have 1, 2, or 3 or more of these characteristics.

To generate a cancer detection and imaging agent with the above features, antibody fragments have been engineered (SEQ ID NOS 13, 15, 17, 19, 21, 23, 25, 27, 29, 31, 33, 35, 37, 39, 41, 43, and 45 are examples). Additionally, the compactness of antibody fragments, such as diabodies or mixtures thereof, and lack of cellular uptake improve tissue penetrance and provide more flexible serum half-lives. The clearance rates are faster than IgGs which is desired when using harmful radionuclides, but can be extended by PEGylation to complement a wider pairing of isotopes (Yang 2003). The 3E8-inspired antibody fragments disclosed herein are humanized for reduced immunogenicity, expresses well in bacteria, are 1, 2, 3, 4, 5, 6, 7, 8, 9, 10, 11, 12, 13, 14, 15, 16, 17, 18, 19, or 20° C. more stable than the clinically tested CC49.scFv, and bind the sialyl-Tn antigen with low nanomolar affinity.

The antibody fragments disclosed herein can be made in a variety of ways, as one of skill in the art will appreciate. In its most essential form, the antibody fragment can comprise a heavy chain variable region comprising SEQ ID NO: 10, and a light chain variable region comprising SEQ ID NO: 11, or a fragment of SEQ ID NO: 10 and 11. For example, an antibody fragment such as a diabody can be produced which has 60, 70, 80, 90, 91, 92, 93, 94, 95, 96, 97, 98, or 99% identity to SEQ ID NO: 10, and 60, 70, 80, 90, 91, 92, 93, 94, 95, 96, 97, 98, or 99% identity to SEQ ID NO: 11. The antibody fragments can be functionally equivalent to those found in SEQ ID NOS 10 and 11.

The linker between the heavy and light chains can be 2, 3, 4, 5, 6, 8, 9, or 10 amino acids long.

The antibody fragments can have an antigen binding affinity for sialyl-Tn which is at least 25% that of 3E8. 3E8 has shown an anti-tumor therapeutic effect in athymic mice bearing human colon adenocarcinoma xenografts (Yoon 2006).

The presently disclosed subject matter includes functional equivalents of the antibodies of the presently disclosed subject matter. As used herein, the phrase "functional equivalent" as it refers to an antibody refers to a molecule that has binding characteristics that are comparable to those of a given antibody. In some embodiments, chimerized, humanized, and single chain antibodies, as well as fragments thereof, are considered functional equivalents of the corresponding antibodies upon which they are based. Functional equivalents also include polypeptides with amino acid sequences substantially the same as the amino acid sequence of the variable or hypervariable regions of the antibodies of the presently disclosed subject matter. As used herein with respect to nucleic acid and/or amino acid sequences, the phrase "substantially the same" refers to a biosequence with in some embodiments at least 80%, in some embodiments at least 85%, in some embodiments at least about 90%, in some embodiments at least 91%, in some embodiments at least 92%, in some embodiments at least 93%, in some embodiments at least 94%, in some embodiments at least 95%, in some embodiments at least 96%, in some embodiments at least 97%, in some embodiments at least 98%, and in some embodiments at least about 99% sequence identity to another nucleic acid and/or amino acid sequence, as determined by the FASTA search method in accordance with Pearson & Lipman, 1988. In some embodiments, the percent identity calculation is performed over the full length of the nucleic acid and/or amino acid sequence of an antibody of the presently disclosed subject matter.

Specifically disclosed herein is an amino acid sequence comprising 90% identity to SEQ ID NOS 13, 15, 17, 19, 21, 23, 25, 27, 29, 31, 33, 35, 37, 39, 41, 43, or 45. Further disclosed is a nucleic acid sequence from which may be expressed an antibody fragment, such as the antibody fragments disclosed herein. Also disclosed is nucleic acid sequence from which may be expressed from the antibody fragments of the present invention. Disclosed herein is a nucleic acid sequence comprising 90% identity to SEQ ID NO: 12, 14, 16, 18, 20, 22, 24, 26, 28, 30, 32, 34, 36, 38, 40, 42, or 44. Also disclosed is a vector comprising the nucleic acids disclosed herein. Vectors include, but are not limited to, a bare nucleic acid segment, a carrier-associated nucleic acid segment, a nucleoprotein, a plasmid, a virus, a viroid, or a transposable element. Also disclosed is a cell that produces the antibody fragments of the present invention.

Treatment Methods

Disclosed herein are compositions comprising an antibody fragment of the present invention, and a pharmaceutically acceptable carrier. For example, disclosed are compositions useful for the treatment of cancer comprising a therapeutically effective amount of an antibody fragment, such as a diabody. For instance, the diabody can be, directly or indirectly, associated with or linked to an effector moiety having therapeutic activity, and the composition is suitable for the treatment of cancer. The effector moiety can be a radionuclide, therapeutic enzyme, anti-cancer drug, cytokine, cytotoxin, or anti-proliferative agent.

Disclosed herein is a method for in vivo treatment of a mammal having a TAG-72-expressing cancer comprising a step of administering to the mammal a therapeutically effective amount of a composition comprising an antibody fragment of the present invention.

Also disclosed is a method for suppressing tumor growth in a subject, the method comprising administering to a subject bearing a tumor an effective amount of an antibody fragment composition, wherein the antibody fragment is coupled to an anti-tumor composition. By "suppressing tumor growth" is meant that a tumor grows less than one which is not treated (a control). For example, suppressed tumor growth can mean that the tumor being treated grows 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100% less than the measured growth of a control over the same period of time.

Administration

The antibody fragments of the invention may be administered to a mammal in accordance with the aforementioned methods of treatment in an amount sufficient to produce such effect to a therapeutic, prophylactic, or diagnostic effect. Such antibodies of the invention can be administered to such mammal in a conventional dosage form prepared by combining the antibody of the invention with a conventional pharmaceutically acceptable carrier or vehicle, diluent, and/or excipient according to known techniques to form a suspension, injectable solution, or other formulation. It will be recognized by one of skill in the art that the form and character of the pharmaceutically acceptable carrier or diluent is dictated by the amount of active ingredient with which it is to be combined, the route of administration and other well-known variables.

Pharmaceutically acceptable formulations may include, e.g., a suitable solvent, preservatives such as benzyl alcohol if desired, and a buffer. Useful solvent may include, e.g., water, aqueous alcohols, glycols, and phosphate and carbonate esters. Such aqueous solutions contain no more than 50% by volume of organic solvent. Suspension-type formulations may include a liquid suspending medium as a carrier, e.g., aqueous polyvinylpyrrolidone, inert oils such as vegetable oils or highly refined mineral oils, or aqueous cellulose ethers such as aqueous carboxymethylcellulose. A thickener such as gelatin or an alginate may also be present, one or more natural or synthetic surfactants or antifoam agents may be used, and one or more suspending agents such as sorbitol or another sugar may be employed therein. Such formations may contain one or more adjuvants.

The route of administration of the antibody fragment of the invention may be oral, parenteral, by inhalation or topical. The term parenteral as used herein includes intravenous, intramuscular, subcutaneous, rectal, vaginal or intraperitoneal administration. The subcutaneous, intravenous and intramuscular forms of parenteral administration are generally preferred. The daily parenteral and oral dosage regimens for employing humanized antibodies of the invention prophylactically or therapeutically will generally be in the range of about 0.005 to 100, but preferably about 0.5 to 10, milligrams per kilogram body weight per day.

The antibody fragment of the invention may also be administered by inhalation. By "inhalation" is meant intranasal and oral inhalation administration. Appropriate dosage forms for such administration, such as an aerosol formulation or a metered dose inhaler, may be prepared by conventional techniques. The preferred dosage amount of a compound of the invention to be employed is generally within the range of about 0.1 to 1000 milligrams, preferably about 10 to 100 milligrams/kilogram body weight.

The antibody fragment of the invention may also be administered topically. By topical administration is meant non-systemic administration. This includes the administration of a humanized antibody (or humanized antibody fragment) formulation of the invention externally to the epidermis or to the buccal cavity, and instillation of such an antibody into the ear, eye, or nose, and wherever it does not significantly enter the bloodstream. By systemic administration is meant oral, intravenous, intraperitoneal, subcutaneous, and intramuscular administration. The amount of an antibody required for therapeutic, prophylactic, or diagnostic effect will, of course, vary with the antibody chosen, the nature and severity of the condition being treated and the animal undergoing treatment, and is ultimately at the discretion of the physician. A suitable topical dose of an antibody of the invention will generally be within the range of about 1 to 100 milligrams per kilogram body weight daily.

Formulations

While it is possible for an antibody fragment to be administered alone, it is preferable to present it as a pharmaceutical formulation. The active ingredient may comprise, for topical administration, from 0.001% to 10% w/w, e.g., from 1% to 2% by weight of the formulation, although it may comprise as much as 10% w/w but preferably not in excess of 5% w/w and more preferably from 0.1% to 1% w/w of the formulation. The topical formulations of the present invention, comprise an active ingredient together with one or more acceptable carrier(s) therefor and optionally any other therapeutic ingredients(s). The carrier(s) must be "acceptable" in the sense of being compatible with the other ingredients of the formulation and not deleterious to the recipient thereof.

Formulations suitable for topical administration include liquid or semi-liquid preparations suitable for penetration through the skin to the site of where treatment is required, such as liniments, lotions, creams, ointments or pastes, and drops suitable for administration to the eye, ear, or nose. Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified and sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

Kits according to the present invention include antibody fragments as disclosed herein, and instructions for their use. Frozen or lyophilized humanized antibody fragments to be reconstituted, respectively, by thawing (optionally followed by further dilution) or by suspension in a (preferably buffered) liquid vehicle can also be used in these kits. The kits may also include buffer and/or excipient solutions (in liquid or frozen form)—or buffer and/or excipient powder preparations to be reconstituted with water—for the purpose of mixing with the humanized antibodies or humanized antibody fragments to produce a formulation suitable for administration. Thus, preferably the kits containing the humanized antibodies or humanized antibody fragments are frozen, lyophilized, pre-diluted, or pre-mixed at such a concentration that the addition of a predetermined amount of heat, of water, or of a solution provided in the kit will result in a formulation of sufficient concentration and pH as to be effective for in vivo or in vitro use in the treatment or diagnosis of cancer. Preferably, such a kit will also comprise instructions for reconstituting and using the humanized antibody or humanized antibody fragment composition to treat or detect cancer. The kit may also comprise two or more component parts for the reconstituted active composition. For example, a second component part—in addition to the humanized antibodies or humanized antibody fragments—may be bifunctional chelant, bifunctional chelate, or a therapeutic agent such as a radionuclide, which when mixed with the humanized antibodies or humanized antibody fragments forms a conjugated system therewith. The above-noted buffers, excipients, and other component parts can be sold separately or together with the kit.

It will be recognized by one of skill in the art that the optimal quantity and spacing of individual dosages of a humanized antibody or humanized antibody fragment of the invention will be determined by the nature and extent of the condition being treated, the form, route and site of administration, and the particular animal being treated, and that such optima can be determined by conventional techniques. It will also be appreciated by one of skill in the art that the optimal course of treatment, i.e., the number of doses of an antibody or fragment thereof of the invention given per day for a defined number of days, can be ascertained by those skilled in the art using conventional course of treatment determination tests.

Active Agents

The compositions of the presently disclosed subject matter can comprise an active agent, wherein the active agent comprises a therapeutic moiety, a diagnostic moiety, and/or a biologically active moiety. As used herein, the phrase "active agent" thus refers to a component of the presently disclosed compositions that provides a therapeutic benefit to a subject, permits visualization of cells or tissues in which the compositions of the presently disclosed subject matter accumulate, detection of epitopes to which the presently disclosed antibody fragments bind, and/or enhances any of these activities. In some embodiments, an active agent of the presently disclosed subject matter is selected from the group consisting of a radioactive molecule (including, but not limited to radionuclides and radioisotopes), a sensitizer molecule, an imaging agent or other detectable agent, a toxin, a cytotoxin, an anti-angiogenic agent, an anti-tumor agent, a chemotherapeutic agent, an immunomodulator, a cytokine, a reporter group, and combinations thereof. It is understood that these categories are not intended to be mutually exclusive, as some radioactive molecules, for example, are also chemotherapeutic agents, some immunomodulators are cytokines, etc.

In some embodiments, an active agent comprises a chemotherapeutic. Various chemotherapeutics are known to one of ordinary skill in the art, and include, but are not limited to alkylating agents such as nitrogen mustards (e.g., Chlorambucil, Cyclophosphamide, Isofamide, Mechlorethamine, Melphalan, Uracil mustard), aziridines (e.g., Thiotepa), methanesulfonate esters (e.g., Busulfan), nitroso ureas (e.g., Carmustine, Lomustine, Streptozocin), platinum complexes (e.g., Cisplatin, Carboplatin), and bioreductive alkylators (e.g., Mitomycin C, Procarbazine); DNA strand breaking agents (e.g., Bleomycin); DNA topoisomerase I inhibitors (e.g., camptothecin and derivatives thereof including, but not limited to 10-hydroxycamptothecin), DNA topoisomerase II inhibitors (e.g., Amsacrine, Dactinomycin, Daunorubicin, Doxorubicin, Idarubicin, Mitoxantrone, Etoposide, Teniposide, Podophyllotoxin); DNA minor groove binders (e.g., Plicamycin); anti-metabolites such as folate antagonists (e.g., Methotrexate and trimetrexate), pyrimidine antagonists (e.g., Fluorouracil, Fluorodeoxyuridine, CB3717, Azacytidine, Cytarabine, Floxuridine), purine antagonists (e.g., Mercaptopurine, 6-Thioguanine, Fludarabine, Pentostatin), sugar modified analogs (e.g., Cyctrabine, Fludarabine), and ribonucleotide reductase inhibitors (e.g., Hydroxyurea); tubulin interactive agents (e.g., Vincristine, Vinblastine, Paclitaxel); adrenal corticosteroids (e.g., Prednisone, Dexamethasone, Methylprednisolone, Prednisolone); hormonal blocking agents such as estrogens and related compounds (e.g., Ethinyl Estradiol, Diethylstilbesterol, Chlorotrianisene, Idenestrol), progestins (e.g., Hydroxyprogesterone caproate, Medroxyprogesterone, Megestrol), androgens (e.g., Testosterone, Testosterone propionate; Fluoxymesterone, Methyltestosterone), leutinizing hormone releasing hormone agents and/or gonadotropinreleasing hormone antagonists (e.g., Leuprolide acetate; Goserelin acetate), anti-estrogenic agents (e.g., Tamoxifen), anti-androgen agents (e.g., Flutamide), and anti-adrenal agents (e.g., Mitotane, Aminoglutethimide). Other chemotherapeutics include, but are not limited to Taxol, retinoic acid and derivatives thereof (e.g., 13-cis-retinoic acid, all-trans-retinoic acid, and 9-cis-retinoic acid), sulfathiazole, mitomycin C, mycophenolic acid, sulfadiethoxane, and gemcitabine (4-amino-1-(2-deoxy-2,2-difluoro-D-eryi/7ropentofuranosyl)pyhmidin-2(1H)-on-2',2'-difluoro-2'-deoxycytidine).

The subject antibody fragments may also be administered in combination with other anti-cancer agents, e.g., other antibodies or drugs. Also, the subject humanized antibody fragments may be directly or indirectly attached to effector having therapeutic activity, Suitable effector moieties include by way of example cytokines (IL-2, TNF, interferons, colony stimulating factors, IL-1, etc.), cytotoxins (Pseudomonas exotoxin, ricin, abrin, etc.), radionuclides, such as $^{90}Y$, $^{131}I$, $^{99m}Tc$, $^{111}In$ $^{125}I$, among others, drugs (methotrexate, daunorubicin, doxorubicin, etc.), immunomodulators, therapeutic enzymes (e.g., beta-galactosidase), anti-proliferative agents, etc. The attachment of antibodies to desired effectors is well known. See, e.g., U.S. Pat. No. 5,435,990 to Cheng et al. Moreover, bifunctional linkers for facilitating such attachment are well known and widely available, Also, chelators (chelants and chelates) providing for attachment of radionuclides are well known and available.

The compositions of the presently disclosed subject matter can further comprise a drug carrier to facilitate drug preparation and administration. Any suitable drug delivery vehicle or carrier can be used, including but not limited to a gene therapy vector (e.g., a viral vector or a plasmid), a microcapsule, for example a microsphere or a nanosphere (Manome et al; 1994; Hallahan et al., 2001 b; Saltzman & Fung, 1997), a peptide (U.S. Pat. Nos. 6,127,339 and 5,574,172), a glycosaminoglycan (U.S. Pat. No. 6,106,866), a fatty acid (U.S. Pat. No. 5,994,392), a fatty emulsion (U.S. Pat. No. 5,651,991), a lipid or lipid derivative (U.S. Pat. No. 5,786,387), collagen (U.S. Pat. No. 5,922,356), a polysaccharide or derivative thereof (U.S. Pat. No. 5,688,931), a nanosuspension (U.S. Pat. No. 5,858,410), a polymeric micelle or conjugate (Goldman et al., 1997; U.S. Pat. Nos. 4,551,482; 5,714,166; 5,510,103; 5,490,840; and 5,855, 900), and a polysome (U.S. Pat. No. 5,922,545).

The disclosed antibody fragments can also be coupled to drugs or drug carriers using methods known in the art, including but not limited to carbodiimide conjugation, esterification, sodium periodate oxidation followed by reductive alkylation, and glutaraldehyde crosslinking (see e.g., U.S. Pat. No. 6,071,890; and European Patent No. 0 439 095).

Detection Methods

Disclosed are compositions suitable for the in vivo or in vitro detection of cancer comprising a diagnostically effective amount of an antibody fragment disclosed herein. The antibody fragment can be, directly or indirectly, associated with or linked to a detectable label, and the composition can be suitable for detection of cancer. Also disclosed is a method for in vitro immunodetection of TAG-72-expressing cancer cells comprising a step of contacting the cancer cells with a composition comprising an antibody fragment of the present invention. The antibody fragment can be bound to a solid support, for example.

Also disclosed is a method of in vivo immunodetection of TAG-72-expressing cancer cells in a mammal comprising a step of administering to the mammal a diagnostically effective amount of a composition comprising the antibody fragment of the present invention.

For diagnostic applications, a detectable amount of a composition of the presently disclosed subject matter is administered to a subject. A "detectable amount", as used herein to refer to a composition, refers to a dose of such a composition that the presence of the composition can be determined in vivo or in vitro. A detectable amount will vary according to a variety of factors, including but not limited to chemical features of the composition being labeled, the detectable label, the labeling methods, the method of imaging and parameters related thereto, metabolism of the labeled drug in the subject, the stability of the label (including, but not limited to the half-life of a radionuclide label), the time elapsed following administration of the composition prior to imaging, the route of administration, the physical condition and prior medical history of the subject, and the size and longevity of the tumor or suspected tumor. Thus, a detectable amount can vary and can be tailored to a particular application. After study of the present disclosure, it is within the skill of one in the art to determine such a detectable amount.

As used herein, the terms "detectable moiety", "detectable label", and "detectable agent" refer to any molecule that can be detected by any moiety that can be added to an antibody fragment that allows for the detection of the antibody fragment in vitro and/or in vivo. Representative detectable moieties include, but are not limited to, chromophores, fluorescent moieties, enzymes, antigens, groups with specific reactivity, chemiluminescent moieties, and electrochemically detectable moieties, etc. In some embodiments, the antibodies are biotinylated.

Detection and imaging of the antibody fragment is tunable, such that imaging can be performed in under 1, 2, 4, 6, 12, or 18, 24, 36, or 48 hours, or any amount below, above, or between this amount. It has been demonstrated that PEGs/larger fragments increase serum half-life by 2, 3, 4, 5, 6, 7, 8, 9, 10, 15, 20, 25, 30, 35, 40, 45, 50, 55, 60, 65, 70, 75, 80, 85, 90, 95, or 100%, or 2, 3, 4, 5, 6, 7, 8, 9, or 10 or more times compared to a smaller fragment. This allows for imaging at different time points. For therapeutic purposes, it allows for an increase in the therapeutic window.

Detectable Moieties

In some embodiments, a detectable moiety comprises a fluorophore. Any fluorophore can be employed with the compositions of the presently disclosed subject matter, provided that the conjugation of fluorophore results in a composition that is detectable either in vivo (e.g., after administration to a subject) and/or in vitro, and further does not negatively impact the ability of the antibody fragment to bind to its epitope. Representative fluorophores include, but are not limited to 7-dimethylaminocoumarin-3-carboxylic acid, dansyl chloride, nitrobenzodiazolamine (NBD), dabsyl chloride, cinnamic acid, fluorescein carboxylic acid, Nile Blue, tetramethylcarboxyrhodamine, tetraethylsulfohodamine, 5-carboxy-X-rhodamine (5-ROX), and 6-carboxy-X-rhodamine (6-ROX). It is understood that these representative fluorophores are exemplary only, and additional fluorophores can also be employed. For example, there the ALEXA FLUOR® dye series includes at least 19 different dyes that are characterized by different emission spectra. These dyes include ALEXA FLUOR® 350, 405, 430, 488, 500, 514, 532, 546, 555, 568, 594, 610, 633, 635, 647, 660, 680, 700, and 750 (available from Invitrogen Corp., Carlsbad, Calif., United States of America), and the choice of which dye to employ can be made by the skilled artisan after consideration of the instant specification based on criteria including, but not limited to the chemical compositions of the specific ALEXA FLUOR®, whether multiple detectable moieties are to be employed and the emission spectra of each, the detection technique to be employed, etc.

In some embodiments, a detectable moiety comprises a cyanine dye. Non-limiting examples of cyanine dyes that can be conjugated to the antibody fragments of the presently disclosed subject matter include the succinimide esters Cy5, Cy5.5, and Cy7, supplied by Amersham Biosciences (Piscataway, N.J., United States of America).

In some embodiments, a detectable moiety comprises a near infrared (NIR) dye. Non-limiting examples of near infrared dyes that can be conjugated to the antibody fragment of the presently disclosed subject matter include NIR641, NIR664, NIT7000, and NIT782.

In some embodiments, the biotinylated antibodies are detected using a secondary antibody that comprises an avidin or streptavidin group and is also conjugated to a fluorescent label including, but not limited to Cy3, Cy5, Cy7, and any of the ALEXA FLUOR®® series of fluorescent labels available from INVITROGEN™ (Carlsbad, Calif., United States of America). In some embodiments, the antibody fragment is directly labeled with a fluorescent label and cells that bind to the antibody fragment are separated by fluorescence-activated cell sorting. Additional detection strategies are known to the skilled artisan.

For diagnostic applications (including but not limited to detection applications and imaging applications), the antibodies of the presently disclosed subject matter can be labeled with a detectable moiety. The detectable moiety can be any one that is capable of producing, either directly or indirectly, a detectable signal. For example, a detectable moiety can be a radioisotope, such as but not limited to $^3$H, $^{14}$C, $^{32}$P, $^{35}$S, $^{125}$I, or $^3$I; a fluorescent or chemiluminescent compound such as but not limited to fluorescein isothiocyanate, rhodamine, or luciferin; or an enzyme, such as but not limited to alkaline phosphatase, β-galactosidase, or horseradish peroxidase.

The presently disclosed subject matter further provides methods for diagnosing a tumor, wherein a tumor sample or biopsy is evaluated in vitro. In some embodiments, a targeting ligand of the presently disclosed subject matter comprises a detectable label such as a fluorescent label, an epitope tag, or a radioactive label, each described briefly herein below.

Detection of an Epitope Tag

If an epitope label has been used, a protein or compound that binds the epitope can be used to detect the epitope. A representative epitope label is biotin, which can be detected by binding of an avidin-conjugated fluorophore, for example avidin-FITC. Alternatively, the label can be detected by binding of an avidin-horseradish peroxidase (HRP) streptavidin conjugate, followed by colorimetric detection of an HRP enzymatic product. The production of a colorimetric or luminescent product/conjugate is measurable using a spectrophotometer or luminometer, respectively.

Autoradiographic Detection

In the case of a radioactive label (e.g., $^{131}$I or $^{99m}$Tc) detection can be accomplished by conventional autoradiography or by using a phosphorimager as is known to one of skill in the art. A preferred autoradiographic method employs photostimulable luminescence imaging plates (Fuji Medical Systems of Stamford, Conn., United States of America). Briefly, photostimulable luminescence is the quantity of light emitted from irradiated phosphorous plates following stimulation with a laser during scanning The luminescent response of the plates is linearly proportional to the activity.

Any method known in the art for conjugating an antibody to a detectable moiety can be employed.

Immunohistochemistry

Disclosed herein are methods of using immunohistochemistry (IHC) utilizing the antibody fragments disclosed herein to detect cancer. IHC detects target molecules through antigen-antibody complexes in a pathological specimen using enzyme-linked antigens or antibodies. The presence of the target molecule can then detected via an enzyme immunoassay.

A multitude of benefits are realized with IHC versus traditional immunofluorescence. For example, unlike immunofluorescence, IHC can be used with commonly used formalin-fixed paraffin-embedded tissue specimens. Pathological specimens, including histological tissue sections and/or other biological preparations such as tissue culture cells and PAP smears, are commonly used in diagnostic pathology and can be easily screened via IHC. Further, IHC staining is permanent and preserves cell morphology. A comparison of the cell morphology and antigen proliferation on two different slides can be useful in monitoring the progression of a disease.

Once a labeled antibody has been attached, either directly or indirectly, to the specimen, a substrate, specific for the enzyme, is added to the specimen. When the substrate is added, the enzyme label converts the substrate causing a color change that can be seen with light microscopy. The presence of a color change indicates the presence of the target molecule and allows an observer to determine, assess, and diagnose the disease level and severity.

In Vivo Imaging

The antibody fragments of the presently disclosed subject matter also are useful for in vivo imaging, wherein an antibody labeled with a detectable moiety such as a radio-opaque agent and/or a radioisotope is administered to a subject, in some embodiments via intravenous administration, and the presence and location of the labeled antibody in the host is assayed. This imaging technique can be useful in the staging and treatment of malignancies.

Therefore, disclosed is a method of in vivo treatment of cancer comprising the steps of: (a) intravenously administering a radionuclide-labeled antibody fragment; (b) thereafter detecting tumor cells using a radionuclide activity probe; and (c) thereafter removing the detected tumor cells by surgical excision.

Thus, in some embodiments, a composition of the presently disclosed subject matter comprises a label that can be detected in vivo. The term "in vivo" as used herein to describe imaging or detection methods, refers to generally non-invasive methods such as scintigraphic methods, magnetic resonance imaging, ultrasound, or fluorescence, each described briefly herein below. The term "non-invasive methods" does not exclude methods employing administration of a contrast agent to facilitate in vivo imaging.

In some embodiments, the detectable moiety can be conjugated or otherwise associated with the antibody fragment of the presently disclosed subject matter, a therapeutic, a diagnostic agent, a drug carrier, or combinations thereof as set forth in more detail hereinabove. Following administration of the labeled composition to a subject, and after a time sufficient for binding, the biodistribution of the composition can be visualized. The term "time sufficient for binding" refers to a temporal duration that permits binding of the labeled agent to a radiation-induced target molecule.

Scintigraphic Imaging

Scintigraphic imaging methods include SPECT (Single Photon Emission Computed Tomography), PET (Positron Emission Tomography), gamma camera imaging, and rectilinear scanning A gamma camera and a rectilinear scanner each represent instruments that detect radioactivity in a single plane. Most SPECT systems are based on the use of one or more gamma cameras that are rotated about the subject of analysis, and thus integrate radioactivity in more than one dimension. PET systems comprise an array of detectors in a ring that also detect radioactivity in multiple dimensions.

Imaging instruments suitable for practicing the detection and/or imaging methods of the presently disclosed subject matter, and instruction for using the same, are readily available from commercial sources. For example, a SPECT scanner can be used with a CT scanner, with coregistration of images. As in PET/CT, this allows location of tumors or tissues which may be seen on SPECT scintigraphy, but are difficult to precisely locate with regard to other anatomical structures. Both PET and SPECT systems are offered by ADAC of Milpitas, Calif., United States of America, and Siemens of Hoffman Estates, Ill., United States of America. Related devices for scintigraphic imaging can also be used, such as a radio-imaging device that includes a plurality of sensors with collimating structures having a common source focus.

When scintigraphic imaging is employed, the detectable label comprises in some embodiments a radionuclide label, in some embodiments a radionuclide label selected from the group consisting of $^{18}$F, $^{64}$Cu, $^{65}$Cu, $^{67}$Ga, $^{68}$Ga, $^{77}$Br, $^{80m}$Br, $^{95}$Ru, $^{97}$Ru, $^{103}$Ru, $^{105}$Ru, $^{99m}$Tc, $^{107}$Hg, $^{203}$Hg, $^{123}$I, $^{124}$I, $^{125}$I, $I$ $^{131}$I, $^{133}$I, $^{111}$In, $^{113m}$In, $^{99m}$Re, $^{105}$Re, $^{101}$Re, $^{186}$Re, $^{188}$Re, $^{121m}$Te, $^{122m}$Te, $^{125m}$Te, $^{165}$Tm, $^{167}$Tm, $^{168}$Tm, and nitride or oxide forms derived there from. In some embodiments, the radionuclide label comprises $^{131}$I or $^{99m}$Tc.

Methods for radionuclide labeling of a molecule so as to be used in accordance with the disclosed methods are known in the art. For example, a targeting molecule can be derivatized so that a radioisotope can be bound directly to it. Alternatively, a linker can be added that to enable conjugation. Representative linkers include diethylenetriamine pentaacetate (DTPA)-isothiocyanate, succinimidyl 6-hydrazinium nicotinate hydrochloride (SHNH), and hexamethylpropylene amine oxime (U.S. Pat. No. 6,024, 938). Additional methods can be found in U.S. Pat. No. 6,080,384.

When the labeling moiety is a radionuclide, stabilizers to prevent or minimize radiolytic damage, such as ascorbic acid, gentisic acid, or other appropriate antioxidants, can be added to the composition comprising the labeled targeting molecule.

Magnetic Resonance Imaging (MRI)

Magnetic resonance image-based techniques create images based on the relative relaxation rates of water protons in unique chemical environments. As used herein, the term "magnetic resonance imaging" refers to magnetic source techniques including convention magnetic resonance imaging, magnetization transfer imaging (MTI), proton magnetic resonance spectroscopy (MRS), diffusion-weighted imaging (DWI) and functional MR imaging.

Contrast agents for magnetic source imaging include but are not limited to paramagnetic or superparamagnetic ions, iron oxide particles, and water-soluble contrast agents. Paramagnetic and superparamagnetic ions can be selected from the group of metals including iron, copper, manganese, chromium, erbium, europium, dysprosium, holmium and gadolinium. Preferred metals are iron, manganese and gadolinium; most preferred is gadolinium.

Those skilled in the art of diagnostic labeling recognize that metal ions can be bound by chelating moieties, which in turn can be conjugated to a therapeutic agent in accordance with the methods of the presently disclosed subject matter. For example, gadolinium ions are chelated by diethylenetriaminepentaacetic acid (DTPA). Lanthanide ions are chelated by tetraazacyclododocane compounds. See U.S. Pat. Nos. 5,738,837 and 5,707,605. Alternatively, a contrast agent can be carried in a liposome.

Images derived used a magnetic source can be acquired using, for example, a superconducting quantum interference device magnetometer (SQUID, available with instruction from Quantum Design of San Diego, Calif., United States of America; see also U.S. Pat. No. 5,738,837).

Ultrasound

Ultrasound imaging can be used to obtain quantitative and structural information of a target tissue, including a tumor. Administration of a contrast agent, such as gas microbubbles, can enhance visualization of the target tissue during an ultrasound examination. In some embodiments, the contrast agent can be selectively targeted to the target tissue of interest, for example by using a peptide for guided drug delivery (e.g., radiation guided drug delivery) as disclosed herein. Representative agents for providing microbubbles in vivo include but are not limited to gas-filled lipophilic or lipid—based bubbles (e.g., U.S. Pat. Nos. 6,245,318; 6,231,834; 6,221,018; and 5,088,499). In addition, gas or liquid can be entrapped in porous inorganic particles that facilitate microbubble release upon delivery to a subject (U.S. Pat. Nos. 6,254,852 and 5,147,631).

Gases, liquids, and combinations thereof suitable for use with the presently disclosed subject matter include air; nitrogen; oxygen; is carbon dioxide; hydrogen; nitrous oxide; an inert gas such as helium, argon, xenon or krypton; a sulfur fluoride such as sulfur hexafluoride, disulfur decafluoride or trifluoromethylsulfur pentafluoride; selenium hexafluoride; an optionally halogenated silane such as tetramethylsilane; a low molecular weight hydrocarbon (e.g. containing up to 7 carbon atoms), for example an alkane such as methane, ethane, a propane, a butane or a pentane, a cycloalkane such as cyclobutane or cyclopentane, an alkene such as propene or a butene, or an alkyne such as acetylene; an ether; a ketone; an ester; a halogenated low molecular weight hydrocarbon (e.g. containing up to 7 carbon atoms); or a mixture of any of the foregoing. Halogenated hydrocarbon gases can show extended longevity, and thus are preferred for some applications. Representative gases of this group include decafluorobutane, octafluorocyclobutane, decafluoroisobutane, octafluoropropane, octafluorocyclopropane, dodecafluoropentane, decafluorocyclopentane, decafluoroisopentane, perfluoropexane, perfluorocyclohexane, perfluoroisohexane, sulfur hexafluoride, and perfluorooctaines, perfluorononanes; perfluorodecanes, optionally brominated.

Attachment of targeting ligands to lipophilic bubbles can be accomplished via chemical crosslinking agents in accordance with standard protein-polymer or protein-lipid attachment methods (e.g., via carbodiimide (EDC) or thiopropionate (SPDP)). To improve targeting efficiency, large gas-filled bubbles can be coupled to a targeting ligand using a flexible spacer arm, such as a branched or linear synthetic polymer (U.S. Pat. No. 6,245,318). A targeting ligand can be attached to the porous inorganic particles by coating, adsorbing, layering, or reacting the outside surface of the particle with the targeting ligand (U.S. Pat. No. 6,254,852).

Fluorescence Imaging

Non-invasive imaging methods can also comprise detection of a fluorescent label. A drug comprising a lipophilic component (therapeutic agent, diagnostic agent, vector, or drug carrier) can be labeled with any one of a variety of lipophilic dyes that are suitable for in vivo imaging. Representative labels include but are not limited to carbocyanine and aminostyryl dyes, preferably long chain dialkyl carbocyanines (e.g., DiI, DiO, and DiD available from Molecular Probes Inc. of Eugene, Oreg., United States of America) and dialkylaminostyryl dyes. Lipophilic fluorescent labels can be incorporated using methods known to one of skill in the art. For example VYBRANT™ cell labeling solutions are effective for labeling of cultured cells of other lipophilic components (Molecular Probes Inc. of Eugene, Oreg., United States of America).

A fluorescent label can also comprise sulfonated cyanine dyes, including Cy5.5 and Cy5 (available from Amersham of Arlington Heights, Ill., United States of America), IRD41 and IRD700 (available from Li-Cor, Inc. of Lincoln, Nebr.), NIR-1 (available from Dejindo of Kumamoto, Japan), and LaJolla Blue.

In addition, a fluorescent label can comprise an organic chelate derived from lanthanide ions, for example fluorescent chelates of terbium and europium (U.S. Pat. No. 5,928,627). Such labels can be conjugated or covalently linked to a drug as disclosed therein.

For in vivo detection of a fluorescent label, an image is created using emission and absorbance spectra that are appropriate for the particular label used. The image can be visualized, for example, by diffuse optical spectroscopy. Additional methods and imaging systems are described in U.S. Pat. Nos. 5,865,754; 6,083,486; and 6,246,901, among other places.

Radioimmunoguided System® (RIGS)

Another preferred application of the antibody fragments is in the Radioimmunoguided System®. This technique, also known as the RIGS® System involves the intravenous administration of a radiolabeled monoclonal antibody or its fragment prior to surgery. After allowing for tumor uptake and blood clearance of radioactivity, the patient is taken to the operating room where surgical exploration is effected with the aid of a hand-held gamma activity probe, e.g., Neoprobe®1000. This helps the surgeon identify the tumor metastases and improve the complications of excision. The RIGS® system is advantageous because it allows for the detection of tumors not otherwise detectable by visual inspection and/or palpation. See, O'Dwyer et al, Arch. Surg., 121:1 391-1394 (1986). This technique is described in detail in Hinkle et al, Antibody, Immunoconjugates and Radiopharmaceuticals, 4:(3)339-358 (1991) (citing numerous references describing this technique). This reference also discloses the use of this technique with the CC49 monoclonal antibody itself. This technique is particularly useful for cancers of the colon, breast, pancreas, and ovaries.

In some embodiments, the antibody fragments of the presently disclosed subject matter are employed for in vivo imaging of tumors, wherein a composition of the presently disclosed subject matter that has been labeled with an imaging moiety such as a radio-opaque agent, a radioisotope, or other imaging agent is administered to a subject, and the presence and location of the detectibly-labeled composition in the subject is assayed. This imaging technique can be useful in the staging and treatment of malignancies. In some embodiments, an antibody is labeled with any moiety that is detectable in situ in a subject, for example by nuclear magnetic resonance, radiology, or other detection methods known in the art.

As such, the presently disclosed subject matter also provides methods for detecting tumors in subjects. In some embodiments, the presently disclosed methods comprise (a) administering to the subject a composition comprising the antibody fragment of the presently disclosed subject matter conjugated to a detectable label; and (b) detecting the detectable label to thereby detect the tumor.

Methods for Predicting the Recurrence and/or Progression of Cancer in a Subject

In some embodiments, the presently disclosed subject matter also provides methods for predicting the recurrence of cancer in a subject. In some embodiments, the methods comprise (a) isolating a biological sample comprising cells from a subject with a cancer; (b) contacting the biological sample with an antibody fragment of the presently disclosed subject matter; and (c) identifying in the biological sample one or more cells that bind to the antibody fragment of the presently disclosed subject matter, whereby the recurrence of a cancer is predicted in the subject. With respect to these methods, the identification of cells that bind to the antibody fragment of the presently disclosed subject matter can be indicative of a recurrence of a subject's cancer when the subject had previously been negative for such circulating cells. In some embodiments, the presence of cells that bind to the one or more of the antibody fragments of the presently disclosed subject matter indicates that the subject is at enhanced risk of metastatic disease relative to a subject that is negative for such cells.

Methods for Prognosing Progression of Cancer

The presently disclosed subject matter also provides methods for prognosing progression of a cancer in subjects. In some embodiments, the methods comprise isolating a biological sample comprising cells from a subject with a cancer; contacting the biological sample with the antibody fragment of the presently disclosed subject matter under conditions sufficient for the diabody to bind to an epitope present on a tumor and/or a cancer cell, if present, in the biological sample; and identifying in the biological sample one or more cells that bind to the antibody fragment, whereby progression of a cancer is prognosed in the subject. In some embodiments, the biological sample comprises a blood sample, a lymph sample, or a fraction thereof. In some embodiments, the cancer is an adenocarcinoma or colon cancer.

As used herein, the phrase "prognosing progression of a cancer" refers to evaluating indicia of a cancer disease at a given time point and comparing the same to the indicia of the cancer disease taken at an earlier time point, wherein the comparison is indicative of a progression of the cancer in the subject. In some embodiments, progression of the cancer comprises metastasis of the cancer in the subject.

Other Uses

The antibodies of the presently disclosed subject matter can also be employed in various assay methods, such as but not limited to competitive binding assays, direct and indirect sandwich assays, and immunoprecipitation assays (see e.g., Zola, 1987; Harlow & Lane, 1988).

The antibodies of the presently disclosed subject matter also are useful as affinity purification agents. In this process, one or more antibodies are immobilized on a suitable support (such as, but not limited to a Sephadex resin or filter paper) using methods well known in the art. See e.g., Harlow & Lane, 1988.

Making Antibody Fragments

Also disclosed are methods of making antibody fragments, such as diabodies, tribodies, tetrabodies, or mixtures thereof, comprising: (a) culturing an isolated cell comprising a vector comprising a nucleic acid sequence encoding the antibody fragment as disclosed herein, under conditions such that said antibody fragment is expressed; and (b) recovering said antibody fragment from the cell.

As disclosed herein, the antibody fragments disclosed herein can be made by a variety of methods. Importantly, a VH and VL domain are present, and they are linked together. The VH and VL domains can comprise SEQ ID NOS 10 and 11, for example Having generally described the invention, the same will be more readily understood by reference to the following examples, which are provided by way of illustration and are not intended as limiting.

Without further description, it is believed that one of ordinary skill in the art can, using the preceding description and the following illustrative examples, make and utilize the alterations detected in the present invention and practice the claimed methods. The following working examples therefore, specifically point out preferred embodiments of the present invention, and are not to be construed as limiting in any way the remainder of the disclosure.

EXAMPLES

Example 1: Sequences and Purification Methods for Stable, High-Affinity Single-Chain Antibody Fragments that Bind to the Human Adenocarcinoma Marker TAG-72

Protein Sequences for 3E8.scFv and 3E8.scFv.Cys

3E8.scFv
(SEQ ID NO: 1)
MKYLLPTAAAGLLLLAAQPAMAAHHHHHHGSSGGGENLYFQGSSGDIVMT
QSPDSLAVSLGERATINCKSSQSVLYSSNNKNYLAWYQQKPGQPPKLLIY
WASTRESGVPDRFSGSGSGTDFTLTISSLQAEDVAVYYCQQYYSYPLTFG
GGTKVEIKLSADDAKKDAAKKDDAKKDDAKKDLQVQLVQSGAEVKKPGAS
VKVSCKASGYTFTDHAIHWVRQAPGQRLEWMGYFSPGNDDFKYSQKFQGR
VTITADKSASTAYMELSSLRSEDTAVYYCARSWIMQYWGQGTLVTVSS

3E8.scFv.Cys
(SEQ ID NO: 2)
MKYLLPTAAAGLLLLAAQPAMAAHHHHHHGSSGGGENLYFQGSSGDIVMT
QSPDSLAVSLGERATINCKSSQSVLYSSNNKNYLAWYQQKPGQPPKLLIY
WASTRESGVPDRFSGSGSGTDFTLTISSLQAEDVAVYYCQQYYSYPLTFG
GGTKVEIKLSADDAKKDAAKKDDAKKDDAKKDLQVQLVQSGAEVKKPGAS
VKVSCKASGYTFTDHAIHWVRQAPGQRLEWMGYFSPGNDDFKYSQKFQGR
VTITADKSASTAYMELSSLRSEDTAVYYCARSWIMQYWGQGTLVTVSSC

The sequences include the pelB leader sequence for periplasmic export with the signal peptidase sequence underlined (MKYLLPTAAAGLLLLAAQPAMA (SEQ ID NO: 3)), a cleavable 6×His tag with TEV protease recognition sequence (AHHHHHHGSSGGGENLYFQ (SEQ ID NO: 4)), a short linker (GSSG (SEQ ID NO: 5)), the VL domain derived from 3E8, a linker known as 205C (LSADDAKKDAAKKDDAKKDDAKKDL (SEQ ID NO: 6)) derived from a CC49 scFv, and the VH domain derived from 3E8.

DNA Sequences for Expression of 3E8. scFv and 3E8. scFv. Cys

3E8.scFv
(SEQ ID NO: 7)
5'CATATGAAATATCTGTTACCTACTGCTGCTGCGGGCCTGCTATTATTA
GCGGCACAACCAGCAATGGCGGCGCATCATCATCATCATCATGGGTCCTC
GGGCGGTGGCGAAAATCTGTATTTTCAGGGTAGCAGCGGCGATATTGTGA
TGACCCAGAGCCCGGATAGTTTGGCCGTTAGCCTGGGCGAACGTGCGACG
ATTAATTGCAAGAGCAGCCAGAGCGTGCTTTACAGCAGCAACAATAAGAA
TTACCTGGCGTGGTATCAGCAAAAACCCGGCCAGCCGCCGAAACTTTTGA
TTTATTGGGCGAGCACCCGTGAAAGCGGCGTGCCGGATCGTTTCTCGGGC
TCAGGCAGCGGGACCGATTTTACGCTGACCATCAGCAGCCTTCAGGCGGA
GGATGTCGCGGTGTACTACTGCCAGCAGTATTACAGCTATCCGTTGACCT
TTGGGGGAGGCACCAAAGTGGAGATCAAACTGAGCGCGGATGATGCTAAG
AAAGATGCGGCGAAGAAGGACGATGCGAAAAAAGACGACGCAAAAAAGGA
TCTGCAGGTGCAGCTGGTGCAGTCGGGTGCGGAAGTGAAGAAACCTGGGG
CGTCGGTGAAAGTGAGCTGCAAAGCGAGCGGCTATACCTTTACCGATCAT
GCGATTCATTGGGTGCGTCAAGCGCCAGGCCAGCGTCTGGAATGGATGGG
CTATTTTTCCCCAGGCAACGATGATTTCAAGTATTCCCAGAAGTTCCAAG
GGCGCGTGACCATTACCGCCGATAAAAGCGCAAGCACCGCGTATATGGAG
CTGTCCAGCCTGCGTAGCGAAGATACAGCGGTTTACTATTGCGCACGGAG
CTGGATTATGCAATACTGGGGCCAGGGCACCCTGGTGACCGTGAGCAGCT
AAGGATCC3'

3E8.scFv.Cys
(SEQ ID NO: 8)
5'CATATGAAATATCTGTTACCTACTGCTGCTGCGGGCCTGCTATTATTA
GCGGCACAACCAGCAATGGCGGCGCATCATCATCATCATCATGGGTCCTC
GGGCGGTGGCGAAAATCTGTATTTTCAGGGTAGCAGCGGCGATATTGTGA
TGACCCAGAGCCCGGATAGTTTGGCCGTTAGCCTGGGCGAACGTGCGACG
ATTAATTGCAAGAGCAGCCAGAGCGTGCTTTACAGCAGCAACAATAAGAA
TTACCTGGCGTGGTATCAGCAAAAACCCGGCCAGCCGCCGAAACTTTTGA
TTTATTGGGCGAGCACCCGTGAAAGCGGCGTGCCGGATCGTTTCTCGGGC
TCAGGCAGCGGGACCGATTTTACGCTGACCATCAGCAGCCTTCAGGCGGA
GGATGTCGCGGTGTACTACTGCCAGCAGTATTACAGCTATCCGTTGACCT
TTGGGGGAGGCACCAAAGTGGAGATCAAACTGAGCGCGGATGATGCTAAG
AAAGATGCGGCGAAGAAGGACGATGCGAAAAAAGACGACGCAAAAAAGGA
TCTGCAGGTGCAGCTGGTGCAGTCGGGTGCGGAAGTGAAGAAACCTGGGG
CGTCGGTGAAAGTGAGCTGCAAAGCGAGCGGCTATACCTTTACCGATCAT
GCGATTCATTGGGTGCGTCAAGCGCCAGGCCAGCGTCTGGAATGGATGGG
CTATTTTTCCCCAGGCAACGATGATTTCAAGTATTCCCAGAAGTTCCAAG
GGCGCGTGACCATTACCGCCGATAAAAGCGCAAGCACCGCGTATATGGAG

-continued
CTGTCCAGCCTGCGTAGCGAAGATACAGCGGTTTACTATTGCGCACGGAG

CTGGATTATGCAATACTGGGGCCAGGGCACCCTGGTGACCGTGAGCAGCT

GTTAAGGATCC3'

This sequence has been subcloned into plasmids pCOLD IV (under the control of the cspA promoter) and pHLIC (under the control of the T7 promoter), in both cases between NdeI and BamHI restriction sites. Expression of 3E8.scFv from pCOLD IV and pHLIC and 3E8.scFv.Cys from pCOLD IV and pHLIC has been demonstrated.

Method of Expression and Purification

Both scFvs are produced from bacterial expression with export to the periplasm, IMAC purification, and proteolytic cleavage of the 6×His tag (FIG. 1).

Expression from pCOLD IV: The ampicillin resistant plasmids (3E8.scFv or 3E8.scFv.Cys) were transformed into DH10B for cold-shock expression. Cells were grown at 37° C. in 2×YT shake flasks to OD600=0.7-1.0. At mid-log phase the flasks were plunged into ice water for 10 minutes. Next, the cells were induced with 0.2 mM IPTG and moved to 4° C. for 20 minutes. After cold shock, the flasks were returned to the shaker and grown for ~16 hours at 16° C.

Expression from pHLIC: The ampicillin resistant plasmids were transformed into DE3 (successful expression achieved in BL21 (DE3), C41 (DE3), C43 (DE3), C43 (DE3) pLysS, T7 Express LysY (NEB), T7 Express LysY/Iq (NEB)) bacterial strains for cold-shock expression. Cells were grown at 37° C. in 2×YT shake flasks to OD600=~1.0-1.5. At late-log phase the flasks were plunged into ice water for 10 minutes. Next, the cells were induced with 0.05 mM IPTG and moved to 4° C. for 20 minutes. After cold shock, the flasks were returned to the shaker and grown for about 16 hours at 16° C.

Purification from Bacteria: Cells were harvested by centrifugation at 8,000 g and resuspended (40 mL/1 L culture) in 30 mM Tris·HCl, 20% sucrose, pH 8. Spheroplasts from 1 L of culture were isolated by adding 30 mg lysozyme, 0.05 mg RNase (Pierce), 100 U DNase (Fisher), and 2 mM MgCl2. The suspension is mixed at 4° C. with a magnetic stir bar for 20 minutes before dilution with 80 mL of ice cold water. The diluted sample is stirred for another 30 minutes at 4° C. before centrifugation at 8,000 g. The antibody fragment is purified from the supernatant by immobilized metal affinity chromatography (IMAC). For each liter of culture, 1 mL of 50% Ni-NTA agarose (Thermo) is added to a pre-fitted column (Bio-Rad). Next, the supernatant is passed through the resin and the bound material is washed (50 mM Tris·HCl, 300 mM NaCl, 20 mM imidazole pH 8.0) before elution (50 mM Tris·HCl, 300 mM NaCl, 250 mM imidazole pH 8.0). The 6×His-TEV-3E8.scFv is digested overnight with 6×His-tagged TEV protease with 1 mM DTT. After cleavage, the sample is dialyzed into 50 mM potassium phosphate, 300 mM NaCl, pH 8. The hexahistidine tag and 6×His-fused TEV protease are removed by a second Ni-NTA column. Concentration and purity are assayed by SDS-PAGE and absorbance at 280 nm.

Purification of 3E8.scFv.Cys: The C-terminal cysteine variant is purified identically to 3E8.scFv with the following modifications. (1) All solutions are supplemented with 1 mM TCEP to prevent undesired disulfide bonds between the C-terminal cysteine residues. (2) The 3E8.scFv.Cys co-purifies with a degradation product. To remove this protein, the 6×His-3E8.scFv.Cys was dialyzed into 50 mM acetate pH 5, 15 mM NaCl, 1 mM TCEP and ion exchange chromatography was performed with Resource S column (GE). The protein is eluted with increasing concentrations of NaCl in 50 mM acetate pH 5, 1 mM TCEP. The full-length scFv elutes at 450 mM NaCl and is easily separated from the contaminant which elutes at 600 mM NaCl. Post elution, the desired fractions are dialyzed into 50 mM potassium phosphate, 300 mM NaCl, pH 8 and TEV digested overnight. The 6×His-tag and TEV protease are removed by a second Ni-NTA column.

Addition of Extra Alanine Following the Signal Peptidase Cleavage Site

Initial purification of 3E8.scFv resulted in poor yields with the majority of the antibody fragment residing in the insoluble fraction. It appeared that the amino acid sequence of SEQ ID NO: 1 was a poor substrate for signal peptidase. To improve the cleavage reaction, a second alanine codon was inserted into the DNA sequence. The resulting protein product, MKYLLPTAAAGLLLLAAQ-PAMAAHHHHHHGSSGGGENLYFQGSSGDIV (SEQ ID NO: 9), increases the fraction of soluble (membrane-liberated) antibody fragment.

Optimization of Periplasm Extraction

The purification methodology reported here is the result of empirical optimization that significantly deviates from standard periplasmic purification protocols. The most common approach is to resuspend the cells in TSE buffer (Tris-Sucrose-EDTA). In this protocol, after incubation in TSE, the cells are harvested from the osmotic fraction by centrifugation and resuspended in water supplemented with magnesium. After incubation in water, the sample is centrifuged to separate the periplasmic fraction and the cells. The periplasmic fraction is then dialyzed to remove residual EDTA before IMAC. This process generates excessively large volumes that complicate dialysis steps, or require concentration. In addition, some or all protein may be lost to the osmotic fraction. 3E8.scFv was purified in poor yield when executing this standard protocol.

To improve yield, the purification procedure was optimized and the amount of protein recovered from the osmotic and periplasmic fractions was quantified. It is thought that dialysis is necessary to remove residual EDTA before applying the protein to the Ni-NTA column. In fact, when the dialysis step was omitted, the amount of recovered protein decreased in both the osmotic and periplasmic fraction. It was then questioned whether or not the EDTA itself was necessary. EDTA chelates divalent cations resulting in membrane destabilization. When the procedure was repeated in the absence of EDTA, the dialysis step was no longer necessary. Here, an increased recovery in the osmotic fraction was obtained, but minimal material was isolated from the periplasmic fraction. Next, it was hypothesized that lysozyme could destabilize the membrane in lieu of EDTA. Once again, no dialysis was required and increased yields were seen in both fractions. Finally, the lysozyme protocol was modified by omitting the centrifugation and harvest step between Tris-Sucrose and water. This generated pure protein in the highest yield.

Effect of Expression Vessel

Early preparations of periplasmic scFvs resulted in slow growth and significant cell lysis. To deter cellular lysing, the protocol was switched from aeration baffled flasks to standard Erlenmeyer flasks and decreased shaking from 200 rpm to 100 rpm. These adaptions led to higher O.D.600 values with minimal lysing.

Physical Properties

Oligomeric State

The CC49 scFv from Pavlinkova (1999) was reported to be a mixture of monomer and dimer. The quaternary structure of both scFvs by gel filtration chromatography was assayed. 3E8.scFv has a molecular weight of 28 kDa, and elutes as a single species with a calculated molecular weight of 25 kDa. The engineered scFv of 3E8 is monomeric with no visible dimer or higher oligomer formation. CC49.scFv elutes earlier with a calculated molecular weight of 31 kDa, which suggests some degree of unfolding/expansion. Additionally, the CC49 chromatogram has a smaller second peak with calculated molecular mass of 64 kDa, corresponding to some dimer formation. The CC49.scFv exists as a heterogeneous mixture, and may be slightly expanded or unfolded.

Stability

The full-length IgG and both scFvs were assayed for stability to aggregation by Differential Static Light Scattering (DSLS) and High-Throughput Thermal Scanning (HTTS). DSLS measures the diffraction of 600 nm light with increasing temperature. As proteins unfold and aggregate, the precipitation products diffract light leading to high O.D.600 values. CC49.scFv undergoes a single cooperative transition with Tagg=54.0° C. (temperature where half the protein is aggregated). A similar transition is seen in 3E8.scFv, but the engineered variant is ~12° C. more stable (66.0° C.). The full-length antibody, 3E8.IgG is an additional 21° C. more stable than its truncated relative. These results show that the 3E8.scFv is significantly more stable to aggregation than CC49.scFv, but more aggregation-prone than the corresponding IgG.

A second technique for measuring protein stability is based on hydrophobic dye binding of thermally denatured intermediates (HTTS). Here, it is reported that THTTS values (temperature where half the protein is unfolded) that are highly concordant to the Tagg values shown for both scFvs (55.4° C.—CC49.scFv and 66.0° C.—3E8.scFv). The full-length IgG exhibits two unfolding transitions—one at 66.2° C., and a second at 83.6° C. The first transition overlaps the unfolding event seen for 3E8.scFv and can describe the unfolding variable domains. The second transition therefore corresponds to the unfolding of constant domains. These data taken together with the DSLS values, show that the increased stability of the constant domains prevent the IgG from aggregating, but both the scFv of 3E8 and the IgG are inactivated at 66° C. Therefore a single chain variable fragment has been successfully produced that is dramatically more stable than CC49.scFv and equal to the stability of 3E8.IgG.

Binding

Fluorescence Dot Blot

Figure 7:
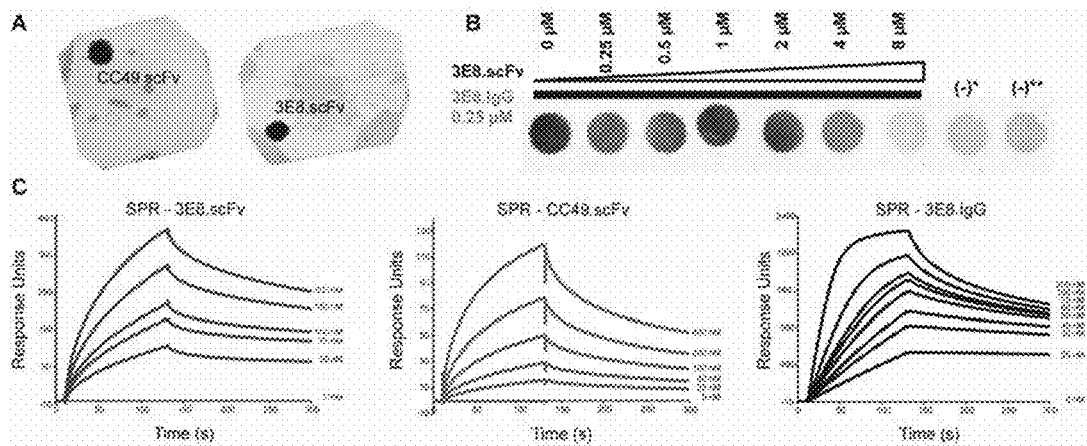
FIG. 7 shows antibody and fragment binding. A. Dot blot assay shows that both CC49.scFv and 3E8.scFv bind BSM (sialyl-Tn), but not BSA. B. Inhibition assay with fluorescent IgG and nonlabeled scFv shows that the scFv binds ~16-fold less strongly than the bivalent IgG. (−)* was performed with 0.25 µM IgG with no BSM. (−)** was performed using free fluorescein in the absence of antibody. C. SPR sensograms for each variant.

Bovine submaxillary mucin is positive for the TAG-72 epitope, sialyl-Tn. To qualitatively assay binding, BSM was spotted on a nitrocellulose membrane and then blocked with bovine serum albumin (BSA). The antibodies and fragments were labeled nonspecifically at lysines with the NHS-ester of fluorescein, and then were added to the dot blots. After gentle washing the samples were imaged using a Typhoon phosphorimager. The darker circle indicates a positive result for sialyl-Tn binding and was seen for both CC49.scFv and our engineered variant, 3E8.scFv (FIG. 7A).

Competition Dot Blot

Figure 3A:
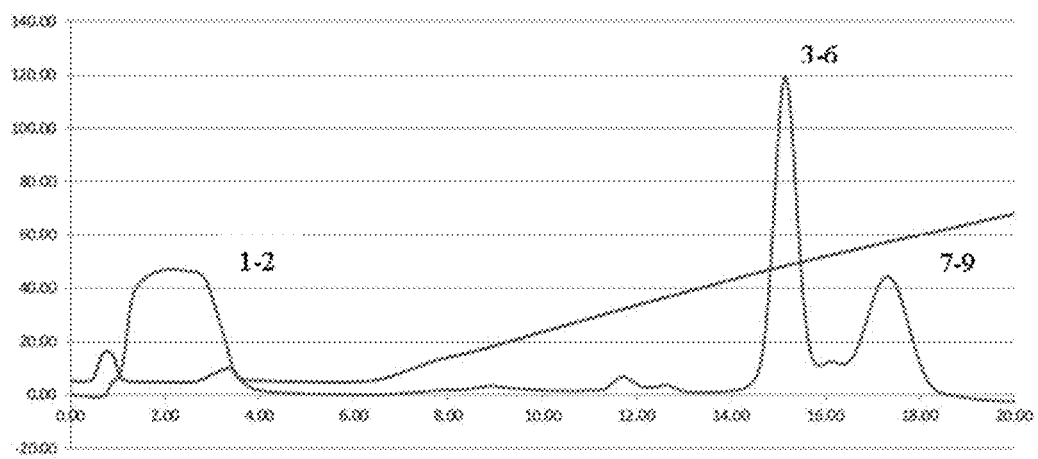
FIGS. 3A and 3B show purification of 3E8.scFv.Cys from its proteolytic fragment using cation exchange chromatography. The two species eluted from a Resource S column at 450 and 600 mM NaCl, with the authentic product eluting first. This was confirmed by SDS-PAGE. Lanes 1 and 12 are USB ladder, Lane 2: 3E8.scFv.Cys prior to ion exchange chromatography, Lanes 3-4: Fractions 1 and 2, Lanes 5-8: Fractions 3-6, Lanes 9-11: Fractions 7-9. The desired product is indicated with an asterisk.
Figure 3B:
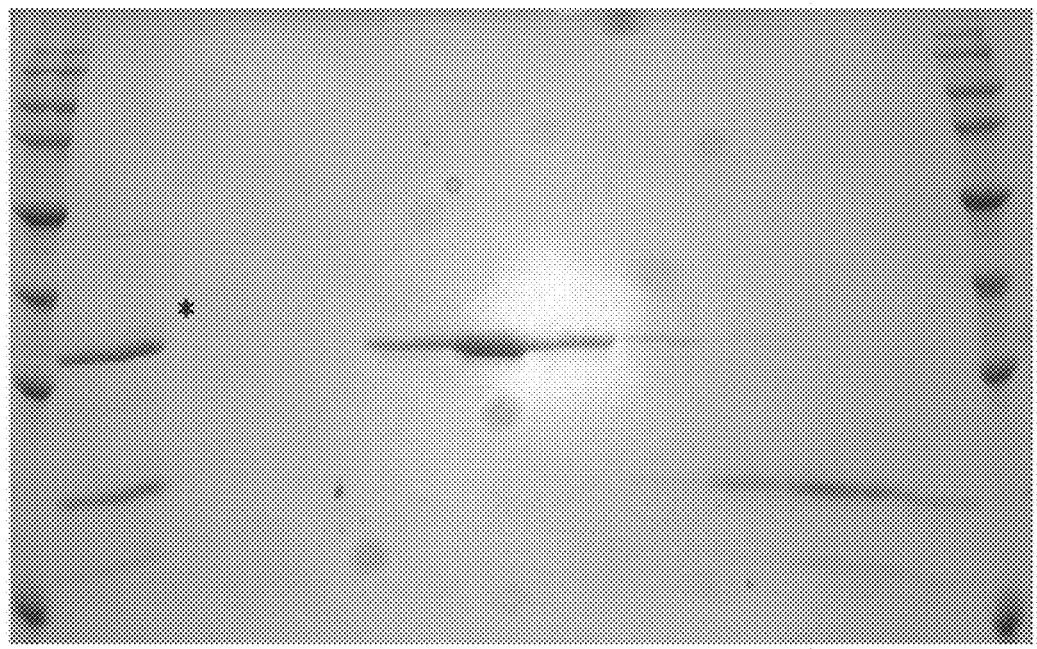
Figure 8:
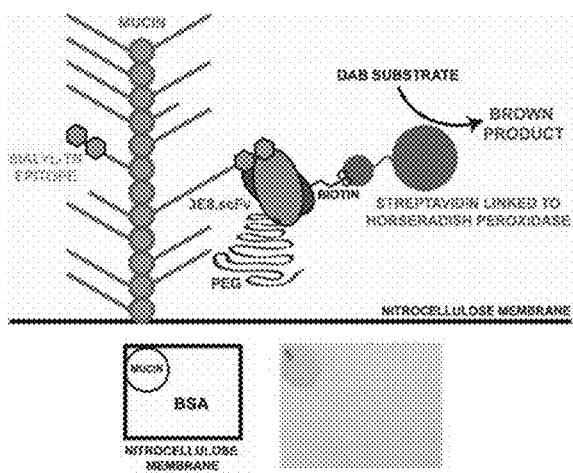
FIG. 8 shows dot blot assay using horseradish peroxidase as the reporter. Here, the scFv specifically binds the section of nitrocellulose that was blotted with mucin containing the TAG-72 epitope. The brown color is the result of the chemical reaction catalyzed by horseradish peroxidase, which is linked to the scFv by the biotin-streptavidin interaction.

A similar dot blot experiment was performed using constant concentrations of BSM and fluorescein-labeled 3E8 IgG. The assays were performed with increasing concentrations of unlabeled 3E8.scFv. If the scFv and IgG recognize the same epitope in BSM, and the scFv affinity is comparable to the IgG, one should see diminished fluorescence at increasing concentrations of scFv. Two negative controls were performed in parallel. First, the nitrocellulose membrane was prepared using only BSA to show that the antibodies do not bind nitrocellulose or BSA nonspecifically. Second, free fluorescein was added to the BSM dots to show that the interaction is not mediated by the fluorophore. As shown in FIG. 7B, 3E8 IgG binds strongly until ~2 µM competing 3E8.scFv. By 4 µM scFv about half of the IgG is displaced and by 8 µM the dot blot resembles the negative control. This analysis estimates that 3E8.scFv binds approximately 16-fold weaker than 3E8.IgG and both bind the same epitope. The slight loss in affinity is expected since the native IgG is bivalent versus the monovalent scFv.

Surface Plasmon Resonance

To further confirm the binding data, surface plasmon resonance was performed on 3E8 IgG, CC49.scFv, and 3E8.scFv (FIG. 7C). The 3E8 IgG has been previously reported to bind the sialyl-Tn epitope with a KD of ~1 nM (Yoon 2006). The commercially prepared 3E8 IgG was assayed by SPR and determined the affinity to be similar, 4±2 nM. CC49.scFv binds in the mid-nanomolar range with a dissociation constant of 30±8 nM. 3E8.scFv bound 2-fold more tightly than CC49.scFv and only 4-fold more weakly than the bivalent IgG. At 16±4 nM, 3E8.scFv binds better than clinically tested CC49 IgG and scFv variants of CC49, and has more desirable biophysical properties than full-length antibodies.

IHC

3E8.scFv was nonspecifically biotinylated (using NHS-biotin) to investigate its candidacy for immunohistochemistry (IHC), and to validate its ability to bind sialyl-Tn in human tissue. Generally, antibody was incubated with tissue before gentle washing and addition of a biotinylated secondary antibody. Next, streptavidin-linked horseradish peroxidase (HRPO) was added to the tissue in the presence of 3,3'-diaminobenzidine tetrahydrochloride (DAB). The oxidation of DAB results in a chromogenic product that stains localized tissue. The fragment was directly labeled with biotin at surface lysines. Before staining human tissue, a nitrocellulose dot blot analogous to FIG. 8A was performed successfully.

Figure 9:
FIG. 9 shows immunohistochemical staining of human colon cancer. The scFv intensely stains the extracellular mucin and the intracellular vacuoles containing the TAG-72 epitope.

Diseased colon was obtained from surgical resection and embedded in paraffin before sectioning. The sample was stained with the commercial B72.3 kit (Biocare Medical) and 3E8.scFv. Both samples intensely stained the extracellular mucin, as well as mucin-filled intracellular vesicles (FIG. 9). Nonspecific binding in the two colon specimens tested was not detected.

Paraffin-embedded tissue was cut at 4 µm and sections were placed on positively-charged slides. Slides were then placed at 60° C. for one hour, cooled, deparaffinized and rehydrated through xylene and graded ethanol solutions to water. All slides were quenched for 5 minutes in 3% hydrogen peroxide to block endogenous peroxidase. Antigen retrieval was performed by Heat-Induced Epitope Retrieval (HIER) where slides are incubated in Target Retrieval Solution pH 6 (Dako) for 25 minutes at 96° C. Slides were stained with 5 µM scFv using a Dako Autostainer Immunostaining System at room temperature. Slides were counterstained in Richard-Allan hematoxylin, dehydrated through graded ethanol solution, cleared with xylene and coverslipped.

Conjugation of 3E8.scFv and 3E8.scFv.Cys

NHS-PEG

3E8.scFv was nonspecifically PEGylated at surface lysines using NHS-ester chemistry. A discrete PEG with molecule weight of 1.8 kD (Quanta BioDesign—10910) was reacted with the antibody fragment at 0, 5×, and 20× molar excess. The reaction proceeded in phosphate buffered saline for 1 hour at room temperature before quenching with ethanolamine. Unreacted PEG was removed by dialysis. Conjugation of a deuterated PEG for detection by Raman or IR spectroscopy was also demonstrated.

NHS-Fluorescein

3E8.scFv was nonspecifically labeled with fluorescein at surface lysines using NHS-ester chemistry. A NHS-fluorescein (Pierce—46410) was reacted with the antibody fragment at 20× molar excess. The reaction proceeded in phosphate buffered saline for 2 hour at 4° C. Unreacted fluorophore was removed by dialysis.

NHS-Biotin

3E8.scFv was nonspecifically labeled with biotin at surface lysines using NHS-ester chemistry. A NHS-biotin (Sigma—H1759) was reacted with the antibody fragment at 5× molar excess. The reaction proceeded in phosphate buffered saline for 1 hour at room temperature. Unreacted biotin was removed by dialysis.

Maleimide-PEG

3E8.scFv.Cys was specifically PEGylated at the C-terminal cysteine using maleimide chemistry. A discrete PEG with molecule weight of 2.7 kD (Quanta BioDesign—10931) was reacted with the antibody fragment at 20-fold molar excess. The reaction proceeded in phosphate buffered saline for 1 hour at room temperature. Unreacted PEG was removed by dialysis.

Example 2: Improving Therapeutic Protein Through PEGylation: Cancer Imaging Antibodies A modern cancer-imaging system, radioimmunoguided surgery (RIGS), utilizes radionuclide-labeled antibodies that bind to an epitope present only on certain cancer cells. Studies on the covalent attachment of polyethylene glycol molecules (PEGs) to proteins indicate that PEGylation can improve therapeutic effectiveness. Disclosed herein are the effects of PEGylation (using different types of PEG) with the end-goal of improving 3E8.scFv as a RIGS antibody. Described herein is what PEGs actually do to the protein to which they are attached. Differentiation between two models, PEG-protein interaction: polymer-like beads near the attachment point vs. wrapping around the protein like thread, is examined A model protein (T4 lysozyme, T4L) is used to observe the general behavior of PEGylated proteins and to compare the different types of PEGs. An analysis of the effects of PEGylation with SDS polyacrylamide gel electrophoresis (PAGE) and a lysozyme activity assay is analyzed. Circular dichroism is used to do an in depth analysis to measure folding; gel filtration chromatography to measure size; differential static light-scattering and high-throughput thermal scanning to measure stability; and analytical ultracentrifugation and small-angle x-ray scattering to measure size/shape.

A PEGylation procedure that attaches activated PEGs to T4L or 3E8.scFv has been developed. SDS-PAGE analysis indicates proteins with integer numbers of attached PEGs. The activity of T4L and the binding of 3E8.scFv (PEGylated and unPEGylated) has been assessed using a fluorescence-based activity assay and surface plasmon resonance and immunohistochemistry binding assays, respectively.

The clinical applications of RIGS include that RIGS can be performed during surgery, eliminating hours of pre- and post-operative imaging. Furthermore, one can tune serum half-life of PEGylated proteins by changing the amount of PEGylation. One can also tune half-life of radionuclide to match the half-life of the antibody.

Traditional cancer imaging includes CT and PET scans, and is not very sensitive or specific. Modern cancer imaging uses Radioimmunoguided Surgery (RIGS), which uses radio-labeled antibodies raised against a disaccharide (sialyl-TN) present on tumor-associated glycoprotein (TAG-72) which is present on the surface of many cancer cells. It is very sensitive and very specific. The antibody currently used is CC49. 3E8 is a good binder, and can be modified into a single chain variable fragment (scFv) as disclosed herein.

It has been shown that attaching PEGs to proteins can improve the therapeutic properties of the protein. It can be attached to proteins (like the model protein, called T4L), at lysine residues using NHS-ester chemistry; at cysteine residues using maleimide chemistry. When attached to proteins, PEGs: are non-immunogenic, decrease aggregation and proteolysis, and increase serum half-lives.

PEGs exist as polydisperse mixtures of molecules, discrete (homogenous) molecules (dPEGs from Quanta Biodesign), and linear and branched molecules, as well as neutral and charged molecules. 3E8.scFv is a correctly folded monomer. It is as stable as the binding domain of 3E8.IgG. It has a KD=16.4 nM and binds correctly. PEGylated 3E8.scFv still binds to correct tissue. PEGylated T4L can be PEGylated with integer numbers of PEGs at lysine residues.

Example 3: Design and Biophysical Characterization of a Stabilized Single Chain Variable Antibody Fragment that Binds Tumor Associated Glycoprotein-72

Results

Construction and Purification

Figure 18:
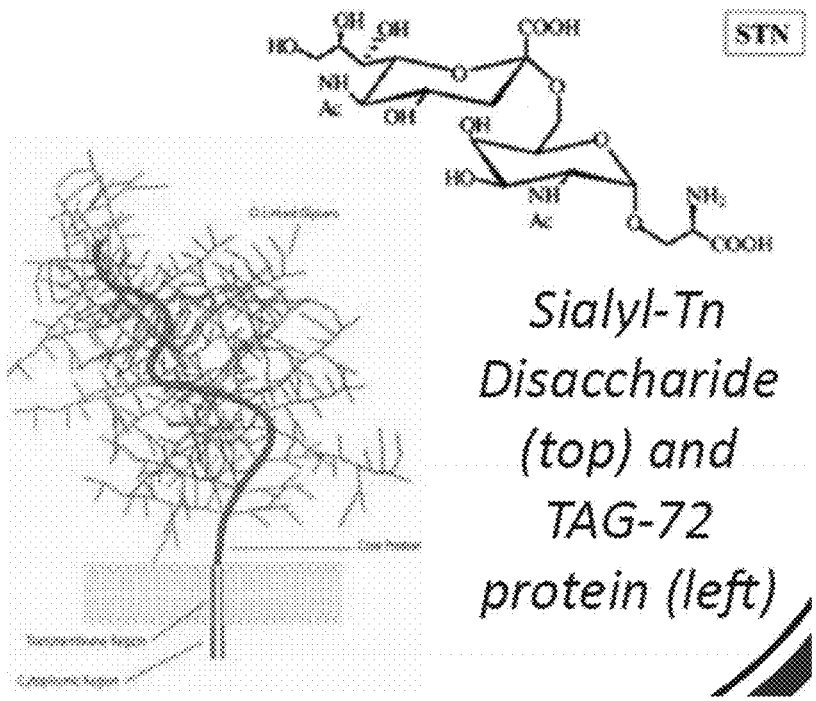
FIG. 18 shows Sialyl-Tn Disaccharide and TAG-72 protein.
Figure 19:
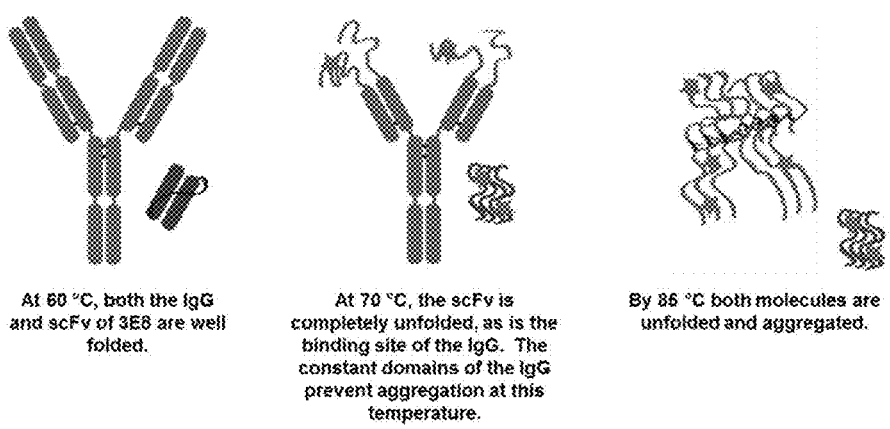
FIG. 19 shows antibody scaffolds depicted in gray bound to antigen (black stars). Also shown is the schematic for the scFv gene. At 60 degrees, both the IgG and scFv of 3E8 are well folded. At 70 degrees, the scFv is completely unfolded, as is the binding site of the IgG. The constant domains of the IgG prevent aggregation of the IgG at this temperature. By 85 degrees, both molecules are unfolded and aggregated.

A detection and imaging agent for adenocarcinomas that express the TAG-72 epitope, sialyl-Tn, was discovered. Disclosed herein is a scFv inspired by 3E8 with carefully chosen linker sequences and improved expression and purification protocols. The variable light domain (VL) is fused to the variable heavy domain (VH) by the 205C linker sequence (Denzin 1991). The scFv is produced as a cleavable hexahistidine fusion and trafficked to the periplasm to enhance folding (FIG. 18). Finally, the full-length gene is subcloned into the pCOLD expression vector to make use of the cold-shock chaperone system (Takara Bio, Inc.).

The scFvs are purified from the periplasmic fraction using lysozyme digestion and osmotic shock. The modified protocol is preferred to standard procedures for its lack of large volumes, removal of dialysis steps, and compatibility with Ni-NTA purification. EDTA has been shown to destabilize the membrane by chelation of divalent calcium, but must be removed before nickel binding (Prachayasittkul 2007). Instead, the outer membrane is disturbed by mild lysozyme digestion. After osmotic shock, the periplasmic fraction can be directly bound to Ni-NTA agarose and purified by standard means. Addition of TEV protease and a second IMAC step yields native single chain variable fragments.

Under cold-shock conditions we are able to express and purify >2 mg $L^{-1}$ of 3E8.scFv in shake flasks, with the ability to increase production through fermentation. We also constructed a literature reported CC49.scFv as a control that under the same conditions yields ~1 mg $L^{-1}$ (Pavlinkova 1999).

Structure

Figure 20:
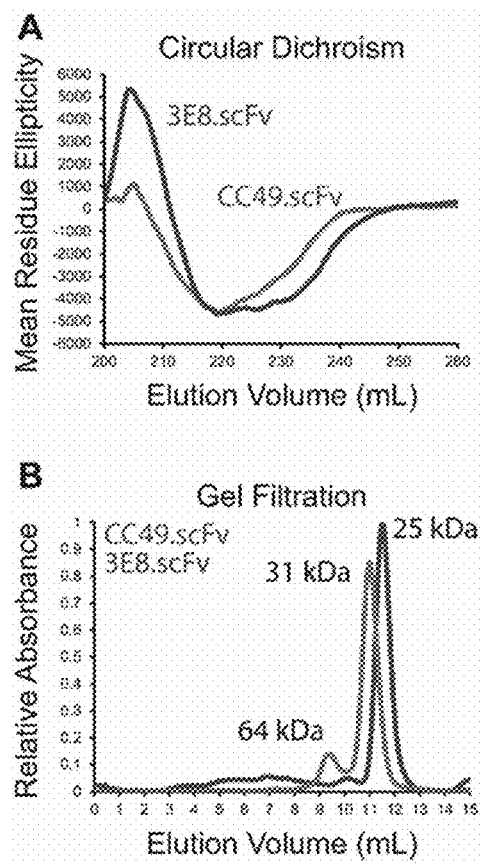
FIG. 20 shows the ScFv structure. A. CD wavelength scan of scFvs is consistent with the immunoglobulin domain fold. B. Gel filtration shows a single monomeric species for 3E8.scFv, but CC49 is slightly expanded and exists as a scFv.
Figure 21:
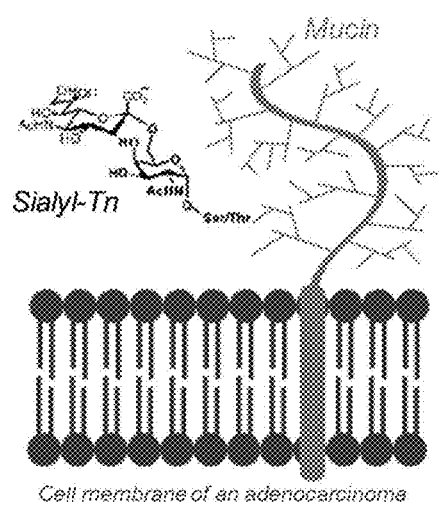
FIG. 21 shows that mucin is a large glycoprotein expressed and secreted from healthy and diseased cells. The mucin of adenocarcinomas has been shown to overexpress the disaccharide, Sialyl-Tn. This epitope is targeted with antibodies and antibody fragments.
Figure 22A:
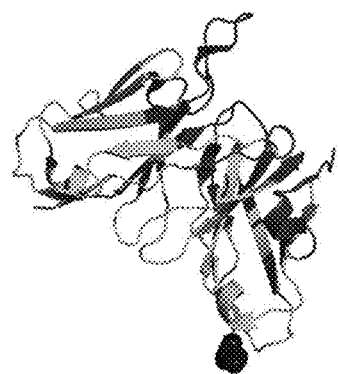
FIGS. 22A and 22B show PEGylation.
Figure 22B:
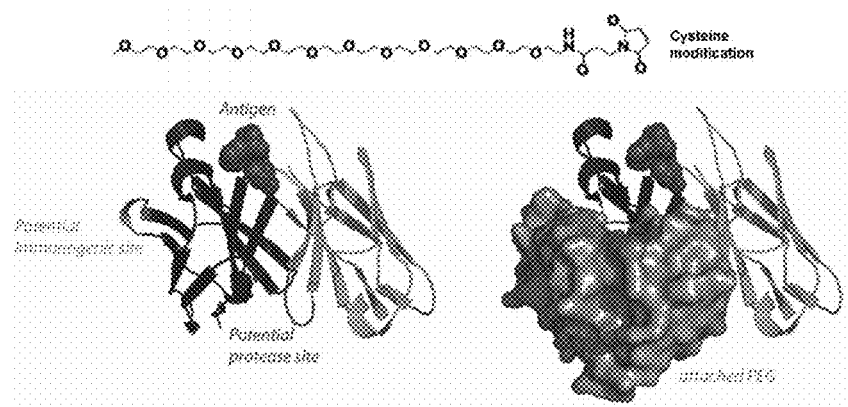

Full-length IgGs consist of four polypeptide chains including two heavy (~50 kDa) and two light (~25 kDa) chains. The two heavy chains interact with each other and with the light chain both through noncovalent contacts and disulfide bonds. Antigen binding is achieved using the variable loops in the N-terminal domains of the heavy and light chains, both of which belong to the immunoglobulin fold. An immunoglobulin fold is comprised of 7-9 antiparallel β-strands (Bork 1994). These secondary structures form two β-sheets with Greek key architecture. To stabilize the VH and VL interaction in scFvs, an amino acid linker is used to connect the C-terminus of the VL domain to the N-terminus of VH domain. To assess the gross structural features of 3E8.scFv and CC49.scFv circular dichroism (CD) (FIG. 20a) was performed. CC49.scFv has the expected minima around 215-220 nm for β-strands. 3E8.scFv has a similar shape spectra, but also exhibits a large positive peak around 205 nm consistent with immunoglobulin domains. The 205C linker is predicted to possess some coiled structure which can lead enhanced signal at 222 nm.

Next the quaternary structure of both scFvs by gel filtration were assayed. 3E8.scFv has a molecular weight of 28 kDa, and elutes as a single species with a calculated molecular weight of 25 kDa (FIG. 20b). The engineered scFv of 3E8 is monomeric with no visible dimer or trimer formation, nor aggregation. CC49.scFv elutes earlier with a calculated molecular weight of 31 kDa, which is 3 kDa greater than the predicted mass which shows some degree of unfolding or expansion.

Binding

Up regulation of metabolic genes in cancer cells leads to an increase in sialyl-Tn disaccharide display on mucin (Kjeldsen 1988). Molecules targeted to this epitope provide a powerful means for distinguishing cancerous and healthy tissue. Bovine submaxillary mucin is positive for the TAG-72 epitope, sialyl-Tn. To qualitatively assay binding, BSM was dotted on a nitrocellulose membrane and then blocked with bovine serum albumin (BSA). The antibodies and fragments were labeled nonspecifically at lysines with fluorescein, and then were added to the dot blots. After gentle washing the samples were imaged using a Typhoon phosphorimager. The darker circle indicates a positive result for sialyl-Tn binding and was seen for both our positive control, CC49.scFv, and our engineered variant, 3E8.scFv (FIG. 7a).

Next, a similar dot blot experiment was performed using constant concentrations of BSM and fluorescently-labeled 3E8.IgG. The assays were performed with increasing concentration of nonlabeled 3E8.scFv. If the scFv and IgG recognize the same epitope in BSM, and the scFv affinity is comparable to the IgG, one should see diminished fluorescence at increasing concentrations of scFv. Two negative controls were performed in parallel. First, the nitrocellulose membrane was prepared using only BSA to show that the antibodies do not bind nitrocellulose or BSA nonspecifically. Second, free fluorescein was added to the BSM dots to show that the interaction is not mediated by the fluorophore. As shown in FIG. 7b, 3E8.IgG binds strongly until ~2 µM competing 3E8.scFv. By 4 µM scFv about half of the IgG is displaced and by 8 µM the dot blot resembles the negative control. This analysis estimates that 3E8.scFv binds approximately 16-fold worse than 3E8.IgG and both bind the same epitope. The slight loss in affinity is expected since the native IgG is bivalent verse the monovalent scFv.

To further confirm the binding data, surface plasmon resonance on 3E8.IgG, CC49.scFv, and 3E8.scFv (FIG. 7c) was determined. The 3E8.IgG has been previously reported to bind the sialyl-Tn epitope with a $K_d$ of ~1 nM[7]. 3E8.IgG was assayed by SPR and it was determined that the affinity to be similar, 4±2 nM. Next the affinity of the scFv of CC49 was measured. CC49.scFv binds in the mid-nanomolar range with a dissociation constant of 30±8 nM. Finally, SPR was conducted on 3E8.scFv and found it to bind 2-fold better than CC49.scFv and only 4-fold weaker than the bivalent IgG. At 16±4 nM, 3E8.scFv binds better than clinically tested CC49.IgG and scFv variants of CC49, and has more desirable biophysical properties than full-length antibodies.

Immunohistochemistry

The single chain variable fragment of 3E8 was nonspecifically biotinylated to investigate its candidacy for immunohistochemistry (IHC), and to validate its ability to bind sialyl-Tn in human tissue. Generally, an antibody is incubated with tissue before gentle washing and addition of a biotinylated secondary antibody. Next, streptavidin-linked horseradish peroxidase (HRPO) is added to the tissue in the presence of 3,3-diaminobenzidine tetrahydrochloride (Dab). The oxidation of Dab results in a chromogenic product that stains localized tissue. Because the scFv lacks the constant domain where the secondary antibody binds, our fragment was directly labeled with biotin at surface lysines. Before staining human tissue, a nitrocellulose dot blot analogous was performed successfully.

Diseased colon was obtained from surgical resection and embedded in paraffin before sectioning. The sample was stained with the commercial B72.3 kit and 3E8.scFv. Both samples intensely stained the extracellular mucin, as well as mucin-filled intracellular vesicles (FIG. 9).

Stability

Figure 6:
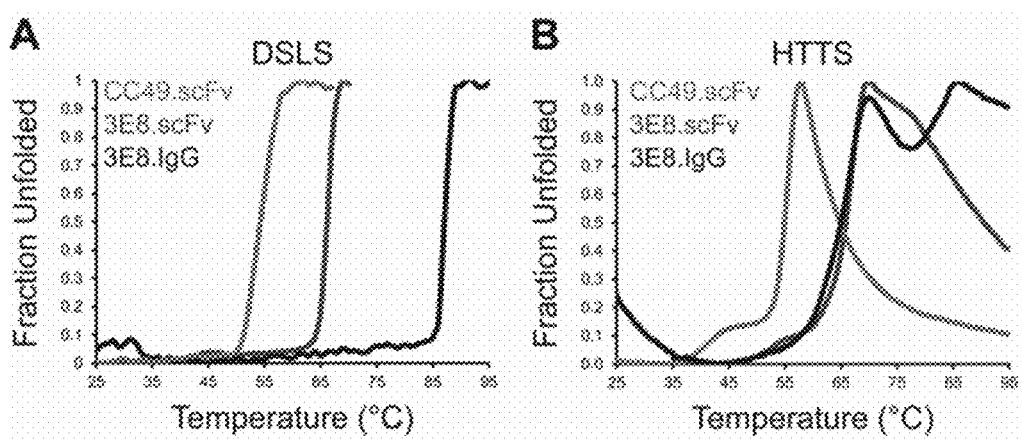
FIG. 6 shows the stability of antibodies and fragments. A. Aggregation propensity is measured with increasing temperature. 3E8.scFv is intermediate in stability between the less stable CC49.scFv and the more stable 3E8.IgG. B. HTTS shows similar results to those reported by DSLS, with a second unfolding transition for 3E8.IgG. The binding domains of 3E8.scFv and 3E8.IgG both unfold at 66° C.

Engineering a single chain variable fragment with enhanced stability and aggregation resistance was the goal. The full-length IgG and both scFvs were assayed for stability by Differential Static Light Scattering (DSLS) (Senisterra 2009) and High-Throughput Thermal Scanning (HTTS) (Lavinder 2009). DSLS measures the diffraction of 600 nm light with increasing temperature (FIG. 6a). As proteins unfold and aggregate, the precipitation products diffract light leading to high $O.D._{600}$ values. CC49.scFv undergoes a single cooperative transition with $T_{agg}$=54.0° C. (temperature where half the protein is aggregated). A similar transition is seen in 3E8.scFv, but the engineered variant is ~12° C. more stable (66.0° C.). The full-length antibody, 3E8.IgG is an additional 21° C. more stable than its truncated relative. These results alone show that the 3E8.scFv is significantly more stable than CC49.scFv.

A second technique for measuring protein stability is based on hydrophobic dye binding of thermally denatured intermediates (HTTS). Here, it is shown that $T_{HTTS}$ values (temperature where half the protein is unfolded) that are highly concordant to the $T_{agg}$ values shown for both scFvs (55.4° C.-CC49.scFv and 66.0° C.-3E8.IgG). The full-length IgG exhibits two unfolding transitions—one at 66.2° C., and a second at 83.6° C. (FIG. 6b). The first transition overlaps the unfolding event seen for 3E8.scFv and can describe the unfolding variable domains. The second transition therefore corresponds to the unfolding of constant domains. This data taken together with the DSLS values, show that the increased stability of the constant domains prevent the IgG from aggregating, but both the scFv of 3E8 and the IgG are inactivated at 66° C. Therefore a single chain variable fragment that is dramatically more stable than CC49.scFv and equal to the stability of 3E8.IgG has been produced.

Materials and Methods

Design and Construction

The scFv genes were designed as VL-linker-VH fusions. The genes encode the PelB leader sequence for periplasmic trafficking, a hexahistidine tag for purification, and the recognition site for Tobacco Etch Virus (TEV) protease to remove the purification tag. The full-length DNA genes were ordered from Geneviz, Inc. (South Plainfield, N.J.) and subcloned into pCOLD IV (Takara Bio, Japan). The monoclonal antibody, 3E8.IgG was received as a gift from Enlyton, Ltd. (Columbus, Ohio).

Expression and Purification

The ampicillin resistant plasmids were transformed into DH1013 for cold-shock expression. Cells were grown at 37° C. in 2×YT shake flasks to O.D.$_{600}$=~0.7. At mid-log phase the flasks were plunged into ice water for 10 minutes. Next, the cells were induced with 0.3 mM IPTG and moved to 4° C. for 30 minutes. After cold shock, the flasks were returned to the shaker and grown for ~16 hours at 16° C.

Cells were harvested by centrifugation at 8000 g and resuspended (40 mL/1 L culture) in 30 mM Tris·HCl, 20% sucrose, pH 8. Spheroplasts from 1 L of culture were generated by adding 30 mg lysozyme, 0.05 mg RNase (Pierce), 100 Units DNase (Fisher), and 1.5 mM MgCl$_2$. The suspension was mixed at 4° C. with a magnetic stir bar for 30 minutes before dilution with 160 mL of ice cold water. The diluted sample was stirred for another 30 minutes at 4° C. before centrifugation at 8000 g. The supernatant was decanted and prepared for Ni-NTA binding by adding 4 mL of 0.5 M imidazole and 1 mL of 50% Ni-NTA agarose (Qiagen). After 1 hour of nickel binding at 4° C. the periplasmic fraction was poured into a prefritted column (Bio-Rad) and washed (50 mM Tris·HCl, 300 mM NaCl, 20 mM imidazole pH 8.0) before elution (50 mM Tris·HCl, 300 mM NaCl, 250 mM imidazole pH 8.0). The 6×His-TEV-scFvs were digested overnight with 6×His-TEV protease with 5 mM DTT. After cleavage, the sample was dialyzed into 50 mM potassium phosphate, 300 mM NaCl, pH 8. The hexahistidine tag and 6×His-TEV were removed by a second Ni-NTA column. Protein concentration and purity were assayed by SDS-PAGE and absorbance at 280 nm.

Circular Dichroism

Spectra were recorded on a Jasco J-185 spectrometer at 10 µM protein in 10 mM HEPES, 150 mM NaCl, 3.4 µM EDTA, 0.005% surfactant P20 (GE Healthcare). Wavelength scans were collected in triplicate from 190 to 275 nm with 2 second integration at 100 nm min$^{-1}$ scanning speed. Data collected with HT voltage greater than 600 V were discarded.

Gel Filtration

Size-exclusion chromatography was performed on a GE Pharmacia AKTA Purifier. Antibody fragments were injected at 10 µM and eluted from a Superdex 75 10/300 column (GE Amersham) with 50 mM Tris·HCl, 100 mM NaCl, pH 8 at 0.4 mL min$^{-1}$. Molecular weights for scFvs were calculated based on fits from known standards: aprotinin (6.5 kDa-14.6 mL), cytochrome c (12.5 kDa-12.9 mL), carbonic anhydrase (29.0 kDa-11.21 mL), and bovine serum albumin (66.5 kDa-9.2 mL).

Stability

The stability of the full-length antibody and scFvs were determined by High-Throughput Thermal Scanning (HTTS). Here, 5 µM protein was incubated with 5×SYPRO Orange dye (Invitrogen). The melts were assayed using a Bio-Rad C1000 thermal cycler with a ramp rate of 1° C. min$^{-1}$ at 0.2° C. intervals. The data were exported to Microsoft Excel 2010. The $T_{HTTS's}$ were calculated as the temperature with the maximum slope as determined from a 5° C. window around each point.

The temperature of aggregation was assayed by Differential Static Light Scattering (DSLS) using the absorbance feature of the Jasco J-185 spectrometer at 10 µM protein in 10 mM HEPES, 150 mM NaCl, 3.4 µM EDTA, 0.005% surfactant P20 (GE Healthcare). Data were collected in 1° C. steps with 6 second temperature equilibration, 1° C. min ramping, and 2 second integration. All melts were exported to Microsoft Excel 2010. The TAGus were calculated as the temperature with the maximum slope as determined from a 5° C. window around each point.

Labeling

The antibody and fragments were nonspecifically labeled at surface lysines with a molar excess of NHS-fluorescein (53209-Pierce). Labeling was confirmed with an Olis DM-45P fluorimeter. ScFv was labeled at surface exposed lysines with a 3 molar excess of NHS-biotin (H1759-Sigma). Excess labeling reagent was removed by dialysis into 50 mM potassium phosphate, 300 mM NaCl, pH 8.

Binding

Qualitative binding to sialyl-Tn was assayed by dot-blotting. First, 2 µL of 5 mg mL bovine submaxillary mucin (M3895-Sigma) was spotted on a nitrocellulose membrane. The membrane was allowed to dry overnight before blocking with 5 mg mL$^{-1}$ BSA. After overnight incubation, excess BSA was removed by washing before addition of fluorescein-labeled scFvs. The scFvs were incubated for 3 hours at room temperature before washing. Fluorescence was observed using a Typhoon phosphorimager with 488 nm excitation.

The epitope binding of the 3E8.scFv was assayed for its ability to inhibit 3E8.IgG binding. Here, 0.25 µM labeled 3E8.IgG competed with increasing concentrations of non-labeled 3E8.scFv (0 to 8 µM). The loss of fluorescence was observed using the Typhoon phosphorimager with 488 nm excitation.

The binding parameters were evaluated using surface plasmon resonance (SPR). BSM was immobilized on a CMS dextran sensor chip using the GE Pharmacia amine coupling kit (BR-1000-50). Scouting conditions were 200 µg mL$^{-1}$ BSM in 100 mM sodium acetate, pH 4 for channel 2, and 10 µg mL$^{-1}$ BSA in 100 mM sodium acetate, pH 4 for channel 1. The immobilization protocol continued until 700 RU were obtained. Binding was measured as 2-1. Antibody and fragments were dialyzed into 10 mM HEPES, 150 mM NaCl, 3.4 µM EDTA, 0.005% surfactant P20 (GE Healthcare) and were assayed from 0-400 nM. Samples were bound for 120 seconds at 10 µL min$^{-1}$ and dissociation was measured for 180 seconds. The CMS chip was regenerated between trials with 6 M guanidine and 200 mM acetic acid with no loss in activity. The average binding parameters were evaluated using the BIAevaluation software.

Immunohistochemistry

Paraffin-embedded tissue was cut at 4 µm and sections were placed on positively-charged slides. Slides were then placed at 60° C. for one hour, cooled, deparaffinized and rehydrated through xylene and graded ethanol solutions to water. All slides were quenched for 5 minutes in 3% hydrogen peroxide to block endogenous peroxidase. Antigen retrieval was performed by Heat-Induced Epitope Retrieval (HIER) where slides are incubated in Target Retrieval Solution pH 6 (Dako) for 25 minutes at 96° C. Slides were stained with 5 µM scFv using a Dako Autostainer Immunostaining System at room temperature. Slides were counterstained in Richard Allen hematoxylin, dehydrated through graded ethanol solution, cleared with xylene, and coverslipped.

Example 4: Single Chain Variable Fragments of 3E8, PEGylation, and Conjugation to 3E8cys.scFv Design and Cloning of Antibody Fragments A first-generation single-chain variable fragment (scFv) based on the affinity-optimized, humanized antibody, 3E8

(Yoon 2006). The parent antibody has been reported to bind to the sialyl-Tn epitope that is found in the tumor-associated glycoprotein-72 (TAG-72) with a dissociation constant in the range of 5-10 nM (Thor 1986; Thor 1987; Muraro 1988; Colcher 1988). scFv fragments are monomeric and dimeric fusions, respectively, of the binding domains of the antibody, and have molecular weights in the range of 25 and 50 kD, respectively (Bird 1988; Kortt 2001). In contrast to full-length IgGs and Fab fragments, these smaller fragments can be expressed in bacteria (Sandhu 1992; Pini 2000).

The variable domains of 3E8 were connected by the 205C linker with the following orientation: VL-205C-VH Denzin, 1991). The sequence was appended with the PelB leader sequence to direct the protein to the periplasm of E. coli, a hexahistidine tag for purification, and TEV protease site for subsequent removal of the hexahistidine tag. The full-length open reading frame was cloned into the pHLIC plasmid for overexpression (Durani 2012). A second construct, 3E8cys.scFv, was generated by PCR of the parent construct with mutagenic primers. This variant places a single cysteine at the C-terminus of 3E8.scFv to allow site-specific PEGylation via maleimide chemistry. Both constructs were confirmed by DNA sequencing.

Expression and Purification of Antibody Fragments

Figure 4:
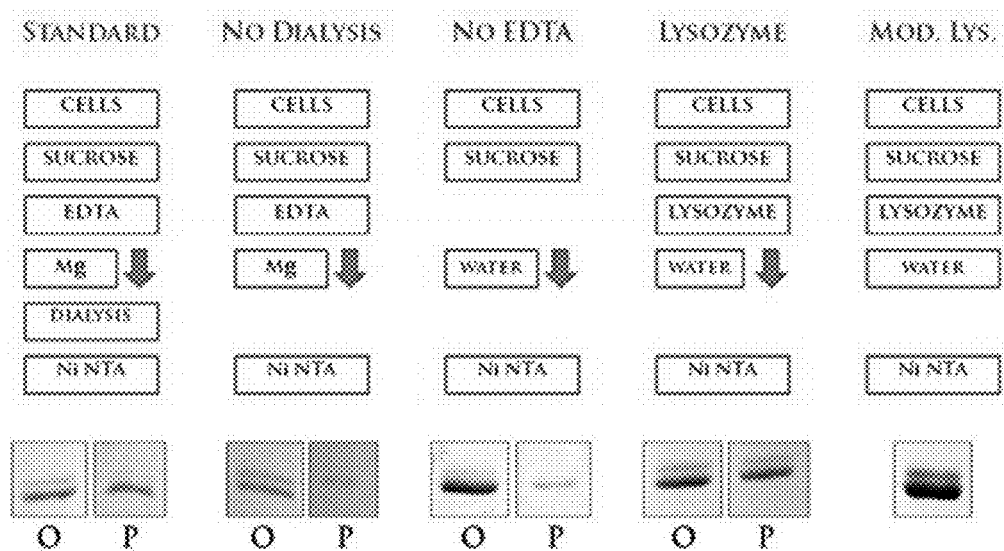
FIG. 4 shows optimization of periplasm extraction. The osmotic (0) and periplasmic (P) fractions are compared across nine purification methods. The modified lysozyme procedure yielded the best results. The faint band above the desired product is scFv with PelB leader sequence. When digested with TEV protease, both protein bands resolve to a single species. All samples purified are 3E8.scFv from pCOLD IV in DH10B.
Figure 5:
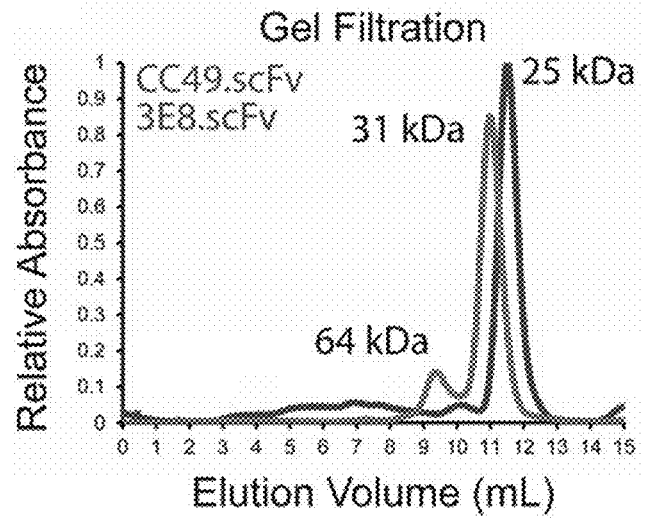
FIG. 5 shows gel filtration of antibody fragments. CC49.scFv is a heterogeneous sample that contains both monomer and dimer. Additionally, the fragment elutes as a slightly larger protein than its calculated molecular weight, showing some degree of unfolding or expansion. The 3E8.scFv elutes as a single species with molecular weight corresponding to a well folded monomer.

The constructs were transformed into C43(DE3) *Escherichia coli* for overexpression under the T7 promoter (Miroux 1996). Cultures were grown at 37° C. to $OD_{600}=1.0$ before cold shock and induction with 0.05 mM IPTG. The cells continued to express protein overnight at 16° C. The next morning, the cells were harvested, resuspended, and lysed by an Avestin Emulsiflex. The soluble fraction was recovered by centrifugation and purified by immobilized metal affinity chromatography (IMAC). The hexahistidine tags were cleaved by TEV protease and further purified by a second IMAC step (FIG. 20), to better than 90% purity. An additional ion exchange column was required to purify 3E8cys.scFv to near homogeneity due to the presence of what appears to be a proteolytic contaminant. Here, a Resource S cation exchange column separated the desired product from the 17 kD contaminant (FIG. 4). Under these conditions ~2 mg $L^{-1}$ of each scFv variant was purified, and have generated >10 mg from a single purification of material from 6 L of media in shake flasks.

Selection of PEGs and Conjugation

Figure 23:
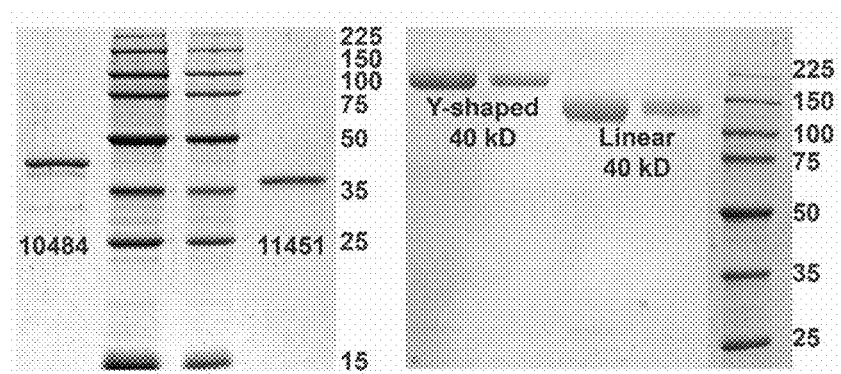
FIG. 23 shows crude modeling of 3E8.scFv reveals four lysines within the CDRs responsible for antigen binding.

PEGylation has been shown to increase the serum half-lives of antibody fragments by raising the hydrodynamic radius of the molecule, decreasing kidney filtration (Chen 2011; Veronese 2008). In addition, PEGylation has been reported to decrease proteolysis, immunogenicity, and aggregation. PEGs can be attached to proteins at lysines and cysteines via NHS-ester or maleimide activated PEGs, respectively. Crude modeling of 3E8.scFv reveals four lysines within the CDRs responsible for antigen binding (FIG. 23A). 3E8cys.scFv was engineered, which adds a C-terminal cysteine. This cysteine is expected to be the only free thiol within the antibody fragment, allowing for the site-specifically PEGylation of the scFv at a site distal to the antigen interaction surface.

Figure 24:
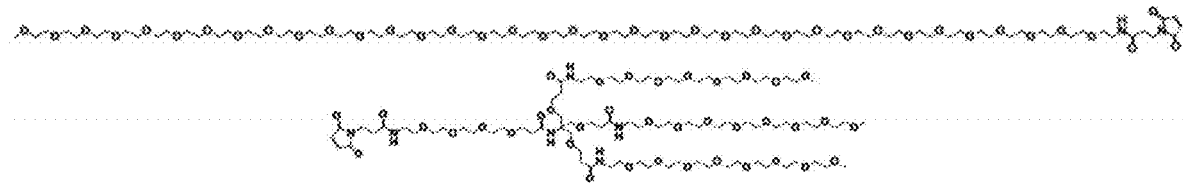
FIG. 24 shows PEGylated 3E8cys.scFv. Modified antibody fragments are shown on an SDS-PAGE gel. The 40 kD samples are loaded at 2× and 1× concentrations. PEG polymers do not strongly interact with SDS; therefore, their apparent masses are anomalous by SDS-PAGE compared to protein ladders. A linear and branched 1.8 kD PEG are shown.

PEGylate 3E8cys.scFv was chose for PEGylation with Quanta BioDesign's 10484 and 11451 PEGs. Both PEGs are discrete—meaning each molecule has an exact number of repeating polymer units (($-CH_2-CH_2-O)_n$), as opposed to polydisperse PEGs which contain a distribution of numbers of monomeric units. The first PEG (10484) has a molecular weight of exactly 8,323.78 Da. It is a neutral PEG with three large arms each containing three further branches. The second PEG (11451) has a molecular weight of exactly 4,473.17 Da. It has three branches each terminating in a negatively charged carboxylic acid. To explore the effects of even larger PEGs linear and Y-shaped (branched) 40 kD PEGs were obtained from JenKem Technology USA. These large PEGs are polydisperse, but the polydispersity index for these molecules is 1.03, meaning that the PEG molecules have masses tightly distributed around 40,000 Da. All PEGs were activated with maleimide functional groups (FIG. 24 and Table 1).

TABLE 1

| | Mass (kD) | Type | Shape | Charge |
|---|---|---|---|---|
| 10484 | 8.3 | discrete | multiple branches | neutral |
| 11451 | 4.5 | discrete | branched | −3 |
| 40-L | ~40 | polydisperse | linear | neutral |
| 40-Y | ~40 | polydisperse | branched (Y-shaped) | neutral |

The protein samples were dialyzed into phosphate buffered saline (PBS) with 1 mM TCEP to keep the C-terminal cysteines reduced for PEGylation. The reactions proceeded to near completion overnight in the presence of ~50-fold molar excess PEG. Unreacted PEG and unmodified 3E8cys.scFv were removed by ion exchange chromatography followed by dialysis into PBS. Between 150-350 μg of each compound was generated.

Binding of 3E8.scFv and PEGylated Antibody Fragments

The purified antibody fragments were analyzed for binding to immobilized bovine submaxillary mucin (BSM), which is positive for the Sialyl-Tn epitope, by surface plasmon resonance (SPR) (God 2000). From this data, the rate of association ($k_a$), rate of dissociation ($k_d$), and the equilibrium dissociation constant ($K_D$) can be determined.

The scFv of 3E8 binds the Sialyl-Tn epitope with low nanomolar affinity (12 nM). In fact, the scFv binds nearly as well as the bivalent IgG (4 nM). The three non-PEGylated constructs all bind the antigen better than clinically investigated CC49 IgG (~30 nM)[15]. 3E8cys.scFv shows slightly lower apparent binding affinity (3-fold higher $K_D$), but on par with CC49. The binding of 3E8cys.scFv is slightly improved when PEGylated with 10484 and 11451; when PEGylated with the larger 40 kD PEGs, the binding is unperturbed.

Figure 25:
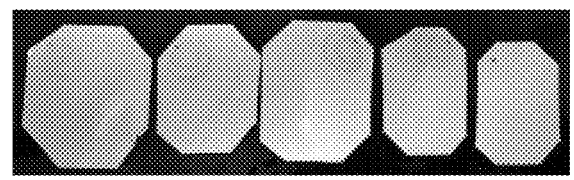
FIG. 25 shows replicates of 3E8cys.scFv+Y-40 kD binding to TAG-72 immobilized on nitrocellulose paper. The antigen was spotted on the corner of the paper indicated by pencil mark. Far right is the negative control, where all experimental steps were performed, but the paper was incubated with buffer in place of antibody fragment.
Figure 26:
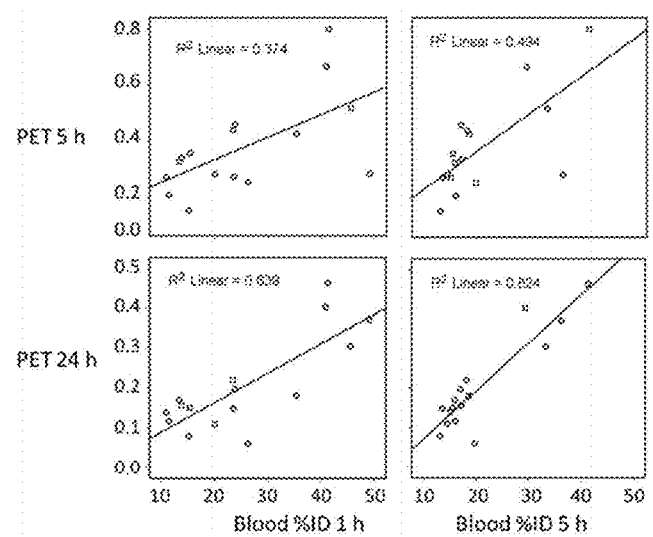
FIG. 26 shows correlation between serum half-lives and microPET/CT imaging. Blood radioactivity (% ID) of each individual mouse is plotted against its normalized tumor intensity in PET imaging. Upper panel, microPET/CT imaging at 5 h; bottom panel, microPET/CT imaging at 24 h. 5 and 24h are the appropriate time points for a $^{123}$I-SPECT/CT radiopharmaceutical.

In addition, binding of these molecules has been validated by dot blots against bovine submaxillary mucin (FIG. 25). Here, nitrocellulose paper is spotted with mucin (TAG-72 positive) and blocked with BSA. The proteins are labeled with biotin for binding to streptavidin-horseradish peroxidase (HRP), and HRP development chemistry. A brown color indicates localization of the antibody fragment to TAG-72.

3E8.scFv's ability to target cancerous tissue by immunohistochemical (IHC) staining of colon tissue has been shown. Here, resected tissue was acquired from a patient with advanced colon cancer. The paraffin-embedded tissue was cut at 4 μm and sections were placed on positively-charged slides. 3E8.scFv was nonspecifically labeled at lysines with NHS-biotin and applied to the tissue with a Dako Immunostaining System. Next, streptavidin-linked HRP is added to the tissue in the presence of DAB. The oxidation of DAB by HRP results in a colored product that stains the localized tissue brown. FIG. 9 shows intense staining of the cancerous extracellular mucin as well as intracellular vesicles containing TAG-72. The scFv of 3E8 targeted the same sites as clinically-used B72.3.

Stability of Antibody Fragments

Antibody fragments with increased stability can have more favorable pharmacokinetic properties and to resist aggregation. The full-length 3E8.IgG and scFvs based on 3E8 and CC49 were assayed for stability by Differential Static Light Scattering (DSLS) and Differential Scanning Fluorimetry (DSF/HTTS) (Senisterra 2009; Lavinder 2009). DSLS measures the scattering of 600 nm light with increasing temperature (FIG. 10a), which is related to aggregation. CC49.scFv undergoes a single cooperative transition with $T_{agg}$=54.0° C. (temperature where half the protein is aggregated). A similar transition is seen in 3E8.scFv, but the engineered variant is ~12° C. more stable (66.0° C.). The full-length antibody, 3E8.IgG is an additional 21° C. more stable to aggregation than its truncated relative. These results alone show that the 3E8.scFv is significantly more stable than CC49.scFv.

Figure 10:
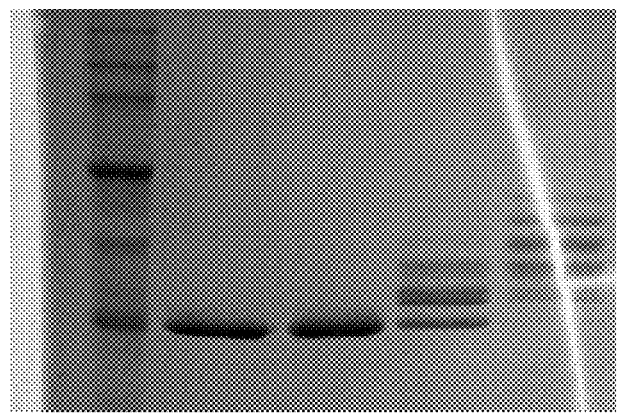
FIG. 10 shows NHS-PEGylation of 3E8.scFv. Lane 1: USB ladder, Lanes 2 and 3: Unmodified antibody fragment, Lane 4: Reaction with 5-fold molar excess of PEG, Lane 5: Reaction with 20-fold molar excess of PEG.
Figure 11:
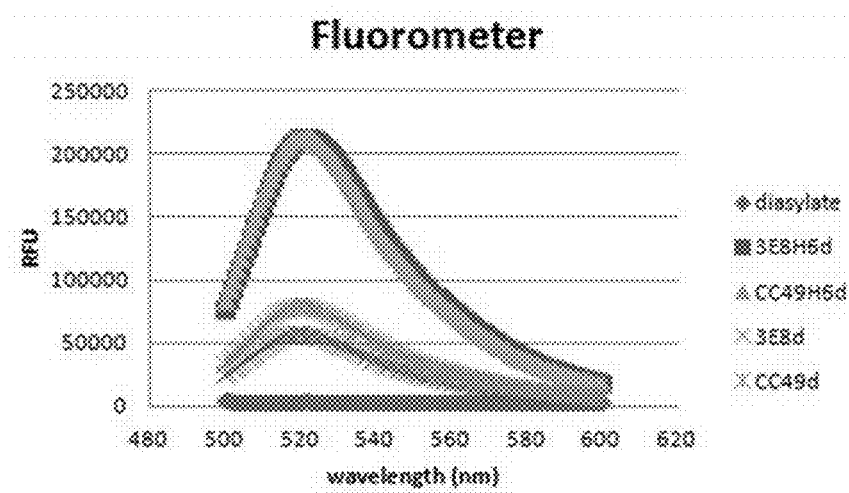
FIG. 11 shows fluorescent labeling of antibody fragments with and without 6×-His tags. The samples with hexahistidine tags (3E8H6d and CC49H6d) generate more intense signals due to increased concentrations of antibody fragment.
Figure 12:
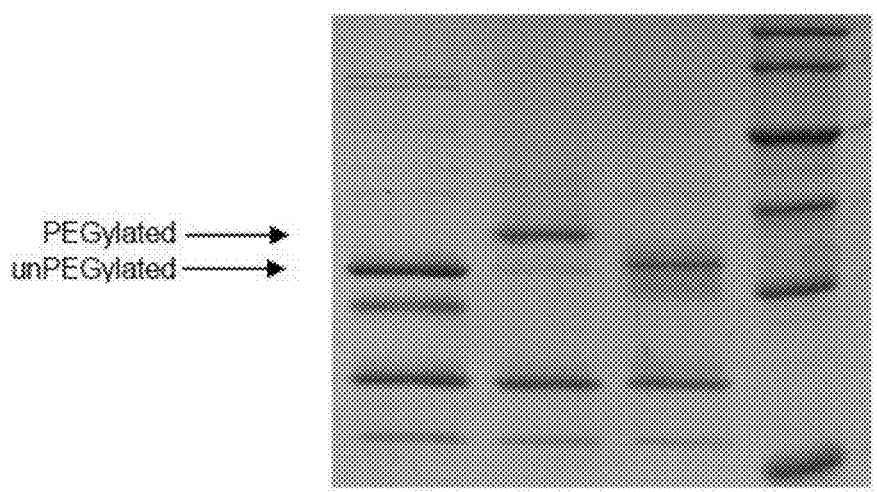
FIG. 12 shows the specific PEGylation of 3E8.scFv.Cys. The antibody fragment was labeled specifically at the C-terminal cysteine residue using maleimide chemistry. The scFv was nearly quantitatively PEGylated. Lane 1: partially purified, reduced 3E8.scFv.Cys, Lane 2: PEGylated 3E8.scFv.Cys. Lane 3: unrelated. Lane 4: ladder.
Figure 13:
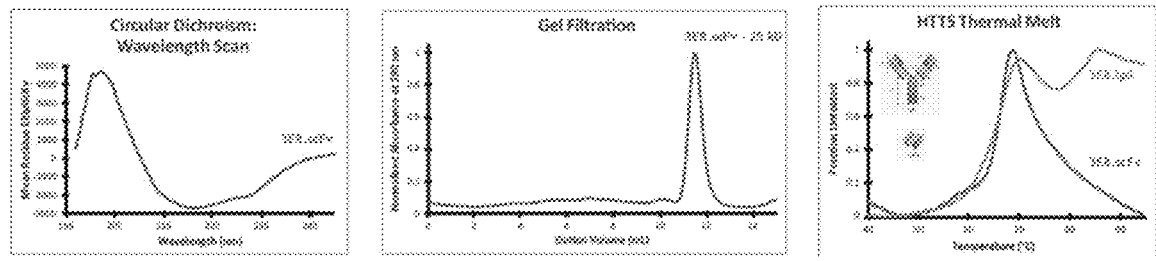
FIG. 13 shows the biophysical characterization of 3E8.scFv.
Figure 14:
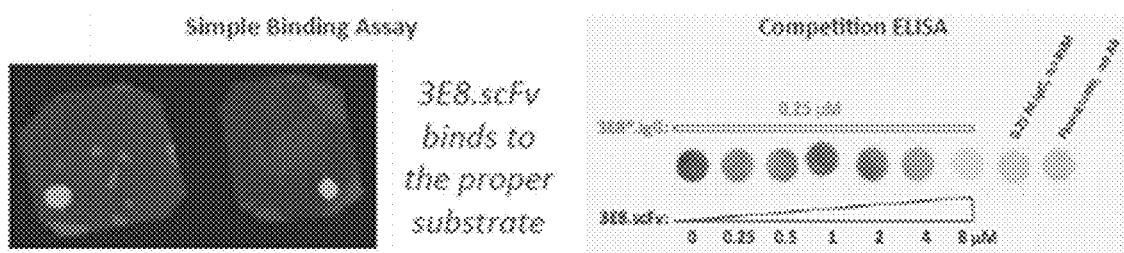
FIG. 14 shows binding studies for 3E8.scFv. An Estimated 50% bound at 4 µM i.e. 3E8.scFv is roughly a 16-fold worse binder than 3E8.IgG (KD=0.65 nM) so it's estimated KD=10.4 nM.
Figure 15:
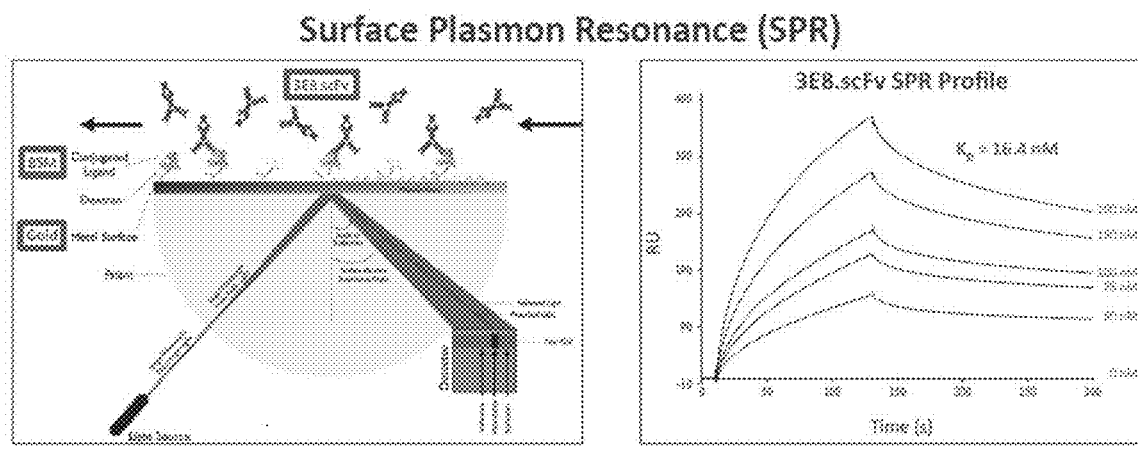
FIG. 15 shows surface plasmon resonance. 3E8.scFv has a measured Kd of 16.4 nM, which indicates very tight binding to the proper substrate.
Figure 16:
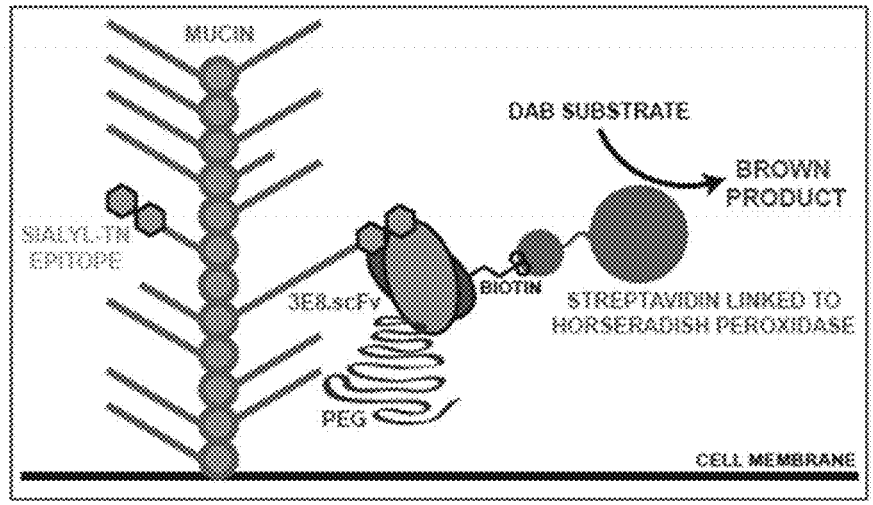
FIG. 16 shows immunohistochemistry. Biotin attached to 3E8.scFv via lysines can be coupled to a chromogenic enzyme complex which produces a brown product. Using this scheme, one can visualize 3E8.scFv bound to its epitope. Histologists can use this technique to analyze surgical specimens to determine the success of surgical procedures.
Figure 17:
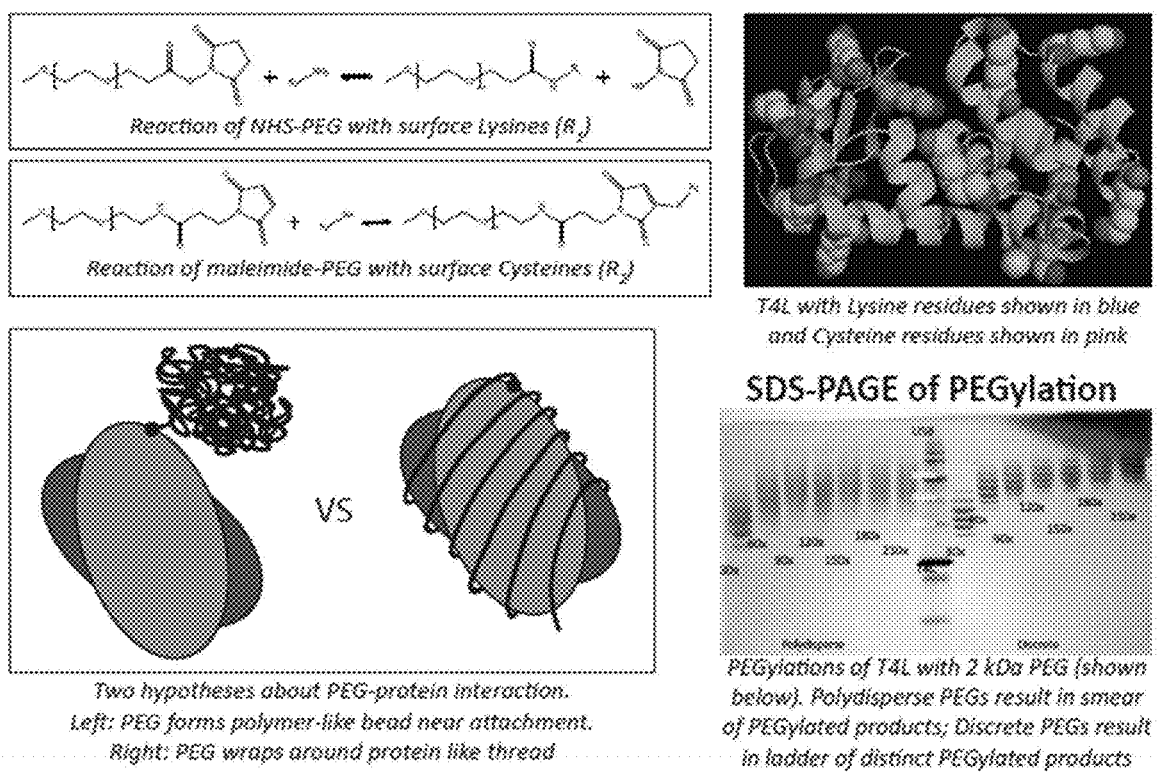
FIG. 17 shows PEGylation results. PEGylations of T4L with 2 kDa PEG is shown. Polydispersed PEGs result in smear of PEGylated products; discrete PEGs result in ladder of distinct PEGylated products.

A second technique for measuring protein stability is based on hydrophobic dye binding of thermally denatured intermediates (DSF/HTTS). Here, we report $T_{DSF}$ values (temperature where half the protein is unfolded) that are highly concordant to the $T_{agg}$ values shown for both scFvs (55.4° C.-CC49.scFv and 66.0° C.-3E8.scFv). The full-length IgG exhibits two unfolding transitions—one at 66.2° C., and a second at 83.6° C. (FIG. 10b). The first transition overlaps the unfolding event seen for 3E8.scFv and therefore likely describes the unfolding variable domains. The second transition would therefore correspond to the unfolding of constant domains. These data taken together with the DSLS values suggest that the increased stability of the constant domains prevent the IgG from aggregating, but both the scFv of 3E8 and the IgG are inactivated at 66° C. Therefore a produced a single chain variable fragment has been produced that is dramatically more stable than CC49.scFv and equal to the functional stability of 3E8.IgG.

Radiolabeling and Pharmacokinetic Properties

The antibody fragments were first radiolabeled using the standard Iodogen method (Bailey 1996; Paus 1982). The free radioactive iodine was separated from labeled antibody by size exclusion chromatography and the fractions with the highest radioactivity were used for animal blood curves.

Radiolabeling

In a typical radiolabeling experiment, ~50-100 µg of protein was transferred to an Iodogen tube (Pierce, Rockford, Ill.) containing 100 µL phosphate buffer (0.1M, pH 7.4) followed by addition of known amounts of $^{125}$INa (Perkin Elmer, Waltham Mass.) or $^{123}$INa (Nordion, Ottowa, Ontario, Canada) in 0.02 M NaOH. An additional 50 µL of phosphate buffer (0.1M, pH 7.4) was then added to the mixture, it was covered with parafilm, and the mixture was incubated at room temperature for 30 to 45 min with occasional swirling. The labeled protein was loaded onto a Sephadex G-25 (PD-10) size-exclusion column and eluted with Phosphate Buffer Saline (PBS) to separate labeled protein from free $^{125/123}$I. Several fractions, containing approximately 10 drops, were collected and the fractions containing the highest radioactivity were collected and pooled in a pre-weighed plastic vial.

The amount of radioactivity was determined using a dose calibrator. The percent yield of radiolabeling was calculated by dividing the total radioactivity of the pooled samples by the amount of radioactivity added to the Iodogen tube. Purity of the samples was determined by Thin Layer Chromatography (TLC) strips (Whatman) eluted with 85% methanol: 15% water mixture. The bound protein did not migrate and unbound iodide moved to the solvent front.

Biodistribution and Pharmacokinetics

CC49 $^{124}$I-Fab'-dPEG molecules were studied using dPEG structures similar or identical to those used in this current study. The same tumors (LS-174T) and same TAG-72 target were used. In the Fab'-dPEG study of 4 different molecules, we measured the blood clearance curves from 1 to 24 hours and whole body microPET/CT imaging. A solid correlation between blood radioactivity at 5 and 24 hours and tumor intensity was found in microPET/CT images at both 5 and 24 hours post administration (FIG. 25). These time points (5 and 24 hours) are appropriate imaging times for the $^{123}$I-SPECT/CT imaging. The mouse blood curves from 1-24 hours were therefore good quantitative indicators of early time tumor uptake and retention. The full tissue biodistribution data are collected at 24 hours.

For evaluating blood clearance, at 0.5, 1, 3, 6, and 24 h, mice were anesthetized with isoflurane, and leg skin was sterilized with a 70% ethanol pad. The saphenous vein was punctured using a 25G syringe needle and 5-10 µL of blood was collected using a capillary tube. The radioactivity of the blood samples was counted using the Wiz II gamma-counter and % ID/g was calculated using the same methods mentioned above. A blood factor of 78 mL/kg was used to calculate % ID for each mouse based on the individual weight of the mouse. Mean % ID was determined for each dose group at each time point.

Mice were sacrificed after the 24 h time point. Organs and tissues were dissected, including heart, lungs, spleen, liver, kidneys, pancreas, gastrointestinal tract (GI), muscle, skin, blood, tail, and carcass. Organs and tissues were then weighed, and radioactivity was counted using a gamma-counter (Perkin Elmer Wizard II, Model 2480, Waltham, Mass.).

It has now been shown that 3E8.scFv can be tuned from very short to very long serum half-lives by modulating the length and type of PEG polymer.

Pharmacokinetics Results

Inclusion of a 30 kD Linear PEG

The unmodified scFv filtered rapidly, and conjugation to 11451 and 10484 did not extend the serum half-lives of the 25 kD antibody fragment. Two 40 kD conjugates were studied that increase the total mass to 65 kD, which approximates the cut-off mass for first-pass renal clearance. These two molecules exhibited dramatic increases in serum residency. In fact, at 24 hours 8 and 18% serum activity were recorded for the linear and Y-shaped PEGs, respectively.

Animal Tumor Model

Animal studies were conducted in compliance with animal protocols approved at The Ohio State University Laboratory Animal Resource. Human colon adenocarcinoma cell line LS-174T was obtained from American Type Culture Collection (Manassas, Va.) and maintained in McCOY's 5A (Invitrogen, Carlsbad, Calif.) supplemented with 10% FBS (Invitrogen) and 1% penicillin and streptomycin (Invitrogen) at 37° C. with 5% $CO_2$. LS-174T cell line was passaged twice a week after being washed in PBS and trypsinization. For each antibody fragment, seven 4-6 week-old female athymic nu/nu mice (Charles River Laboratories, MA) were subcutaneously injected with $6\times10^6$ LS-174T cells in 100 µL of PBS on the right and left flanks. Tumors were allowed to grow for 10 days and five mice with proper sizes on both flanks were recruited in the following studies. Potassium iodine (UPSHER-SMITH, MN) was in ClearH$_2$O Hydro-Gels at 290 mg/L 24 hours prior to injection to block thyroid uptake of metabolized iodine.

Imaging with MicroSPECT/CT $^{123}$I-labeled 3E8 fragment proteins were injected at 1.8 mCi for 3E8cys.scFv+30 kD conjugate, per mouse via tail in 200 µL of PBS. N=4 mice were imaged. Micro-SPECT/CT (Inveon, Siemens Preclinical, Knoxville, Tenn.) imaging of mice was carried out at 5-7 and 20 h post-injection IV Animals were anesthetized using isoflurane inhalation with 5% of dial vaporizer for induction and 1.5-2% for maintenance. The process of microSPECT/CT scanning lasted one hour at the 5 h time point and two hours at the 20 h time point. The difference was due to the decay of the $^{123}$I over one half life (13 h) and therefore much lower count rates at 20 h. The CT scans lasted three minutes. The microSPECT/CT images were reconstructed with the OSEM3D algorithm to try to lower possible artifact due to bladder contents and low localization counts. The discrepancy in threshold was due to a low signal to noise ratio (SNR) and differences in agent performance. These levels gave the best range across all samples to show clearance and background in the surrounding tissues. Large amounts of uptake in the stomach and bladder contents contributed to poor visualization. This however, did not often interfere with the region of interest (ROI) evaluations of the tumors. In all instances, the CT scan was used to assist in the determination of the tumor volume. The fasciae and subcutaneous fat gave enough tissue contrast to separate the xenograft in the CT volumes.

Example 5: Antibody Fragments that Bind TAG-72

Disclosed herein is a series of VH-linker-VL and VL-linker-VH molecules based on the sequence of the 3E8 antibody that binds with high affinity and specificity to the sialyl-Tn epitope found in TAG-72 in adenocarcinomas in humans. The linkers vary from a single glycine residue, to short Gly-Ser containing linkers, to longer repeats of Gly-Ser sequences, to the 205C linker 3E8.scFv. The molecules were all expressed, purified, and characterized as shown herein. Briefly, the same purification scheme as used for 3E8.scFv was initially employed, with IMAC purification of 6×His tagged material, cleavage by TEV protease, and re-purification by IMAC.

The molecules were examined for stability by differential scanning fluorimetry (DSF), for oligomeric state by gel filtration chromatography, and for binding by surface plasmon resonance (SPR). The key finding for this disclosure is that 3E8HL(GGGGS) was found to be nearly oligomerically pure, it was the most stable of the molecules tested, and its affinity for TAG-72 (2.6 nM) is as good as reported for any TAG-72 binder. This is referred to throughout as the 3E8.G$^4$S. Since 3E8.G$^4$S is derived from a humanized antibody (3E8), it is not likely to elicit a human immune response.

It has been demonstrated that 3E8.G$^4$S is useful not only for imaging adenocarcinomas in xenograft mice, but radioiodination of the antibody fragment. Imaging and biodistribution studies show that the molecule is cleared in hours from serum, targets tumor efficiently, and does not accumulate in other organs. Various molecules—B72.3, CC49, huCC49, 3E8—demonstrate the utility of anti-TAG-72 antibodies in cancer diagnosis and imaging. Various antibody fragments, including Fabs, domain-deleted Fabs, diabodies, and scFvs, have been reported based on the previously named antibodies. GMP-like expression as near-process amounts for production of a biologic has been demonstrated from bacteria. 3E8.G$^4$S is therefore an advanced lab prototype.

Sequences, Laboratory Production, and Characterization
Nomenclature

To fully describe an antibody fragment one must include a description of the variable domain orientation (VH-VL or VL-VH), the amino acid linker sequence, other features maintained in the final purified protein product (e.g. a C-terminal cysteine or hexahistidine tag), and the quaternary structure (scFv, diabody, triabody, multimer, etc.). The constructs enclosed in this document are written as 3E8w(X)y.z, where W describes the orientation (LH for VL-VH and HL for VH-VL), X describes the linker sequence, Y explains additional features, and Z reports the major quaternary species. The molecule called 3E8HL(GGGGS) (SEQ ID NO: 32) is referred to herein as the 3E8.G$^4$S.

Cloning

Quaternary Variants:

3E8LH(G).multimer (SEQ ID NOS: 18 and 19), 3E8LH(GG).multimer (SEQ ID NOS: 20 and 21), 3E8LH(GGG).multimer (SEQ ID NOS: 22 and 23), 3E8LH(GGGG), (SEQ ID NOS: 24 and 25), 3E8LH(GSSG), (SEQ ID NOS: 26 and 27), 3E8LH(GGGGS), (SEQ ID NOS: 28 and 29), and 3E8LH(SGGGG), (SEQ ID NOS: 30 and 31) open reading frames were generated from overlapping polymerase chain reactions using 3E8.scFv as the template. Full-length genes were digested with restriction endonucleases NdeI and BamHI before ligation into overexpression vector, pCOLD IV (Takara Bio.). Each DNA clone was verified by analytical restriction endonuclease digest and DNA sequencing at Genewiz Inc. Each variant was subcloned into the T7 expression plasmid, pHLIC. First, the entire gene sequences was digested from pCOLD with NdeI and BamHI. Next, the gene was ligated into pHLIC which had previously been digested with the same restriction endonucleases. Each DNA clone was verified by analytical restriction endonuclease digest and DNA sequencing at Genewiz Inc.

In addition, two other quaternary variants were constructed, 3E8HL(GGGGS) (SEQ ID NO: 32) and 3E8HL(GGGGS)his6 (SEQ ID NO: 12). The desired protein sequences were reverse translated into nucleotide sequences and appended with restriction sites CATATG and GGATCC for subcloning into pCOLD IV and pHLIC at NdeI and BamHI, respectively. The open reading frames were synthesized by Genewiz Inc. Sequence confirmed products were digested and ligated into expression vectors. Clones were confirmed by analytical restriction endonuclease reactions and DNA sequencing at Genewiz Inc.

3E8HL(205C).scFv (SEQ ID NOS: 34 and 35), 3E8HL(GGGGS)4.scFv (SEQ ID NOS: 36 and 37), 3E8HL(GGGGS)3.scFv (SEQ ID NOS: 38 and 39), 3E8HL(GSSG), (SEQ ID NOS: 42 and 43), 3E8HL(GGGGS), (SEQ ID NOS: 32 and 33), and 3E8HL(SGGGG), (SEQ ID NOS: 30 and 31) open reading frames were generated from overlapping polymerase chain reactions using 3E8HL(GGGGS), as the template. 3E8LH(GGGGS)4.scFv and 3E8LH(GGGGS)3.scFv open reading frames were generated from overlapping polymerase chain reactions using 3E8.scFv as the template. Full-length genes were digested with restriction endonucleases NdeI and BamHI before ligation into overexpression vector, pHLIC. Each DNA clone was verified by analytical restriction endonuclease digest and DNA sequencing at Genewiz Inc.

Orientation Variants:
Expression pHLIC variants were transformed into C43(DE3) *E. coli* and plated on LB agar supplemented with ampicillin. Single colonies are selected the next day to inoculate seed cultures (25 mL 2×YT with ampicillin per 1 L desired expression media). After the seeds reach saturation they are used to inoculate 1 L of 2×YT with ampicillin in 4 L nonbaffled flasks. Expression cultures are grown to O.D.600=~0.8 at 37° C. before cold shock. Here, cold shock is described as 1 hour at 4° C., or submerged in ice water for approximately 20 minutes. Half way through the cold shock procedure, the cultures are induced with 0.05 mM IPTG. Upon completion of cold shock, the flasks are returned to the shaker/incubator overnight (16 hrs) at 16° C.

Purification

Post expression cells are harvested at 5000 g by centrifugation. Pellets are either frozen at −80° C., or immediately purified. To purify, cell pellets are resuspended in 25 mL lysis buffer (50 mM Tris·HCl, 300 mM NaCl, 10 mM imidazole pH 8.0) for each 1 L of expression media. The following reagents were added to the resuspended cells to facilitate lysis and purification: 5 mM MgCl2, 0.5 mM CaCl2), 2 U mL-1 DNase (Pierce), 200 ng mL-1 RNase (Fisher), 0.5 mg mL-1 lysozyme (Fisher), and 0.1% Triton-X-100. The samples were incubated at 4° C. for 30 minutes with gentle stirring. Next, the cells were mechanically lysed by an Avestin Emulsiflex C2 between 15,000 and 20,000 psi. Centrifugation at 15,000 g was performed to separate the soluble and insoluble fractions. The soluble fraction was bound to 1 mL of 50% Ni-NTA resin (Thermo) for each 1 L of expressed media for at least 1 hour. After nickel binding, the sample was added to a prefritted column and washed (50 mM Tris·HCl, 300 mM NaCl, 20 mM imidazole pH 8.0) before elution (50 mM Tris·HCl, 300 mM NaCl, 250 mM imidazole pH 8.0).

The eluted fraction was treated with 1 mM DTT and the cysteine protease from Tobacco Etch Virus (TEV) to cleave the hexahistidine fusion. The reaction was performed at room temperature overnight (16 hours), before a second aliquot of TEV and DTT were added for an additional 4 hours. The cleaved sample was dialyzed into lysis buffer and incubated with 50% Ni-NTA agarose for at least 1 hour before application to a second prefritted column. The flow through was collected and dialyzed into phosphate buffered saline (PBS) for characterization. Concentration and purity were assayed by SDS-PAGE against known standards.

Characterization

Binding (Surface Plasmon Resonance)

Figure 30:
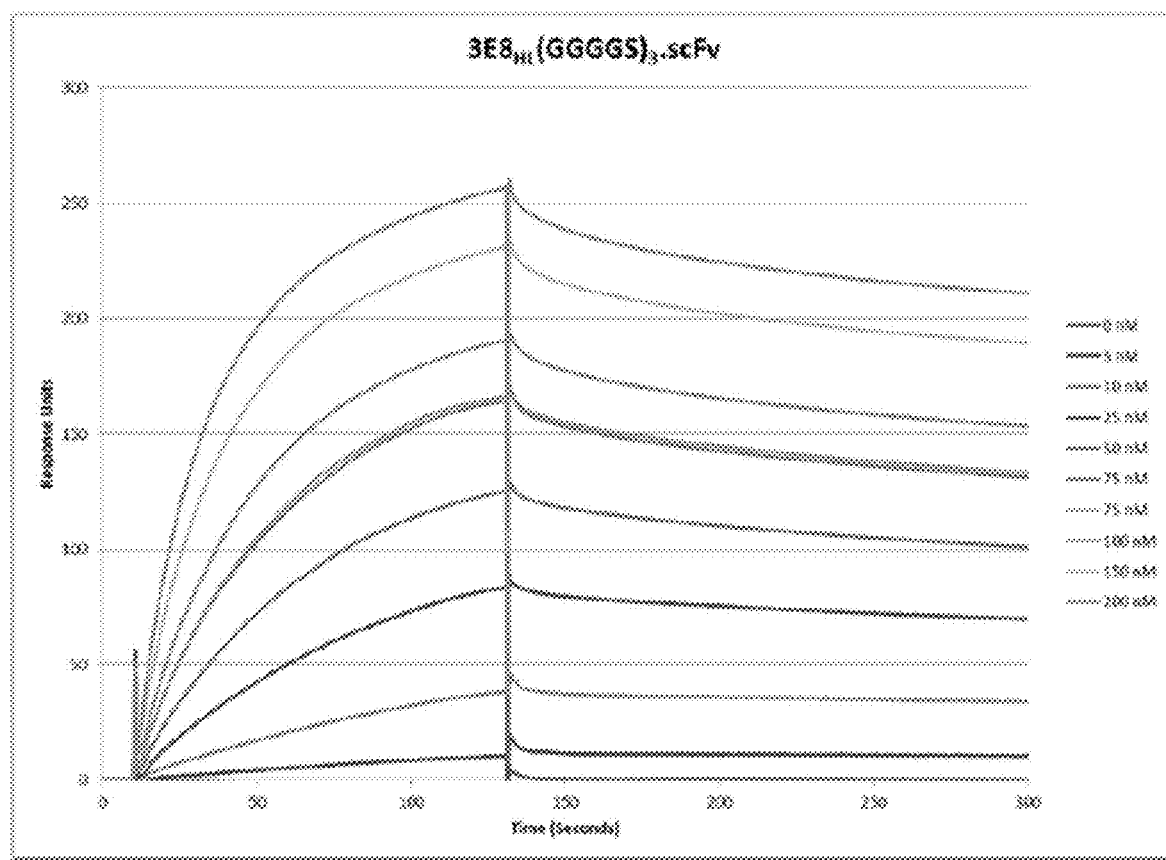
FIG. 30 shows response units for various concentrations of $3E8_{HL}(GGGGS)_3$scFv.

The binding constants were determined using a Biacore T100. Protein concentrations were run at 0, 5, 10, 25, 50, 75, 100, 150, and 200 nM with 75 nM run in duplicate (FIG. 30). Association and dissociation times of protein dilutions were 120 and 180 seconds respectively.

Construct and KD (nM)
3E8LH(G).multimer 3.7
3E8LH(GG).multimer 4.6
3E8LH(GGG).multimer 5.5
3E8LH(GGGG).diabody 14.9
3E8LH(GSSG).diabody 11.9
3E8LH(GGGGS).diabody 14.0
3E8LH(SGGGG).diabody 11.8
3E8LH(GGGGS)4.scFv 11.0
3E8LH(GGGGS)3.scFv 7
3E8HL(GGGG).diabody 5.3
3E8HL(GSSG).diabody 5.6
3E8HL(GGGGS).diabody 2.6
3E8HL(GGGGS)his6.diabody 11.1
3E8HL(SGGGG).diabody 5.5
3E8HL(GGGGS)4.scFv 5
3E8HL(GGGGS)3.scFv 5
3E8HL(205c).scFv 7.8

Stability (Differential Scanning Fluorimetry)

Figure 31:
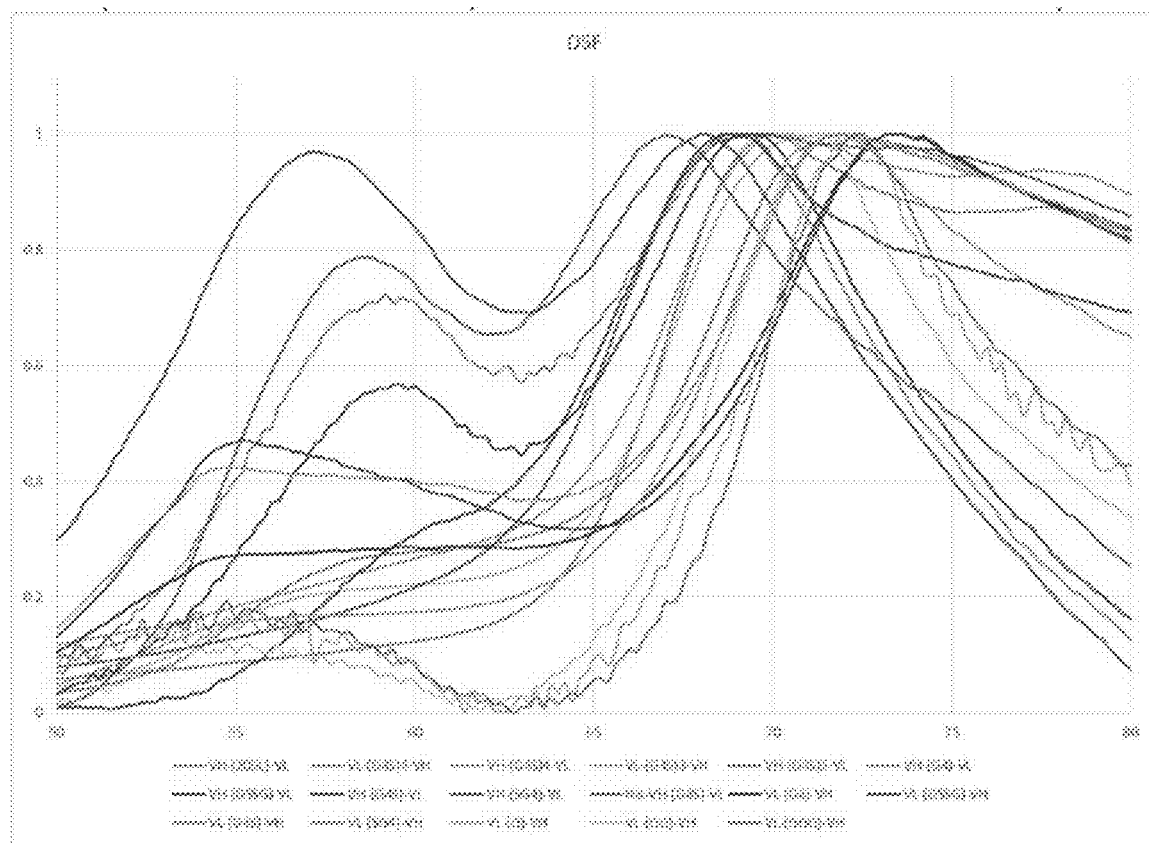
FIG. 31 shows the thermal denaturation of TIM variants performed at 25 uM protein with 5×SYPRO Orange dye. The melts were assayed using a Bio-Rad C10000 thermal cycler with a ramp rate of 1° C. min-1 at 0.2° C. intervals. The data was exported into Microsoft Excel 2013. The T½ was calculated as the temperature with the maximum slope as determined from a 5° window around each point.

The thermal denaturation of TIM variants was performed at 25 uM protein with 5× SYPRO Orange dye. The melts were assayed using a Bio-Rad C10000 thermal cyler with a ramp rate of 1° C. min-1 at 0.2° C. intervals. The data was exported into Microsoft Excel 2013. The T½ was calculated as the temperature with the maximum slope as determined from a 5° window around each point (FIG. 31).

Quaternary Structure (Gel Filtration Chromatography)

Oligomeric State

The quaternary structure of all scFv, diabody, and multimer constructs were assayed by gel filtration chromatography. 3E8.scFv constructs have molecular weights ranging from 26.5 to 28.3 kDa and elute mostly as monomeric species with some dimeric species. 3E8.G$^4$S constructs have molecular weights ranging from 25.8 to 27.1k Da and elute as a single dimeric species. 3E8. Multimer constructs have molecular weights ranging from 25.6 to 25.7 kDa.

Sequence Data and GMP-Like Production of 3E8.G$^4$S

The protein is an antibody fragment that binds the disaccharide, Sialyl-Tn, which is overexpressed in a broad range of human adenocarcinomas.

II. Composition & Materials

A. Protein Sequence (SEQ ID NO: 46)
MKYLLPTAAAGLLLLAAQPAMA/QVQLVQSGAEVKKPGASVKVSCKASGY

TFTDHAIHWVRQAPGQRLEWMGYFSPGNDDFKYSQKFQGRVTITADKSSS

TAYMELSSLRSEDTAVYYCARSWIMQYWGQGTLVTVSSGGGGSDIVMTQS

PDSLAVSLGERATINCKSSQSVLYSSNNKNYLAWYQQKPGQPPKLLIYWA

STRESGVPDRFSGSGSGTDFTLTISSLQAEDVAVYYCQQYYSYPLTFGGG

TKVEIK*

The primary structure of 3E8.G$^4$S is shown with the variable heavy domain underlined, GGGGS linker in bold, and the variable light domain italics. The protein is expressed with a PelB leader sequence for export (SEQ ID NO: 3) to the periplasm. The endogenous signal peptidase from E. coli cleaves the leader sequence at the "/" between the alanine and glutamine leaving the final product "QVQ . . . " The product contains no additional post-translational modifications. The final product contains 233 amino acid residues. The following properties are calculated based on the amino acid sequence of 3E8.G$^4$S:

Number of residues 233
Molecular weight 25,610.5 Da
pI 8.36
Charge at (pH) +22.9(3), +18.0(4), +8.6(5), +4.9(6), +3.3 (7), +1.3(8), −3.6(9), −16.4(10)

B. DNA Sequence (SEQ ID NO: 47)
5'ATGAAATACTTGTTACCAACGGCAGCTGCTGGACTACTCCTATTGGCGG

CTCAACCTGCTATGGCTCAAGTACAACTAGTACAGTCGGGGGCGGAAGTCA

AGAAACCGGGTGCAAGCGTGAAGGTGAGTTGTAAAGCATCTGGTTATACAT

TCACAGACCATGCGATACATTGGGTCAGACAAGCACCGGGGCAACGTCTGG

AATGGATGGGGTACTTTAGCCCTGGGAATGACGATTTCAAGTACTCTCAAA

AATTTCAAGGCCGGGTTACAATCACCGCCGATAAATCATCGTCAACAGCCT

ATATGGAGCTTTCGTCCTTGAGATCTGAGGATACGGCTGTTTACTATTGCG

CGAGATCTTGGATAATGCAGTATTGGGGACAAGGTACCCTCGTAACTGTGT

CATCTGGCGGAGGTGGCTCCGACATTGTGATGACACAGAGTCCTGACTCAT

-continued

TAGCGGTTTCCTTGGGGGAACGGGCAACTATTAACTGTAAGTCCAGTCAAT

CGGTCCTGTACTCGTCAAATAACAAGAATTATTTAGCTTGGTACCAGCAAA

AGCCTGGGCAGCCGCCTAAACTTTTGATCTACTGGGCGAGCACTAGAGAGT

CCGGAGTACCAGACCGCTTTAGTGGGTCAGGTTCTGGAACGGATTTTACCC

TCACTATTTCGAGCTTACAGGCGGAAGATGTAGCTGTCTATTACTGCCAGC

AGTATTATAGCTATCCACTTACGTTCGGCGGTGGCACCAAGGTTGAAATAA

AATAA3'

C. Plasmid Features

Figure 32:
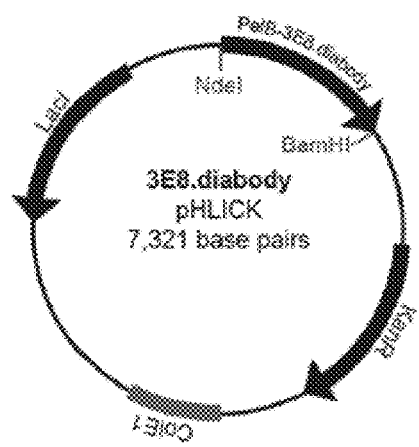
FIG. 32 shows the plasmid insert for $3E8.G^4S$.

3E8.G⁴S is cloned into the T7 overexpression vector, pHLICK (Durani, Sullivan, and Magliery (2012) *Protein Expression and Purification* 85, 9-17) (FIG. 32). The plasmid is related to pHLIC, but substitutes the β-lactamase gene for ampicillin resistance with the neomycin phosphotransferase II gene for kanamycin resistance. Both vectors are derivatives of pET11a. The open reading frame for 3E8.G⁴S is placed downstream of the T7 promoter between the NdeI and BamHI restriction endonuclease sites. Finally, the plasmid harbors the ColE1 origin for high copy number. Complete Plasmid DNA sequence is found in SEQ ID NO: 48.

Materials

DNA: Plasmid miniprep of 3E8.G⁴S pHLICK
Transformed strain: 3E8.G⁴S pHLICK in DH10β
Transformed strain: 3E8.G⁴S pHLICK in BLR(DE3)

All constructs confirmed by DNA sequencing at Genewiz Inc.

Expression

Strain and Plasmid Selection

Antibody fragments of 3E8 were originally cloned into pCOLD IV (Takara Bio Inc.) for cold shock expression under the cspA promoter. When transformed and screened in DH1013, XL1-Blue, and NEB Express, similar yields were obtained (~0.05 mg $L^{-1}$). Here, single transformants were used to inoculate 20 mL of 2×YT (16 g Bacto Tryptone, 10 g Bacto Yeast Extract, 5 g NaCl) supplemented with 1% glucose and appropriate antibiotic. The seed cultures were grown overnight at 37° C. with rigorous shaking (225 rpm). The next day, the 20 mL saturated seeds were diluted into 1 L of 2×YT in a 2 L baffled flask and grown at 37° C. and 225 rpm to OD600=0.75. At mid-log the flasks were plunged into ice water for 10 minutes and treated with 0.1 mM IPTG to induce the tandem cspAllac promoter. After cold shock induction, the cultures were returned to the shaker incubator and grown overnight at 1° C. This protocol and plasmid produced low yields with inconsistent results. As a result, the antibody fragment genes were subcloned into pHLIC for T7 expression.

The above expression protocol was replicated for pHLIC transformed into BL21(DE3), C41(DE3), C43(DE3), T7 Express, T7 Express Iq, T7 Express LysY, T7 Express LysY/Iq, and Novablue(DE3). From this study, it was determined that the best expression was obtained from Lucigen's Overexpress C43(DE3). This is a BL21(DE3) derivative originally selected for overexpression of toxic variants including membrane proteins.

Two additional T7 expression strains were tested, BLR (DE3) and HMS174(DE3). BLR(DE3) is a BL21(DE3) derivative that is recA-, resulting in improved genome and plasmid stability. HMS174(DE3) is a K12 bacteria that also contains a mutations to the recA gene. (FIG. 33). When both strains were screened for T7 overexpression with pHLIC, BLR(DE3) consistently outperformed HMS174(DE3) and generated results comparable to C43(DE3). Therefore, 3E8.G⁴S was optimized with pHLICK in BLR(DE3).

Shake Flask

The following parameters have been optimized for 3E8.G⁴S expression in shake flasks: IPTG concentration, temperature, time of induction, shaker speed, flask choice, and glucose supplementation.

i. IPTG concentration. Our lab has expressed antibody fragments of 3E8 under various concentrations of IPTG including 1 mM, 0.1 mM, and 0.05 mM. It has been determined that 0.05 mM IPTG yields the highest overall expression and consistency.

ii. Temperature. Flasks are incubated at 37° C. from inoculation to induction. At mid- to late-log phase the flasks are removed from the shaker incubator and cold shocked to induce chaperone expression. This is accomplished by either plunging the cultures in ice water for 10 minutes, or incubating the flasks for 30-60 minutes at 4° C. Post cold shock the flasks are returned to the shaker incubator and grown at 16° C. overnight.

iii. Time of induction. Induction originally occurred at OD600=0.6-0.75, but it was concluded that higher yields were obtained with later induction. Currently, induction takes place at OD600=1.0-1.5.

iv. Shaker speed and flask choice. Several expressions of 3E8 antibody fragments resulted in reduced optical densities from cellular lysis after induction with IPTG. Quality control confirmed that these cultures were not afflicted with phage. It was hypothesized that cellular lysis was the result of membrane instability caused by periplasmic export of our overexpressed protein. Proteins were expressed in non-baffled flasks at reduced speeds (125 rpm). To counterbalance the loss of oxygenation, 1 L of media is prepared in 4 L flasks. These adaptions improved reproducibility, but did not negatively affect yield. As a result, nonbaffled flasks were used at 225 rpms to induction, then the speed is reduced to 125 after addition of IPTG.

v. Glucose supplementation. In order to limit leaky expression of the T7 RNA polymerase, transformants are plated on LB agar (10 g Bacto Tryptone, 5 g Bacto Yeast Extract, 5 g NaCl, 15 g Bacto Agar per liter) supplemented with appropriate antibiotics and 1% glucose. Seed cultures of 2×YT are inoculated with a single colony, appropriate antibiotic, and 1% glucose. Expression flasks are not supplemented with glucose, and saturated seed cultures containing 1% glucose are diluted at least 40-fold into expression media.

In summary, 3E8.G⁴S is expressed in BLR(DE3) from the overexpression plasmid, pHLICK. Transformants are plated on LB agar supplemented with kanamycin and 1% glucose, and grown overnight at 37° C. The next day, a single colony is used to inoculate 20 mL (per 1 L desiredexpression) of 2×YT with kanamycin and 1% glucose. The seed culture is grown overnight at 37° C. at 225 rpm. On the third day, the 20 mL saturated seed is diluted into 1 L of 2×YT with kanamycin in a 4 L nonbaffled flask. The culture is grown at 37° C. and 225 rpm to OD600=1.0-1.5. At this stage, the flasks are plunged into ice water for 10 minutes or moved to the 4° C. cold room for 30-60 minutes. Half way through the cold shock procedure, IPTG is added to a final concentration of 0.05 mM (50 µL of 1 M IPTG per 1 L media). At the conclusion of the cold shock, the cultures are returned to the shaker/incubator at 16° C. and 125 rpm for approximately 16 hours. These procedures yield ~0.25 mg $L^{-1}$.

Batch-Fed Fermentation

All fermentation optimization has taken place in a New Brunswick Bioflo 110. This bioreactor possesses a 4 L vessel and expressions were performed at the 3 L scale. Furthermore, all expressions to date, were performed on 3E8.G$^4$S pHLICK in BLR(DE3).

i. Seed cultures. A single transformant was selected from solid media to inoculate a pre-seed culture of 20 mL 2×YT supplemented with appropriate antibiotic and 1% glucose (37° C., 225 rpm, overnight). Next, 10 mL of the saturated pre-seed was used to inoculate the seed culture. The seed culture contains 250 mL 2×YT, appropriate antibiotic, and 1% glucose in a 500 mL flask (baffled or nonbaffled). This culture is grown to saturation at 37° C. and 225 rpm. The entire saturated seed culture is used to inoculate the 3 L expression culture (12-fold dilution).

ii. Media. The following chemical media (animal free) was used a base for initial fermentation trials (all values are per 1 L):

4 g K2HPO4
1 g KH2PO4
1 g NH4Cl
2.4 g K2SO4
20 g Bacto Casamino Acids
3 g Bacto Yeast Extract
40 g Glycerol
10 mL Trace elements*
pH 7

*Trace element solution (all values are per 1 L)

5 g EDTA
0.5 g FeCl3·6H2O
0.05 g ZnO
0.01 g CuCl2·2H2O
0.01 g Co(NO3)2·6H2O
0.01 g (NH4)6Mo7O24·4H2O
pH 7 iii. Bioreactor conditions. The following conditions are summarized from several trials (37° C. to induction, 20° C. after addition of IPTG). The two primary conditions that were optimized were dissolved oxygen percentage and source, as well as agitation speed. The standard Rushton impeller was used, but did not include baffles. Initially, baffles were used and set the agitation speed to 100 rpm based on previous experience with shake flasks—baffled flasks at 225 rpm led to cellular lysis. (FIG. 34). When agitation speeds were increased to 300 rpm, the optical densities reached ~7 using the base media described above. Cultures grown at 300 rpm could be coaxed to OD600>10 by the addition of additional sterile filtered carbon courses (glucose, glycerol, Bacto Casamino Acids, etc.). A richer media was conducted based on the above composition.

Modifications included 30 g Bacto Casamino Acids, 5 g Bacto Tryptone, 60 g glycerol, and 1% glucose per 1 L media. In addition, agitation speeds were increased to 1000 rpm prior to induction. Under these conditions optical densities greater than 15 were obtained. At this optical density, induction took place with 0.5 mM IPTG and the temperature and agitation speed were reduced to 20° C. and 500 rpm, respectively. This induced culture quickly depleted dO2 and growth stagnated at OD600<20. Supplemental oxygen was added to dO2=30% and cell densities increased to nearly 50 during overnight expression. At 24 hours, the cells were harvested and purified. Yields of 10 mg L-1 were achieved.

Next, the role of induction point and the expression time course for 3E8.G$^4$S was determined. The sample was prepared identically as before, but the culture was allowed to reach OD600=45, before added 0.5 mM IPTG, shifting the temperature to 20° C., reducing agitation to 500 rpm, and adding supplemental oxygen to maintain dO2 at 30%. This culture maintained an optical density of 45-50 for nearly 24 hours post induction when the experiment was terminated. At 0.5, 1, 1.5, 2, 3, 4, 6, and 8 hours 50 mL of culture were harvested and snap frozen for further studies (FIG. 35). Each cell pellet was resuspended to an OD600=46, and 10 mL of normalized cultures were purified in parallel.

The results shows that under these conditions the highest yields can be obtained when the cultures are harvested between 2 and 3 hours of induction. The four hour time point appears to be an anomaly (disrupted Gaussian distribution), likely due to inconsistent purification. From this experiment it was calculated that 33 mg L-1 (100 mg total) would have been obtained if the entire culture was harvested and purified between 2-3 hours.

iv. Additional parameters. pH was maintained at 7 by base titration with ammonium hydroxide and acid titration with phosphoric acid. Temperature was maintained by a heating blanket and circulating cold water through closed-loop coils.

Purification

Overview

Figure 36:
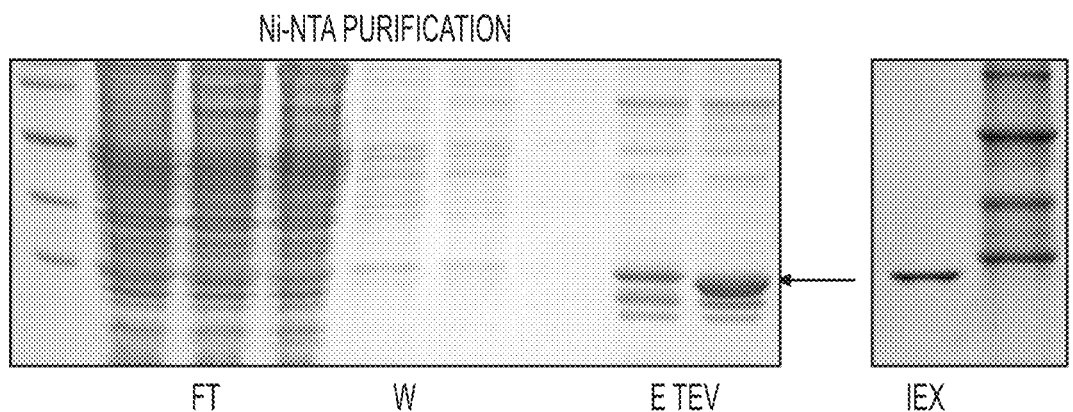
FIG. 36 shows that the $3E8.G^4S$ was expressed with a cleavable hexahistidine tag and immobilized metal affinity chromatography (IMAC). After elution from the Ni-NTA column, the protein was incubated at room temperature overnight with the cysteine protease from Tobacco Etch Virus (TEV) and 1 mM DTT. A second Ni-NTA column is used to remove the hexahistidine tag, His-tagged-TEV protease. A cation exchange step is used to remove several protein contaminants. By SDS-PAGE, the desired product is nearly homogeneous.

3E8.G$^4$S was expressed with a cleavable hexahistidine tag and immobilized metal affinity chromatography (IMAC). After elution from the Ni-NTA column, the protein was incubated at room temperature overnight with the cysteine protease from Tobacco Etch Virus (TEV) and 1 mM DTT. A second Ni-NTA column is used to remove the hexahistidine tag, His-tagged-TEV protease. A cation exchange step is used to remove several protein contaminants. By SDS-PAGE, the desired product is nearly homogeneous. (FIG. 36).

Figure 37:
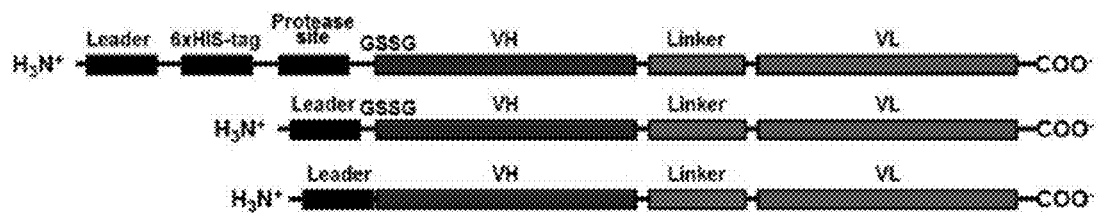
FIG. 37 shows purification strategies were employed that remove reliance on TEV protease and hexahistidine tags for licensing and costs. As a result two new variantsv were cloned and characterized that remove the hexahistidine tag and TEV protease recognition sequence. The original $3E8.G^4S$ leaves a small GSSG linker at the N-terminus. To test the importance of the linker, two variants were tested— one that begins GSSG-QVQ . . . , and a second that begins with the native QVQ . . . .

Purification strategies were employed that remove reliance on TEV protease and hexahistidine tags for licensing and costs. As a result two new variants were cloned and characterized that remove the hexahistidine tag and TEV protease recognition sequence. The original 3E8.G$^4$S leaves a small GSSG linker at the N-terminus. To test the importance of the linker, two variants were tested—one that begins GSSG-QVQ . . . , and a second that begins with the native QVQ . . . (FIG. 37).

Note: The GSSG linker did not affect the folding, stability, function, or expression of 3E8.G$^4$S. As a result, the bottom-most construct shown above. Here, the N-terminus begins with the PelB leader sequence to direct the disulfide-containing protein to the periplasm. Upon leader sequence cleavage by the endogenous signal peptidase from E. coli, the final proteins begins with amino acids, QVQ.

Harvesting and Storage

After overnight growth, the cells are harvested by centrifugation. Here, the expression is spun at 5000 g for 10 minutes using a Sorvall RC6+ centrifuge. The media is decanted and the cell paste is transferred to specimen cups for storage at −80° C. Cell pastes have been stored at this temperature for six months with no loss in activity.

Cellular Lysis and Clarification

The cell pastes are removed from the −80° C. freezer and thawed on ice for approximately 20-30 minutes. Next, the cells are resuspended in Protein L binding buffer (20 mM sodium phosphate, 150 mM sodium chloride, pH 7.2). For shake flask expression, the cell pastes are resuspended in 20-25 mL binding buffer per 1 L expression. We have not scaled this step for full 3 L fermentations reaching OD600=~40. The cells are resuspended to homogeneity before the sequential addition of 75 µL 2 M MgCl2, 150 µL CaCl2, 10 µL RNase A (10 mg mL-1, USB Cat. #: 78020Y), 5 μL DNase (10 Units μL-1, Roche Cat. #: 04716728001), 300 μL 10% Triton-X-100—all values per 30 mL resuspension.

Final Concentrations
MgCl2 5 mM
CaCl2 0.5 mM
RNase 3.3 μg mL-1
DNase 1.6 Units mL-1
Triton X-100 0.1%

The 3E8.G$^4$S is exported to periplasm of BLR(DE3). Cellular lysis was used, where the cytoplasm and periplasm are isolated together. This procedure increased yield, but did not affect activity. After the addition of the listed supplements, the cells are mechanically lysed with an Avestin Emulsiflex C3. Here, the resuspension is applied to the system and cycled through once with no pressure differential. Upon completion of this step, the cells are then lysed by alternating the pressure between 0 and 15,000-20,000 psi. The entire resuspension is circulated through the apparatus 3-4 times to ensure complete lysis and homogeneity. Next, the cell lysis is transferred to SS34 tubes and spun at 15,000 g for 45 minutes in a Sorvall RC6+ centrifuge to separate the soluble and insoluble cell fractions. After the 45 minute spin, the supernatant is transferred to a second SS34 tube and spun for an additional 45 minutes at 15,000 g. The supernatant represents the cleared lysate.

Protein L Chromatography

The first purification step to extract 3E8.G$^4$S from the cleared lysate is Protein L chromatography. The purification procedures were optimized using a 1 mL GE Healthcare HiTrap Protein L column (Cat #: 29-0486-65). The cleared lysate was diluted 1:1 in Protein L binding buffer (20 mM sodium phosphate, 150 mM sodium chloride, pH 7.2), or dialyzes the cleared lysate into Protein L binding buffer (4×1 L exchanges for 30 minutes each—assume ~25 mL sample). These two procedures bound the column nearly quantitatively.

Figure 38:
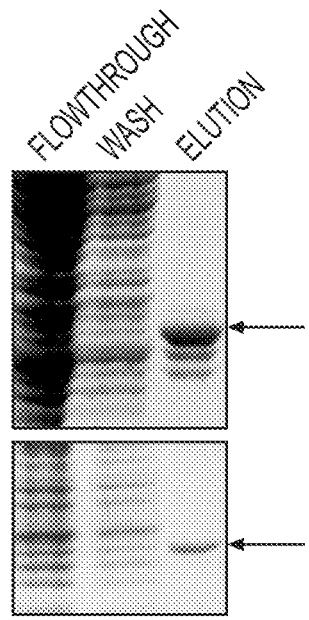
FIG. 38 shows FPLC Procedure (1 L expression from shake flask): The Protein L column is first equilibrated with 5 column volumes (CV) of Protein L binding buffer. Next, the sample is loaded at 1 mL min-1 before washing with 10 CVs Protein L binding buffer (1 mL min-1 washing).

FPLC Procedure (1 L Expression from Shake Flask):

The Protein L column is first equilibrated with 5 column volumes (CV) of Protein L binding buffer. Next, the sample is loaded at 1 mL min-1 before washing with 10 CVs Protein L binding buffer (1 mL min-1 washing). (FIG. 38). Next, the sample is eluted with Protein L elution buffer (100 mM glycine pH 3). The SDS-PAGE gel shown to the right shows the flowthrough, wash, and elution of the hexahistidine tagged 3E8.G$^4$S. Note that the desired antibody fragment is arrowed and that several proteolytic products or copurifying contaminates are bound and eluted from the Protein L column. These bands are able to be removed by ion exchange chromatography. Fortunately, when hexahistidine tag was removed and TEV protease recognition sequence from the open reading frame, the copurifying bands are absent (see gel to right, below). Protein L has produced nearly quantitative purification and near-homogeneity by SDSPAGE (>95%).

Ion Exchange Chromatography

Protein L purification was followed with ion exchange as polishing steps and to remove contaminant nucleic acid and endotoxins. Based on Scripp's Protein Calculator V3.3, the pH of 3E8.G$^4$S is 8.4, and therefore more amenable to binding negatively charged ion exchangers. Here, is research-scale optimization is shown for 3E8.binding binding and elution from 1 mL Resource Q (GE Cat. #: 17-1177-01) and Resource S (GE Cat. #: 17-1178-01) columns.

Traditionally, 3E8.G$^4$S is exchanged into Resource S binding buffer (50 mM potassium acetate, 15 mM sodium chloride, pH 5) via size exclusion chromatography (PD10, GE Cat. #: 17-0851-01) prior to Resource S column loading. After the column is equilibrated with 5 CV Resource S binding buffer, the sample is added at 1 mL min-1. The column is washed with 2 CV Resource S binding buffer before elution. A gradient from Resource S binding buffer to Resource S elution buffer (50 mM potassium acetate, 1 M NaCl, pH 5) was performed. The 3E8.G$^4$S generally elutes at 300 mM sodium chloride (~30% elution buffer). Under these conditions, binding and subsequent elution are nearly quantitative.

To test the feasibility of tandem purification between Protein L chromatography and Resource S ion exchange, the antibody fragment was buffer exchanged into Protein L elution buffer and applied to the Resource S column. Here, the sample bound very tightly and eluted with a broad profile between 600-800 mM sodium chloride (60-70% 100 mM glycine, 1 M sodium chloride pH 3). The additional drop in pH from 5 to 3 likely dictates the enhanced binding to the Resource S column. It may be beneficial to adjust the pH proceeding the Protein L elution with concentrated buffer of approximately pH 5.

Figure 39:
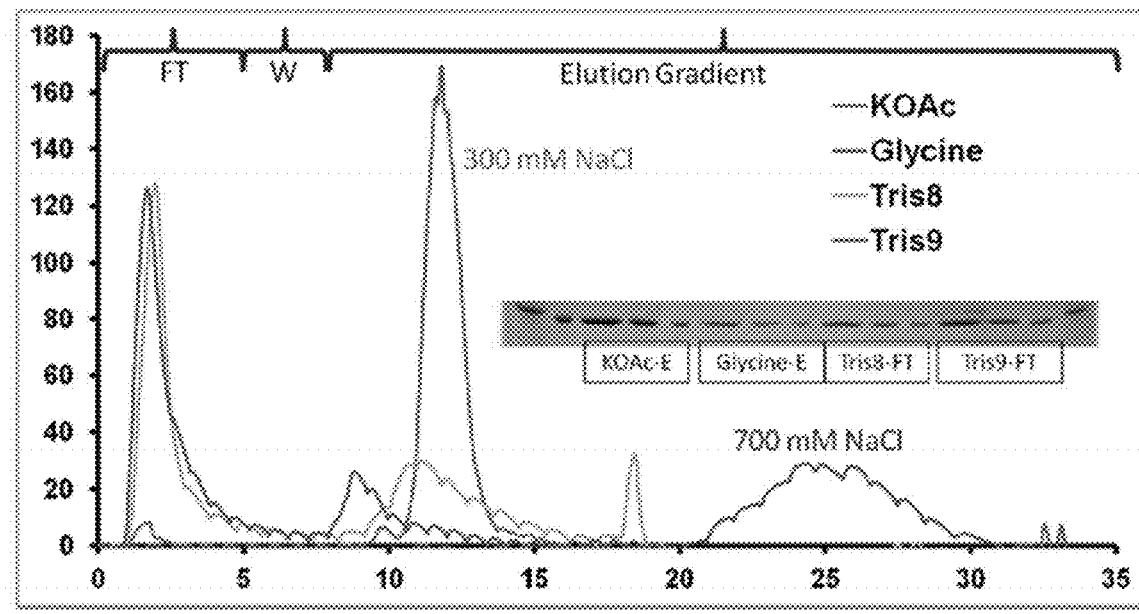
FIG. 39 shows a final ion exchange column was used to remove bacterial endotoxins. When $3E8.G^4S$ is exchanged into 20 mM Tris at pH 8 or 9. This sample was applied to a Resource Q column where little to no binding was observed. The flowthrough was collected, which is expected to be depleted of both endotoxin and nucleic acids. The primary data for these experiments are shown in the below graphs. Note that the elutions from Resource S and flowthroughs from Resource Q were run on SDS-PAGE gel to confirm the protein identity.

Nucleic acids and bacterial endotoxins are known to tightly associate with positively charged ion resins. A final ion exchange column was used to remove these contaminants. When 3E8.G$^4$S is exchanged into 20 mM Tris at pH 8 or 9. This sample was applied to a Resource Q column where little to no binding was observed. The flowthrough was collected, which is expected to be depleted of both endotoxin and nucleic acids. The primary data for these experiments are shown in the below graphs. Note that the elutions from Resource S and flowthroughs from Resource Q were run on SDS-PAGE gel to confirm the protein identity. (FIG. 39).

Low Sensitivity Nucleic Acid Analysis

Figure 40:
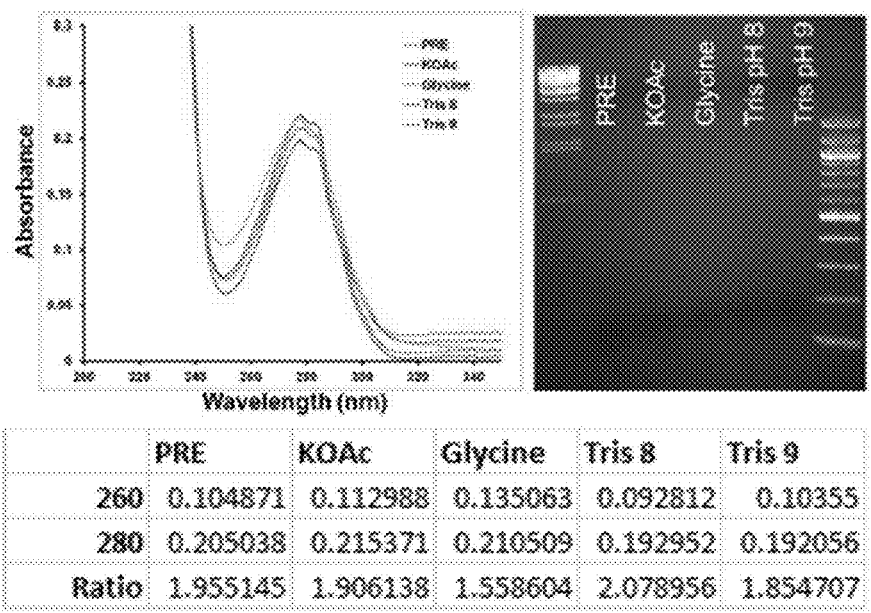
FIG. 40 shows various optimization conditions.
Figure 41:
FIG. 41 shows a PET scan of a $3E8.G^4S$ mouse with $^{124}$I-diabody at 24 hours.
Figures 42, 43:
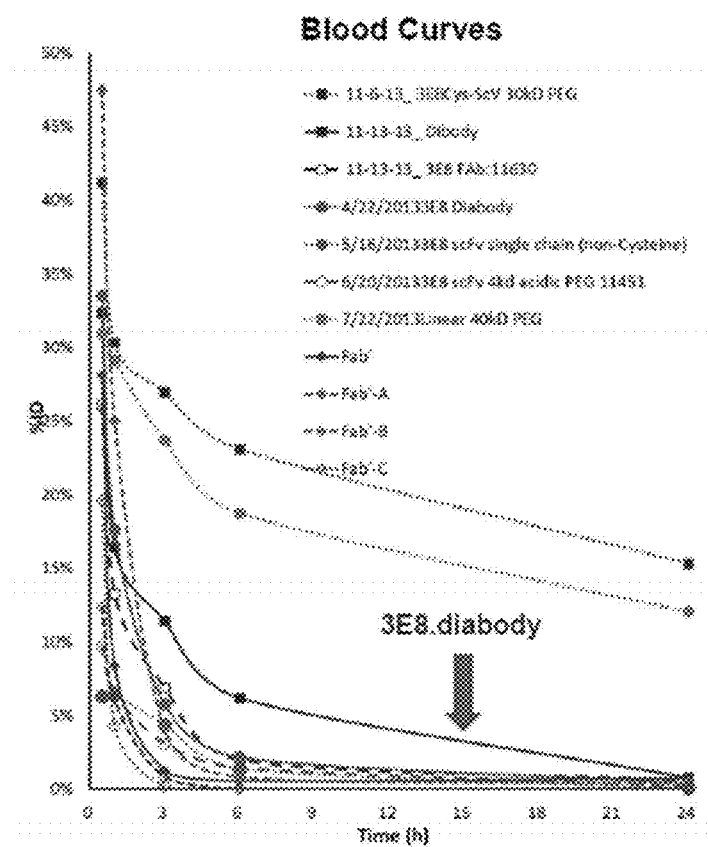
FIG. 42 shows blood curves for 3E8 antibody fragment.
FIG. 43 shows average percentage of ID/g and sd in blood, lung, heart, liver, spleen, pancreas, GI, kidney, muscle, skin, tail, and carcass of mouse.
Figure 44:
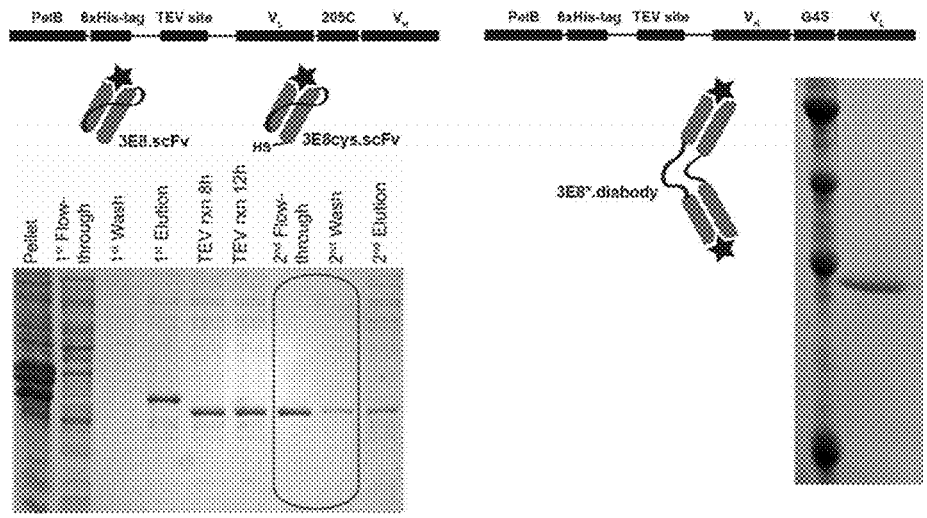
FIG. 44 shows construction and IMAC purification of 3E8.scFv and $3E8^*.G^4S$. Top: The open reading frames are shown for the antibody fragments. Bottom: The final purified scFv appears in the second flow-through and wash, by SDS-PAGE. Far Right: SDS-PAGE of ladder and purified $3E8^*.G^4S$ from C43(DE3).
Figure 45:
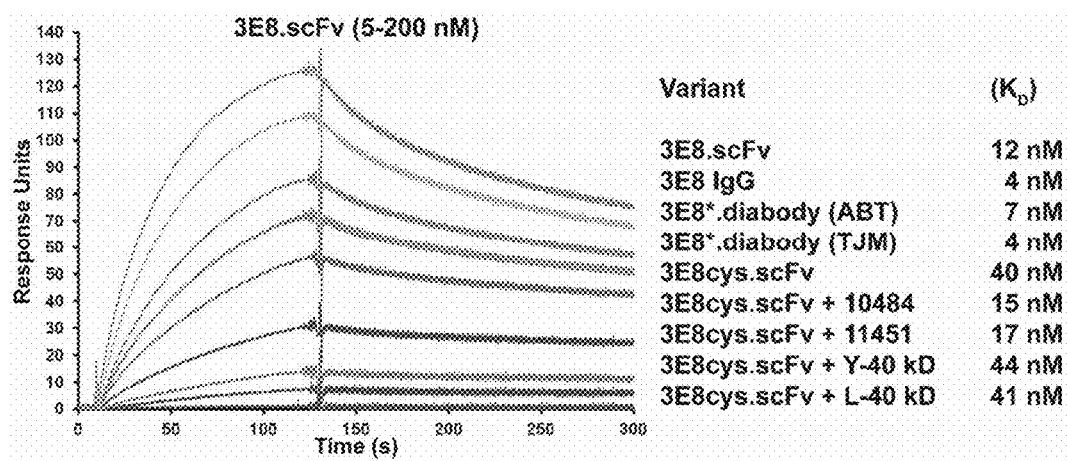
FIG. 45 shows an example sensorgraph of 3E8.scFv and dissociation constants for all studied variants. All variants studied to date exhibit low nanomolar binding to TAG-72. The two 3E8*.G$^4$S entries are the same protein sequence. The first expression and purification was performed in the laboratories of ABT. The Magliery Lab (TJM) repeated the procedure in C43(DE3) *E. coli*. Both purification yielded similar nanomolar KDs.

To assay for gross nucleic acid contamination, several samples were analyzed by DNA gel electrophoresis and ethidium bromide staining, as well as absorbance at 260 nm. An aliquot of the following samples were transferred to phosphate buffered saline (PBS) and normalized for 3E8.G$^4$S concentration by gel quantification and A280: Protein L elution pre ion exchange, Protein L elution post ion exchange from Resource S (potassium acetate), Protein L elution post ion exchange from Resource S (glycine), Protein L elution post ion exchange from Resource Q (Tris pH 8), Protein L elution post ion exchange from Resource Q (Tris pH 9). Each sample was tested by A280, A260, and ethidium bromide staining in agarose gel. No observable staining was seen with ethidium bromide, and no shoulders were detected by UV-Vis spectrophotometry. (FIG. 40).

Process Flow

Based on the current optimizations the following process flow can be used.

1. Expression by fermentation
2. Cell harvesting by centrifugation
3. Resuspension in Protein L binding buffer
4. Cellular lysis by automated pressure differential (Avestin Emulsiflex or similar)
5. Removal of insoluble material by centrifugation
6. Protein L chromatography
7. Adjust elution to pH 5 with concentrated buffer
8. Cation exchange chromatography
9. Adjust elution to pH 8-9 with concentrated buffer
10. Ion exchange chromatography
11. Transfer to storage buffer Activity Assay A 96-well plate assay for quality assuring activity (binding) can be used. It will be based on a competitive ELISA with commercially available B72.3. The binding of 3E8.G$^4$S is quantitated by surface plasmon resonance (SPR).

Example 6: Antibody Fragments

TABLE 2

Radiolabeled Protein, Amount, Radiolabeling Yield, Radiochemical Purity, Radioconcentration and Specific Activity of Radiolabeled Protein

| Radiolabeled Protein | Vol, mL | % Yield | % RCP | Radioconc, mCi/mL | SpActivity, mCi/mg |
|---|---|---|---|---|---|
| $^{125}$I-3E8*.G$^4$S | 1.0 | 88.3 | 100.0 | 0.65 | 10.85 |
| $^{125}$I-3E8.scFv | 0.6 | 34.4 | 98.9 | 0.58 | 9.60 |
| $^{125}$I-3E8cys.scFv + 11451 | 1.1 | 68.6 | 98.9 | 0.37 | 4.36 |
| $^{125}$I-3E8cys.scFv + 10484 | 1.0 | 48.3 | 98.9 | 0.31 | 4.22 |
| $^{125}$I-3E8cys.scFv + L-40 kD | 0.9 | 74.9 | 98.1 | 0.40 | 11.18 |
| $^{125}$I-3E8cys.scFv + Y-40 kD | 0.7 | 60.6 | 96.2 | 0.16 | 11.65 |
| $^{123}$I-3E8*.G$^4$S | 0.7 | 25.1 | 92.9 | 5.92 | 122.1 |
| $^{123}$I-3E8cys.scFv + 30 kD | 0.7 | 35.0 | 90.6 | 9.85 | 104.5 |

Figure 46:
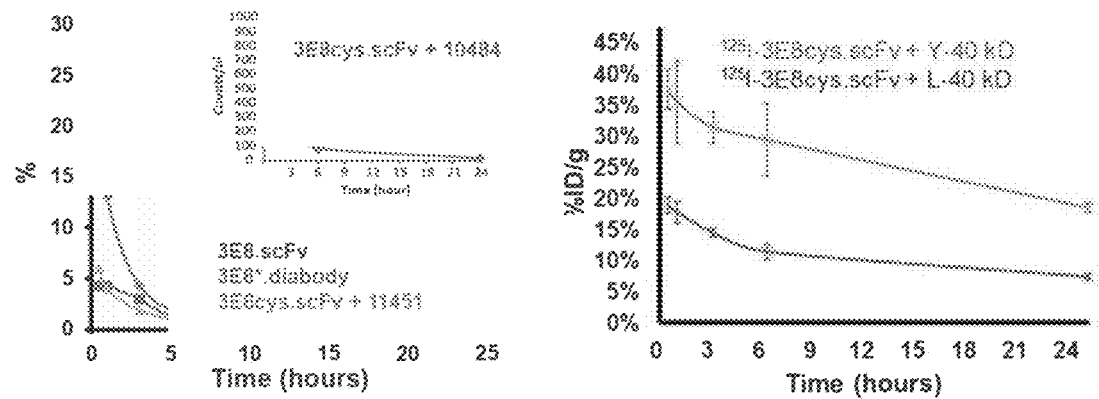
FIG. 46 shows pharmacokinetics of antibody fragments. Blood curves of 3E8*.G$^4$S, 3E8.scFv, and 3E8cys.scFv+ 11451 are shown. The 3E8*.G$^4$S exhibits the longest serum half-life of the three molecules studied. Note that 3E8cys.scFv+10484 shown as counts/μL rather than ID %/g.
Figure 47:
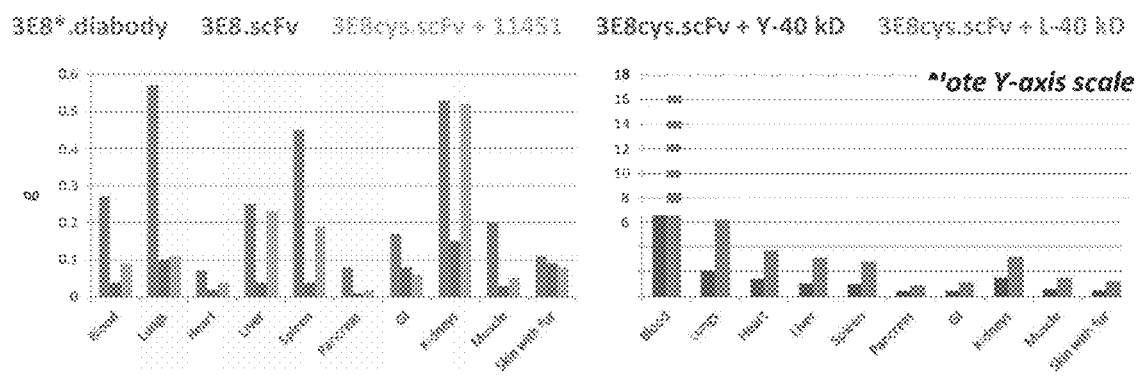
FIG. 47 shows Biodistribution data for each compound. PEGylation with the 40 kD PEGs dramatically affected the pharmacokinetic properties and biodistribution.

Preliminary analysis of the distribution data shows that about 5% ID/g is observed at 3 hours with the antibody fragment and at about 1 hour with both the naked scFv and the 11451-conjugated scFv. Thus, the smaller scFv appears to be clearing more quickly than the antibody fragment, as expected, but addition of the small, discrete PEGs did not dramatically increase the serum residence times of the scFv. Semilog plots of the blood concentration data were inconclusive. The naked scFv and the 40 kDa PEGylated scFv showed only a single linear plot, while the rest yielded two compartments of fairly similar slope, making comparisons of any rate data not meaningful. The wide range of blood retention and the ordering of compounds is well visualized in the blood curve % ID vs. time plots in FIG. 46.

The two 40 kD PEGs, one linear and one branched, greatly extended the blood clearance, well beyond that of the non-PEGylated antibody fragment. The serum half-lives of the 40 kD PEGs nearly match those obtained for full-length CC49 IgG. Tumor uptake and retention should be very strong in these derivatives, based on our known correlation between blood clearance and tumor signal; however, the tissue biodistribution at 24 hours (the next day imaging mode for $^{123}$I-SPECT/CT imaging) indicates that significant blood background remains which is likely to compromise the images.

Figure 48:
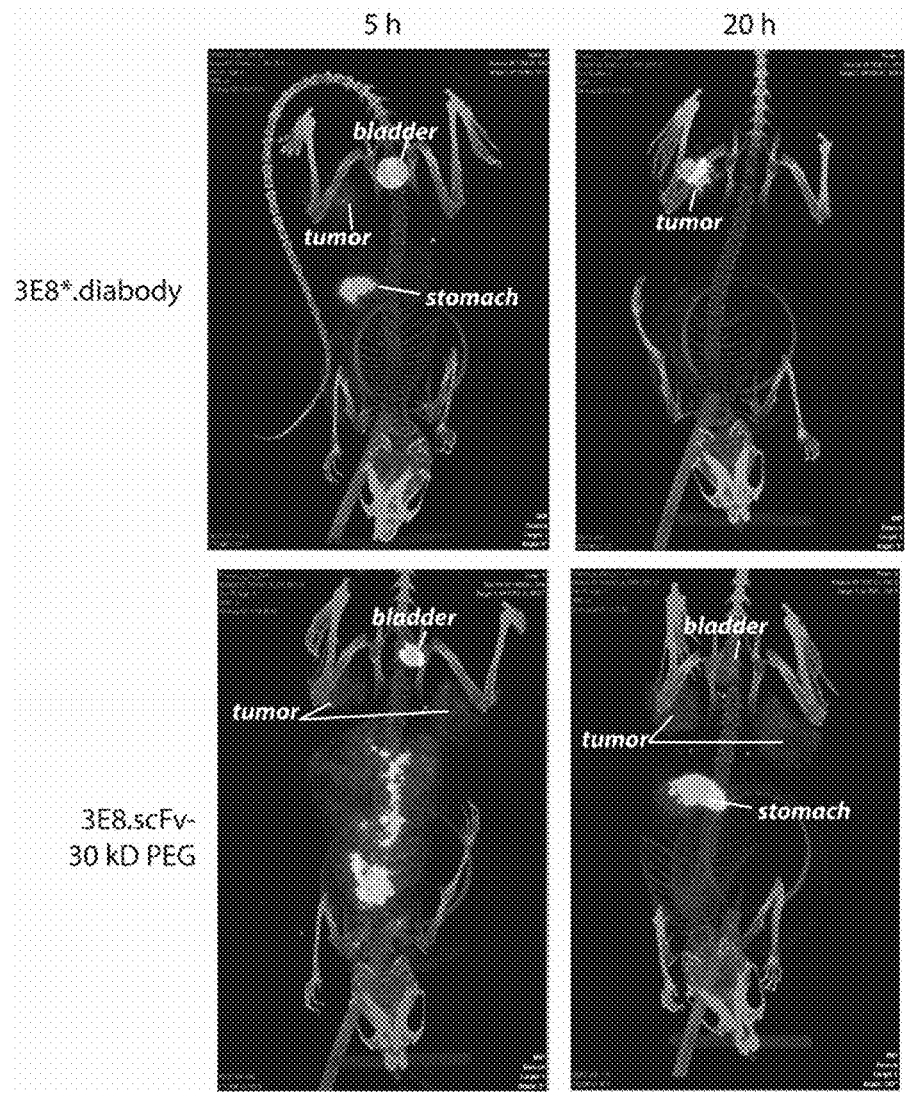
FIG. 48 shows microSPECT/CT imaging of xenograft mice.
Figure 49:
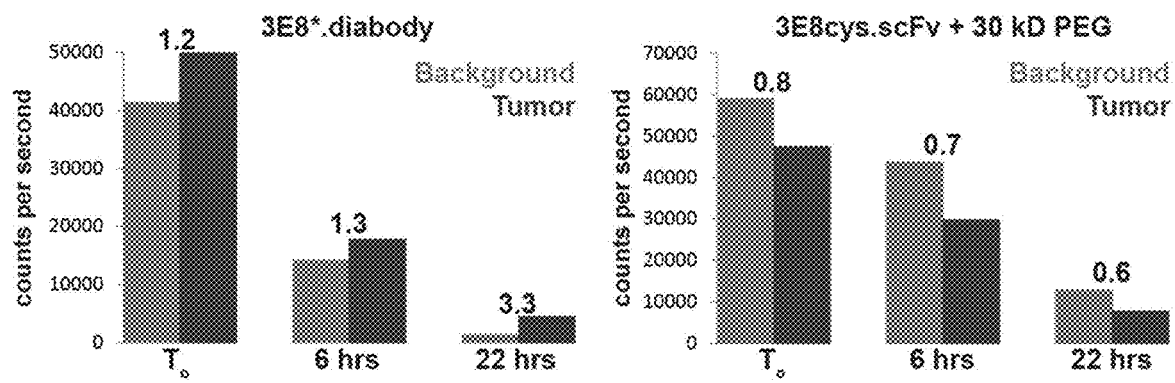
FIG. 49 shows neoprobe 3000 data.

MicroSPECT/CT scanning indicated a significant uptake of each tested molecule in LS-174T human colon carcinoma xenografts in nude mice. The main background tissues for both molecules were stomach and bladder. microSPECT/CT scanning at 5 and 20 h is shown in FIG. 48. Less background was observed for 3E8.G$^4$S at 20 h, but a higher amount of total signal was observed in the tumors for 3E8cys.scFv+30 kD conjugate at the same time point. This is consistent with the biodistribution data.

Biodistribution in Xenograft Mice

The biodistributions of the $^{123}$I-labeled 3E8.G$^4$S and 3E8.scFv+30 kD PEG in xenograft mice were determined at 22 h as described above for the $^{125}$I-labeled molecules with normal mice. The antibody fragment targets the tumor with good specificity at 22 h, with little material left in the blood and significant material found only in the kidneys (besides the tumor). A higher percentage of the initial dose of the 30 kD scFv conjugate was found in the tumor compared to the antibody fragment, but significant amounts of PEGylated scFv remained in the blood, kidneys, lungs and heart.

TABLE 3

Comparison of biodistribution of $^{123}$I-antibody fragment and $^{123}$I-30 kD in nude mice at 22 h (n = 2)

| | % ID/organ | | % ID/g | |
|---|---|---|---|---|
| | I123-diabody | I123-30 kD | I123-diabody | I123-30 kD |
| blood | 0.52 ± 0.02 | 9.87 ± 0.28 | 0.32 ± 0.03 | 5.98 ± 0.00 |
| lungs | 0.07 ± 0.03 | 0.57 ± 0.08 | 0.48 ± 0.30 | 2.96 ± 0.07 |
| heart | 0.01 ± 0.00 | 0.28 ± 0.04 | 0.12 ± 0.02 | 2.26 ± 0.33 |
| liver | 0.64 ± 0.00 | 1.86 ± 0.00 | 0.52 ± 0.01 | 1.38 ± 0.23 |
| spleen | 0.04 ± 0.00 | 0.15 ± 0.01 | 0.44 ± 0.07 | 1.79 ± 0.11 |
| pancreas | 0.01 ± 0.00 | 0.13 ± 0.00 | 0.07 ± 0.01 | 0.89 ± 0.13 |
| GI | 0.43 ± 0.18 | 6.36 ± 1.96 | 0.12 ± 0.05 | 1.64 ± 0.51 |
| Kidneys | 0.37 ± 0.05 | 1.13 ± 0.04 | 1.27 ± 0.06 | 3.21 ± 0.43 |
| muscle | | | 0.06 ± 0.01 | 0.66 ± 0.28 |
| skin | | | 0.16 ± 0.01 | 1.71 ± 0.27 |
| tumor | 0.96 ± 1.14 | 4.28 ± 1.81 | 1.78 ± 1.73 | 5.36 ± 0.02 |
| carcass | | | 0.18 ± 0.06 | 1.19 ± 0.03 |

Probe Data

In addition to SPECT/CT imaging, radioactivity was recorded using a handheld probe. At early time points the Neoprobe 2000 poorly differentiates between background and tumor. This is expected as the antibody fragments have not had time to localize to the diseased tissue and are actively circulating in the blood serum. The signal-to-noise ratios improve with time and by 22 hours there is a three-fold enhancement in tumor signal over background for 3E8.G$^4$S.

At least 3 mg of the following three antibody fragments were produced: (1) HuCC49 diabody; (2) 3E8.G$^4$S; (3) 3E8 scFv single chain. The proteins are at least 95% pure and demonstrate binding to the TAG-72 antigen.

TABLE 4

| | Yield (purified folded protein) | Purity |
|---|---|---|
| 3E8.scFv | 2 mg L$^{-1}$ | >95% |
| 3E8cys.scFv | 1.5 mg L$^{-1}$ | >95% |
| 3E8*.diabody | 1.0 mg L$^{-1}$ | >95% |

The production of conjugates of the 3E8 scFv single chain antibody fragment with three different dPEG molecules was accomplished. At least 100 μg of each of the conjugates are recovered, with a purity of ≥95%. The protein conjugates demonstrate binding to the TAG-72 antigen in vitro.

TABLE 5

| | Mass supplied for $^{125}$I-labeling (purified conjugate) | Purity | K$_D$ (SPR) |
|---|---|---|---|
| 3E8.scFv | 350 μg | >95% | 12 nM |
| 3E8*.diabody | 200 μg | >95% | 6 nM |
| 3E8cys.scFv + 10484 | 200 μg | >95% | 15 nM |
| 3E8cys.scFv + 11451 | 200 μg | >95% | 17 nM |
| 3E8cys.scFv + L-40 kD | 150 μg | >95% | 41 nM |
| 3E8cys.scFv + Y-40 kD | 150 μg | >95% | 44 nM |
| 3E8cys.scFv + L-30 kD | 150 μg | >95% | TBD |

Example 7: Purification of 3E8.G4S

3E8.G$_4$S was expressed with a cleavable hexahistidine tag and immobilized metal affinity chromatography (IMAC). After elution from the Ni-NTA column, the protein was incubated at room temperature overnight with the cysteine protease from Tobacco Etch Virus (TEV) and 1 mM DTT. A second Ni-NTA column is used to remove the hexahistidine tag, His-tagged-TEV protease. A cation exchange step is used to remove several protein contaminants. By SDS-PAGE, the desired product is nearly homogeneous (FIG. 36).

Figure 50:
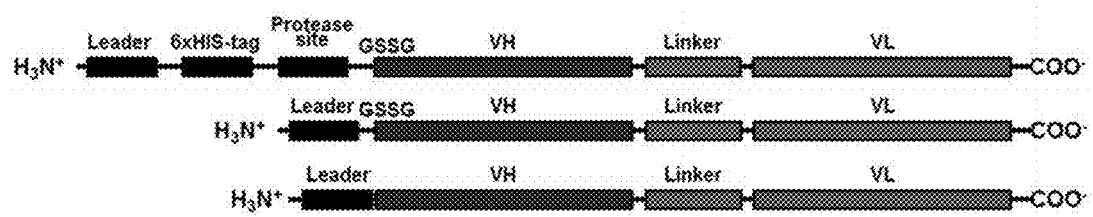
FIG. 50 shows two new variants that remove the hexahistidine tag and TEV protease recognition sequence. The N-terminus begins with the PelB leader sequence to direct the disulfide-containing protein to the periplasm. Upon leader sequence cleavage by the endogenous signal peptidase from *E. coli*, the final proteins begins with amino acids, QVQ.

Two new variants were cloned that remove the hexahistidine tag and TEV protease recognition sequence. The original 3E8.G$_4$S leaves a small GSSG linker at the N-terminus. One variant begins GSSG-QVQ . . . , and the second that begins with the native QVQ . . . . The GSSG linker did not affect the folding, stability, function, or expression of 3E8.G$_4$S. As shown in FIG. 50, the N-terminus begins with the PelB leader sequence to direct the disulfide-containing protein to the periplasm. Upon leader sequence cleavage by the endogenous signal peptidase from *E. coli*, the final proteins begins with amino acids, QVQ.

The first purification step to extract 3E8.G$_4$S from the cleared lysate is Protein L chromatography. The purification procedure involves using a 1 mL or 5 mL GE Healthcare HiTrap Protein L column. The cleared lysate can be diluted 1:1 in Protein L binding buffer (20 mM sodium phosphate, 150 mM sodium chloride, pH 7.2), or dialyzes the cleared lysate into Protein L binding buffer (4×1 L exchanges for 30 minutes each—assume ~25 mL sample). These two procedures bound the column nearly quantitatively.

Figure 51:
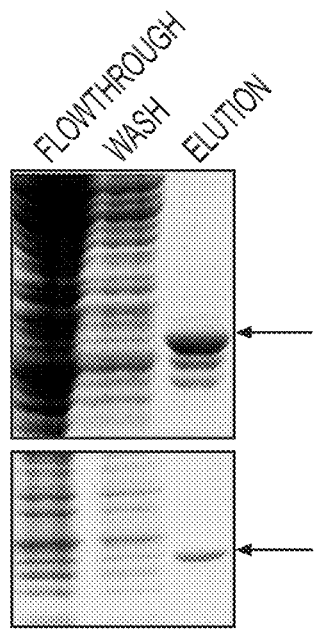
FIG. 51 shows the purification steps used to extract 3E8.G$_4$S from the cleared lysate is Protein L chromatography. When the hexahistidine tag and TEV protease recognition sequence was removed from the open reading frame (QVQ variant), the copurifying bands were absent. Protein L has produced nearly quantitative purification and near-homogeneity by SDS-PAGE (>95%).

FPLC Procedure (Assume 1 L Expression from Shake Flask):

The Protein L column was first equilibrated with 5 column volumes (CV) of Protein L binding buffer. Next, the sample was loaded at 1 mL min$^{-1}$ before washing with 10 CVs Protein L binding buffer (1 mL min$^{-1}$ washing). Next, the sample was eluted with Protein L elution buffer (100 mM glycine pH 3). The SDS-PAGE gel shown in FIG. 51 shows the flow-through, wash, and elution of the hexahistidine tagged 3E8.G$_4$S. Note that the desired antibody fragment is arrowed and that several proteolytic products or copurifying contaminates are bound and eluted from the Protein L column. These bands are able to be removed by ion exchange chromatography. When the hexahistidine tag and TEV protease recognition sequence was removed from the open reading frame (QVQ variant), the copurifying bands were absent (FIG. 51). Protein L has produced nearly quantitative purification and near-homogeneity by SDS-PAGE (>95%).

Example 8: Biophysical Characterization

Quaternary Structure.

The length of the amino acid linker that connects the variable heavy domain and variable light domain of antibody fragments determines the quaternary structure of the protein. In general, longer linker lengths lead to scFvs, while those shorter than ~12 amino acids lead to diabodies, triabodies, tetrabodies, etc. Based on animal studies (PK, BioD, and imaging), in addition to biophysical studies, the best 3E8 linker for imaging and diagnostics with $^{123}$I and $^{124}$I is GGGGS (G4S).

Figure 52:
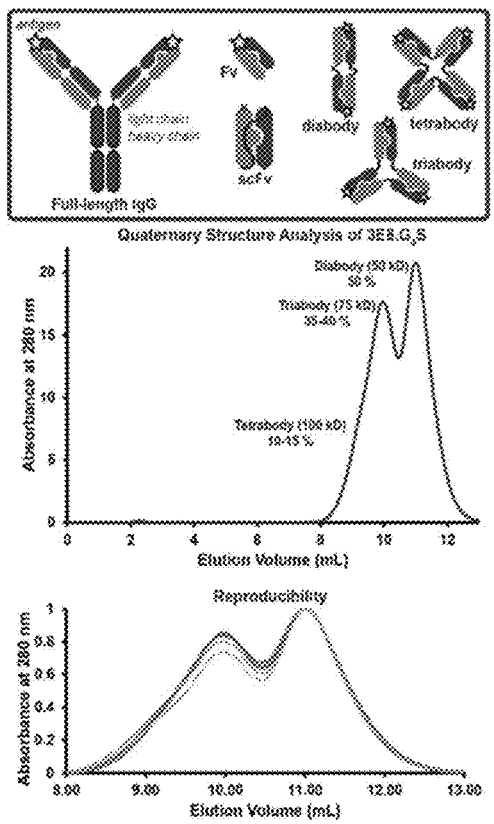
FIG. 52 shows twelve individual transformants were selected, expressed, purified, and characterized by Superdex 75. All preparations show diabody, triabody, and tetrabody features with less than 10% separating the extremes (+/−5% difference from the average).

To determine the quaternary structure of 3E8.G4S, gel filtration (GE Superdex 75 media) and analytical ultracentrifugation (Beckman) was performed. By gel filtration, two peaks were seen with a higher molecular weight shoulder suggesting three species. The same observation was reported by analytical ultracentrifugation (AUC). Here, AUC was performed at 1 mg mL$^{-1}$. Fits were performed using Beckman's software and confirmed with SedFit. The absorbance and interference data from AUC was fit to determine the molecular weight and distribution of the three species. 3E8.G$_4$S exists as a stable formulation of diabody (50 kD), triabody (75 kD), and tetrabody (100 kD). The distribution is 50% diabody, 35-40% triabody, and 10-15% tetrabody (FIG. 52). No molecular weight species of larger (including aggregates) or smaller composition were identified by gel filtration of analytical ultracentrifugation.

To test the consistency of the material produced by *E. coli*, twelve individual transformants were selected, expressed, purified, and characterized by Superdex 75 (FIG. 52). All preparations show diabody, triabody, and tetrabody features with less than 10% separating the extremes (+/−5% difference from the average).

Example 9: Molecule Characterization

Pharmacokinetics

Figure 53:
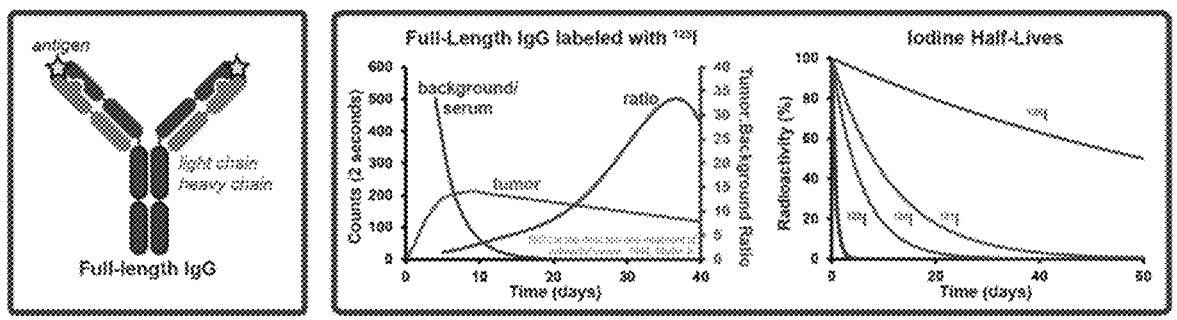
FIG. 53 shows full-length antibodies have long serum lifetimes due to their large size (~160 kD) and cellular uptake via neonatal Fc receptors. Shown are full-length IgG labeled with $^{125}$I, and iodine half-lives.
Figure 54:
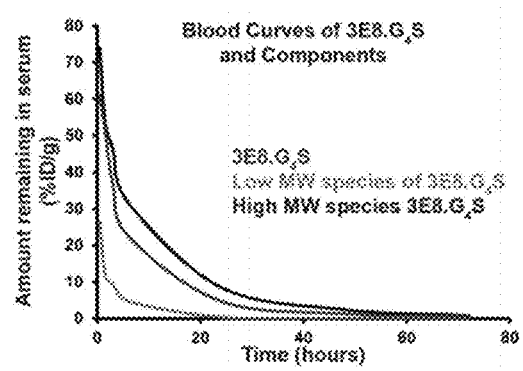
FIG. 54 shows blood curves. 3E8.G$_4$S radiolabels well with iodine using the standard Iodogen method (>70%, and as high as 95%).

3E8.G$_4$S exhibited ideal pharmacokinetics as shown in FIGS. 53 and 54. At 24 hours and longer, less than 5% background is identified in serum, and unlike scFv, there is adequate circulation time to ensure interaction and binding with tumors. All blood curves were performed in healthy mice. Note that 3E8.G$_4$S radiolabels well with iodine using the standard Iodogen method (≥70%, and as high as 95%).

Biodistribution

Figure 55:
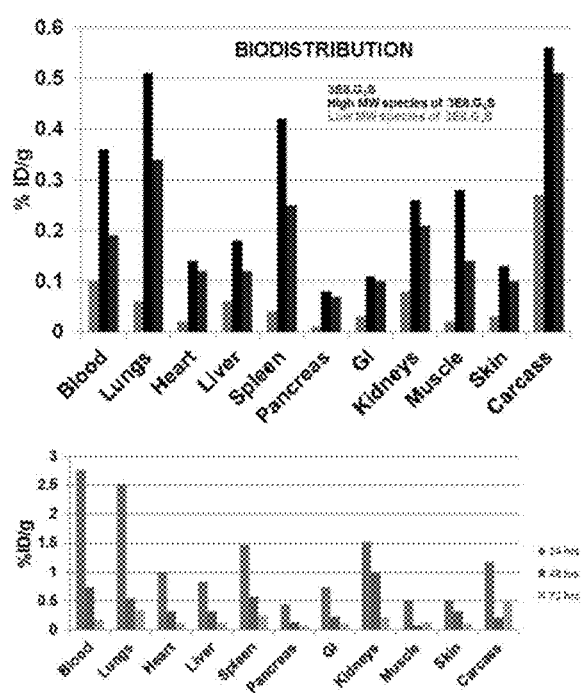
FIG. 55 shows the biodistribution of 3E8.G$_4$S in mice. The approximate tumor:tissue ratios of blood (9:1), liver (20:1), kidneys (7:1), GI (29:1) are shown. Based on these analyses, 3E8.G$_4$S is ideal for imaging of a broad range of adenocarcinomas, as no tissue significantly accumulates 3E8.G4S.

To better understand the biodistribution of 3E8.G$_4$S in mice, the animals were sacrificed at 72 hours and organ systems were isolated for further analysis. As can be seen in FIG. 55, no tissue significantly accumulates 3E8.G$_4$S.

To better understand the biodistribution of the molecule, necropsy studies of mice were performed at two additional time points. Note that the 48 hour time point was in nude xenograft mice. For these animals the average tumor uptake was 7% ID/g. The approximate tumor:tissue ratios of blood (9:1), liver (20:1), kidneys (7:1), GI (29:1) are shown in FIG. 55. Based on these analyses, 3E8.G$_4$S is ideal for imaging of a broad range of adenocarcinomas.

Imaging, $^{124}$I-3E8.G4S Via PET

Figure 56:
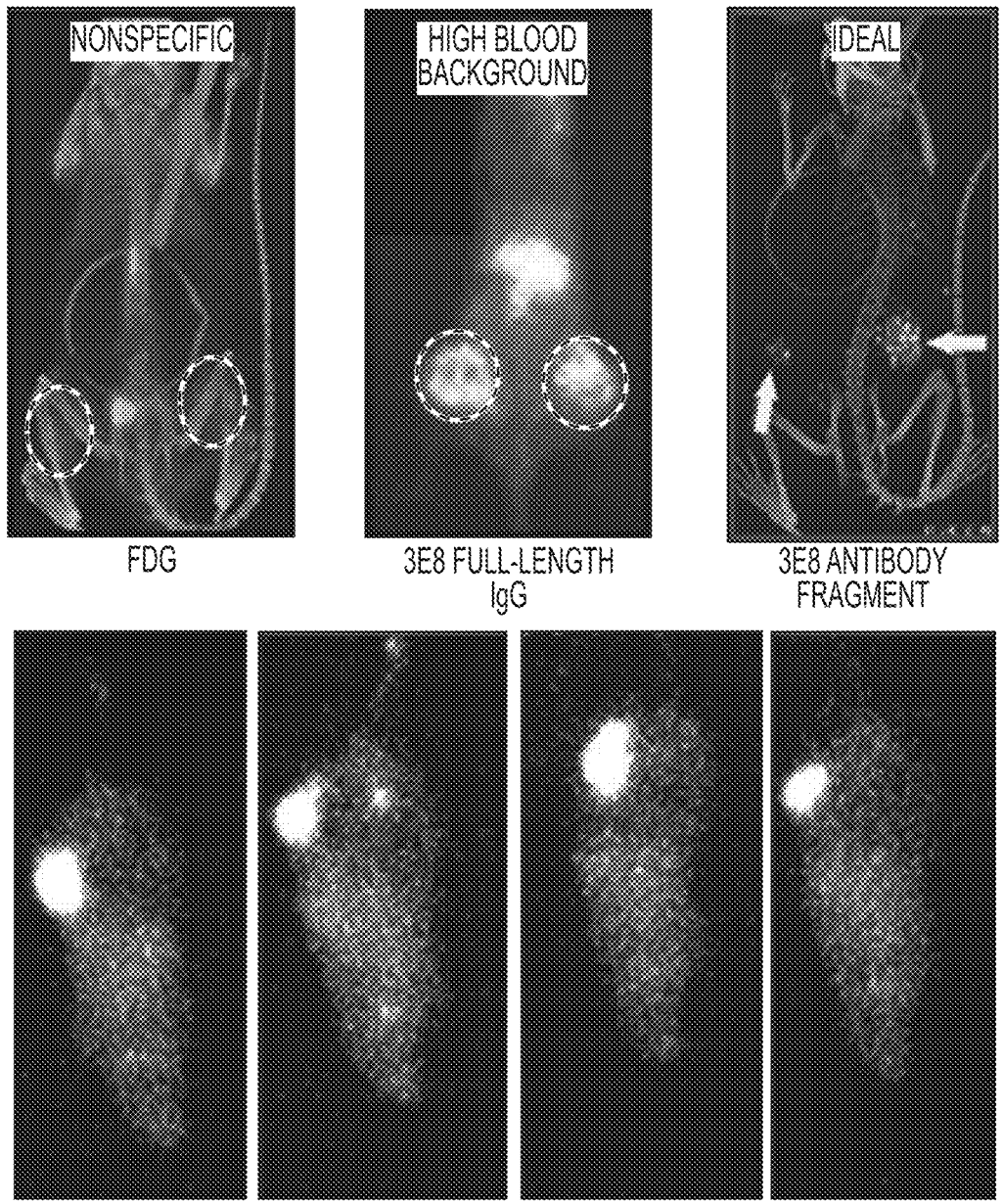
FIG. 56 shows xenograft mice implanted with human colon adenocarcinoma tumors (LS-174T cells), imaged with $^{18}$FDG, full-length 3E8 IgG, and a 3E8 antibody fragment—specifically a component of 3E8.G$_4$S. As expected, the $^{18}$FDG mouse shows nonspecific uptake of the radiotracer and poor labeling of the two implanted tumors on the left and right flanks. 4 mice imaged at 48 hours with 3E8.G$_4$S are also shown.

The current state-of-the-art in cancer imaging is $^{18}$FDG. This imaging modality suffers from high background, numerous false positives, and poor tumor: background ratios for handheld probes. Xenograft mice implanted with human colon adenocarcinoma tumors (LS-174T cells) were imaged with $^{18}$FDG, full-length 3E8 IgG, and a 3E8 antibody fragment—specifically a component of 3E8.G$_4$S. As expected, the $^{18}$FDG mouse shows nonspecific uptake of the radiotracer and poor labeling of the two implanted tumors on the left and right flanks. The full-length IgG labels the tumors well, but at 24 hours still resides in the serum leading to high background. The smaller fragment of 3E8 is ideal. It strongly labels both tumors including a small (1 mm) tumor on the left flank, and the background is minimal. In FIG. 56, 4 mice imaged at 48 hours with 3E8.G$_4$S are shown. These animals have single tumors on the right flanks. Here, the only background seen is a minimal amount in the bladder and thyroid. Human patients have the thyroids blocked with cold iodine and catherization empty the radioactivity from the bladder prior to imaging and surgery. 3E8.G4S exhibits the higher % ID/g for tumor than previously characterized diabodies.

Biophysical Characterization

Quaternary Structure.

The length of the amino acid linker that connects the variable heavy domain and variable light domain of antibody fragments determines the quaternary structure of the protein. In general, longer linker lengths lead to scFvs, while those shorter than ~12 amino acids lead to diabodies, triabodies, tetrabodies, etc. Based on animal studies (PK, BioD, and imaging), in addition to biophysical studies, the best 3E8 linker for imaging and diagnostics with $^{123}$I and $^{124}$I is GGGGS (G$_4$S).

Figure 57:
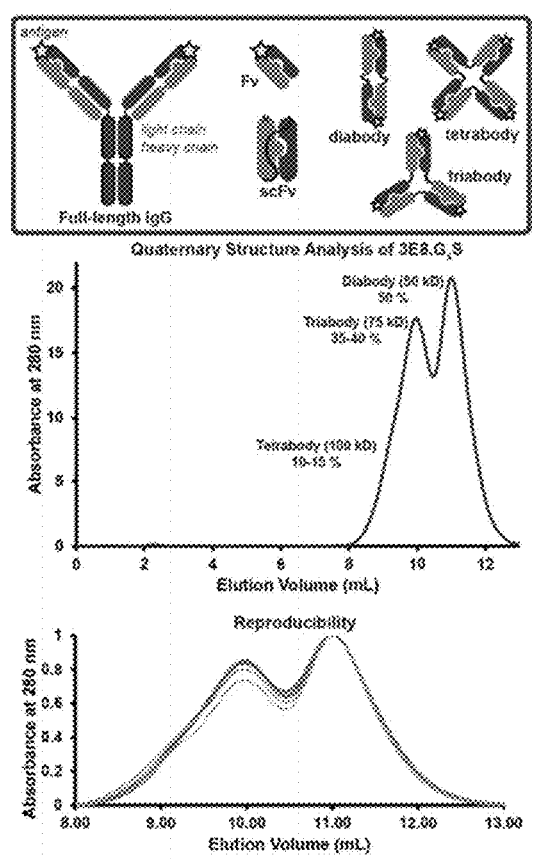
FIG. 57 shows the results of gel filtration, showing two peaks with a higher molecular weight shoulder showing three species.

To determine the quaternary structure of 3E8.G4S, gel filtration (GE Superdex 75 media) and analytical ultracentrifugation (Beckman) was performed. By gel filtration, two peaks are seen with a higher molecular weight shoulder showing three species (FIG. 57). The same observation was reported by analytical ultracentrifugation (AUC). The absorbance and interference data from AUC was fit to determine the molecular weight and distribution of the three species. 3E8.G$_4$S exists as a stable formulation of diabody (50 kD), triabody (75 kD), and tetrabody (100 kD). The distribution is 50% diabody, 35-40% triabody, and 10-15 tetrabody. No molecular weight species of larger (including aggregates) or smaller composition were identified by gel filtration of analytical ultracentrifugation.

To better understand the 3E8.G4S formulation, the low (~50 kD) and high (>75 kD) molecular weight species were isolated by gel filtration chromatography. Note that this separation is not amenable to process-scale production. The full formulation and components were studied individually. The pharmacokinetics, biodistribution, and imaging of the diabody have been previously shown above (High MW species of 3E8.G$_4$S and Low MW species of 3E8.G$_4$S in graphs). As expected, the High MW species produce longer serum half-lives than the full formulation and Low MW species. As a consequence, the biodistributions are slightly higher as well. It is important to note that the larger molecular weight species do not aggregate or accumulate in the liver. The lower molecular weight species are rapidly excreted from the serum, but still interact with tumor; however, the % ID/g is less than the full formulation. The full formulation and separated components were studied by gel filtration at days 0, 71, and 107. The distribution of the full formulation did not change with time, and the separated components maintained their identity post fractionation.

To test the consistency of the material produced by *E. coli*, twelve individual transformants were selected, expressed, purified, and characterized by Superdex 75 (bottom graph above). All preparations show diabody, triabody, and tetrabody features with less than 10% separating the extremes (+/−5% difference from the average).

Binding.

The binding activity of 3E8.G$_4$S and its components were determined by surface plasmon resonance (SPR). Here, bovine submaxillary mucin (TAG-72+), was adhered to a CM5 sensor chip, and antibody fragment was flowed over the immobilized antigen at varying concentrations. We calculated a binding constant ($K_D$) of 3.6 nM for the 3E8.G$_4$S, and 1.6 nM and 9 nM for the High MW species and Low MW species, respectively. All components of the formulation are active ingredients with single-digit nM binding constant. Note that 3.6 nM binds approximately 10 fold better than CC49 and 100-fold better than B72.3. CC49 and B72.3 are full-length antibodies that have been shown previously to bind TAG-72. 3E8 binds significantly tighter and is more thermally stable than these molecules.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

REFERENCES

1. Jemal, A., Bray, F., Center, M. M., Ferlay, J., Ward, E. & Forman, D. (2011). Global cancer statistics. *CA Cancer J Clin* 61, 69-90.
2. Sun, D., Bloomston, M., Hinkle, G., Al-Saif, O. H., Hall, N. C., Povoski, S. P., Arnold, M. W. & Martin, E. W., Jr. (2007). Radioimmunoguided surgery (RIGS), PET/CT image-guided surgery, and fluorescence image-guided surgery: past, present, and future. *J Surg Oncol* 96, 297-308.
3. Thor, A., Ohuchi, N., Szpak, C. A., Johnston, W. W. & Schlom, J. (1986). Distribution of oncofetal antigen tumor-associated glycoprotein-72 defined by monoclonal antibody B72.3. *Cancer Res* 46, 3118-24.
4. Thor, A., Viglione, M. J., Muraro, R., Ohuchi, N., Schlom, J. & Gorstein, F. (1987). Monoclonal antibody B72.3 reactivity with human endometrium: a study of normal and malignant tissues. *Int J Gynecol Pathol* 6, 235-47.
5. Yokota, T., Milenic, D. E., Whitlow, M. & Schlom, J. (1992). Rapid tumor penetration of a single-chain Fv and comparison with other immunoglobulin forms. *Cancer Res* 52, 3402-8.
6. Colcher, D., Pavlinkova, G., Beresford, G., Booth, B. J. & Batra, S. K. (1999). Single-chain antibodies in pancreatic cancer. *Ann NY Acad Sci* 880, 263-80.
7. Yoon, S. O., Lee, T. S., Kim, S. J., Jang, M. H., Kang, Y. J., Park, J. H., Kim, K. S., Lee, H. S., Ryu, C. J., Gonzales, N. R., Kashmiri, S. V., Lim, S. M., Choi, C. W. & Hong, H. J. (2006). Construction, affinity maturation, and biological characterization of an anti-tumor-associated glycoprotein-72 humanized antibody. *J Biol Chem* 281, 6985-92.
8. Bird, R. E., Hardman, K. D., Jacobson, J. W., Johnson, S., Kaufman, B. M., Lee, S. M., Lee, T., Pope, S. H., Riordan, G. S. & Whitlow, M. (1988). Single-chain antigen-binding proteins. *Science* 242, 423-6.
9. Sandhu, J. S. (1992). Protein engineering of antibodies. *Crit Rev Biotechnol* 12, 437-62.
10. *Pini*, A. & Bracci, L. (2000). Phage display of antibody fragments. *Curr Protein Pept Sci* 1, 155-69.
11. Yang, K., Basu, A., Wang, M., Chintala, R., Hsieh, M. C., Liu, S., Hua, J., Zhang, Z., Zhou, J., Li, M., Phyu, H., Petti, G., Mendez, M., Janjua, H., Peng, P., Longley, C., Borowski, V., Mehlig, M. & Filpula, D. (2003). Tailoring structure-function and pharmacokinetic properties of single-chain Fv proteins by site-specific PEGylation. *Protein Eng* 16, 761-70.
12. Muraro, R., Kuroki, M., Wunderlich, D., Poole, D. J., Colcher, D., Thor, A., Greiner, J. W., Simpson, J. F., Molinolo, A., Noguchi, P. & et al. (1988). Generation and characterization of B72.3 second generation monoclonal antibodies reactive with the tumor-associated glycoprotein 72 antigen. *Cancer Res* 48, 4588-96.
13. Colcher, D., Minelli, M. F., Roselli, M., Muraro, R., Simpson-Milenic, D. & Schlom, J. (1988). Radioimmunolocalization of human carcinoma xenografts with B72.3 second generation monoclonal antibodies. *Cancer Res* 48, 4597-603.
14. Divgi, C. R., Scott, A. M., Dantis, L., Capitelli, P., Siler, K., Hilton, S., Finn, R. D., Kemeny, N., Kelsen, D., Kostakoglu, L. & et al. (1995). Phase I radioimmunotherapy trial with iodine-131-CC49 in metastatic colon carcinoma. *J Nucl Med* 36, 586-92.
15. Kashmiri, S. V., Shu, L., Padlan, E. A., Milenic, D. E., Schlom, J. & Hand, P. H. (1995). Generation, characterization, and in vivo studies of humanized anticarcinoma antibody CC49. *Hybridoma* 14, 461-73.
16. Denzin, L. K., Whitlow, M. & Voss, E. W., Jr. (1991). Single-chain site-specific mutations of fluorescein-amino acid contact residues in high affinity monoclonal antibody 4-4-20. *J Biol Chem* 266, 14095-103.
17. Prachayasittikul, V., Isarankura-Na-Ayudhya, C., Tantimongcolwat, T., Nantasenamat, C. & Galla, H. J. (2007). EDTA-induced membrane fluidization and destabilization: biophysical studies on artificial lipid membranes. *Acta Biochim Biophys Sin (Shanghai)* 39, 901-13.
18. Pavlinkova, G., Beresford, G. W., Booth, B. J., Batra, S. K. & Colcher, D. (1999). Pharmacokinetics and biodistribution of engineered single-chain antibody constructs of MAb CC49 in colon carcinoma xenografts. *J Nucl Med* 40, 1536-46.
19. Bork, P., Holm, L. & Sander, C. (1994). The immunoglobulin fold. Structural classification, sequence patterns and common core. *J Mol Biol* 242, 309-20.
20. Kjeldsen, T., Clausen, H., Hirohashi, S., Ogawa, T., Iijima, H. & Hakomori, S. (1988). Preparation and characterization of monoclonal antibodies directed to the tumor-associated O-linked sialosyl-2-6 alpha-N-acetylgalactosaminyl (sialosyl-Tn) epitope. *Cancer Res* 48, 2214-20.
21. Senisterra, G. A. & Finerty, P. J., Jr. (2009). High throughput methods of assessing protein stability and aggregation. *Mol Biosyst* 5, 217-23.
22. Lavinder, J. J., Hari, S. B., Sullivan, B. J. & Magliery, T. J. (2009). High-throughput thermal scanning: a general, rapid dye-binding thermal shift screen for protein engineering. *J Am Chem Soc* 131, 3794-5.
23. Kortt, A. A., Dolezal, O., Power, B. E., Hudson, P. J. (2001). Dimeric and trimeric antibodies: high avidity scFv for cancer targeting. Biomol Eng 18, 95-108.
24. Pini, A. & Bracci, L. (2000). Phage display of antibody fragments. *Curr Protein Pept Sci* 1, 155-69.
25. Durani, V., Sullivan, B. J., Magliery, T. J. (2012) Simplifying protein expression with ligation-free, traceless and tag-switching plasmids. Protein Expr Purif 85, 9-17.
26. Miroux, B., Walker, J. E. (1996) Over-production of proteins in *Escherichia coli:* mutant hosts that allow synthesis of some membrane proteins and globular proteins at high levels. J Mol Biol 260, 289-98.
27. Chen, C., Constantinou, A., Deonarain, M. (2011) Modulating antibody pharmacokinetics using hydrophilic polymers. Exper Opin Drug Deliv 8, 1221-36.
28. Veronese, F. M., Mero, A. (2008) The impact of PEGylation on biological therapies. BioDrugs 22, 315-29.
29. Goel, A., Colcher, D., Baranowska-Kortylewicz, et al. (2000) Genetically engineered tetravalent single-chain Fv of the pancarcinoma monoclonal antibody CC49: Improved biodistribution and potential for therapeutic application. Cancer Res 60, 6964-71.
30. Bailey, G. S. (1996) The Iodogen Method for Radiolabeling Protein, Humana Press Inc., Totowa, N.J.
31. Paus, E. B., O.; Nustad,K. (1982) Radioiodination of proteins with the Iodogen method, International Atomic Energy Agency, Vienna.
32. Maddalena, M. E., Fox, J., Chen, J., Feng, W., Cagnolini, A., Linder, K. E., Tweedle, M. F., Nunn, A. D., and Lantry, L. E. (2009) 177Lu-AMBA biodistribution, radiotherapeutic efficacy, imaging, and autoradiography in prostate cancer models with low GRP-R expression. Journal of nuclear medicine: official publication, Society of Nuclear Medicine 50, 2017-24
33. Wedeking, P., and Tweedle, M. (1988) Comparison of the Biodistribution of Gd-153-Labeled Gd(Dtpa)2-, Gd(Dota)-, and Gd(Acetate)N in Mice. Nuclear medicine and biology 15, 395-402.

What is claimed is:

1. A method for in vitro immunodetection of TAG-72-expressing cancer cells comprising a step of contacting the cancer cells with an antibody fragment which specifically binds tumor-associated glycoprotein 72 (TAG-72), wherein the antibody fragment comprises an amino acid sequence with 98% or more identity to SEQ ID NO: 13, 33, 35, 37, 39, 41, 43, or 45, wherein said antibody fragment comprises complementarity determining regions (CDRs), wherein said CDRs comprise amino acid residues 53-57, 72-88, 122-126, 166-182, 198-204, and 237-245 of SEQ ID NO: 13; residues 76-80, 95-111, 144-149, 189-205, 221-227, and 260-268 of SEQ ID NO: 33; residues 76-80, 95-111, 144-149, 209-225, 241-247, and 280-288 of SEQ ID NO: 35; residues 76-80, 95-111, 144-149, 204-220, 236-242, and 275-283 of SEQ ID NO: 37; residues 76-80, 95-111, 144-149, 199-215, 231-237, and 270-278 of SEQ ID NO: 39; residues 76-80, 95-111, 144-149, 188-204, 220-226, and 259-267 of SEQ ID NO: 41; residues 76-80, 95-111, 144-149, 188-204, 220-226, and 259-267 of SEQ ID NO: 43; and residues 76-80, 95-111, 144-149, 189-205, 221-227, and 260-268 of SEQ ID NO: 45; or wherein the antibody fragment comprises SEQ ID NOS: 15, 17, 19, 21, 23, 25, 27, 29, or 31.

2. The method of claim 1, wherein the antibody fragments are bound to a solid support.

3. The method of claim 1, wherein the antibody fragment specifically binds to a sialyl-Tn epitope of TAG-72.

4. The method of claim 1, wherein the antibody fragment comprises a heavy chain variable region comprising SEQ ID NO: 10, and a light chain variable region comprising SEQ ID NO: 11.

5. The method of claim 1, wherein said antibody fragment has an antigen binding affinity for sialyl-Tn which is at least 25% that of 3E8.

6. A method of in vivo immunodetection of TAG-72-expressing cancer cells in a mammal comprising a step of administering to the mammal a diagnostically effective amount of an antibody fragment which specifically binds tumor-associated glycoprotein 72 (TAG-72), wherein the antibody fragment comprises an amino acid sequence with 9-54 98% or more identity to SEQ ID NO: 13, 33, 35, 37, 39, 41, 43, or 45, wherein said antibody fragment comprises complementarity determining regions (CDRs), wherein said CDRs comprise amino acid residues 53-57, 72-88, 122-126, 166-182, 198-204, and 237-245 of SEQ ID NO: 13; residues 76-80, 95-111, 144-149, 189-205, 221-227, and 260-268 of SEQ ID NO: 33; residues 76-80, 95-111, 144-149, 209-225, 241-247, and 280-288 of SEQ ID NO: 35; residues 76-80, 95-111, 144-149, 204-220, 236-242, and 275-283 of SEQ ID NO: 37; residues 76-80, 95-111, 144-149, 199-215, 231-237, and 270-278 of SEQ ID NO: 39; residues 76-80, 95-111, 144-149, 188-204, 220-226, and 259-267 of SEQ ID NO: 41; residues 76-80, 95-111, 144-149, 188-204, 220-226, and 259-267 of SEQ ID NO: 43; and residues 76-80, 95-111, 144-149, 189-205, 221-227, and 260-268 of SEQ ID NO: 45; or wherein the antibody fragment comprises SEQ ID NOS: 15, 17, 19, 21, 23, 25, 27, 29, or 31.

7. The method of claim 6, wherein said immunodetection is in vivo tumor imaging.

8. The method of claim 6, wherein the antibody fragment specifically binds to a sialyl-Tn epitope of TAG-72.

9. The method of claim 6, wherein the antibody fragment comprises a heavy chain variable region comprising SEQ ID NO: 10, and a light chain variable region comprising SEQ ID NO: 11.

10. The method of claim 6, wherein said antibody fragment has an antigen binding affinity for sialyl-Tn which is at least 25% that of 3E8.

* * * * *

```
                         SEQUENCE LISTING

<160> NUMBER OF SEQ ID NOS: 48

<210> SEQ ID NO 1
<211> LENGTH: 298
<212> TYPE: PRT
<213> ORGANISM: Artificial Sequence
<220> FEATURE:
<223> OTHER INFORMATION: 3E8.scFv

<400> SEQUENCE: 1

Met Lys Tyr Leu Leu Pro Thr Ala Ala Ala Gly Leu Leu Leu Ala
1               5                   10                  15

Ala Gln Pro Ala Met Ala Ala His His His His His Gly Ser Ser
                20                  25                  30

Gly Gly Gly Glu Asn Leu Tyr Phe Gln Gly Ser Ser Gly Asp Ile Val
            35                  40                  45

Met Thr Gln Ser Pro Asp Ser Leu Ala Val Ser Leu Gly Glu Arg Ala
    50                  55                  60

Thr Ile Asn Cys Lys Ser Ser Gln Ser Val Leu Tyr Ser Ser Asn Asn
65                  70                  75                  80

Lys Asn Tyr Leu Ala Trp Tyr Gln Gln Lys Pro Gly Gln Pro Pro Lys
                85                  90                  95

Leu Leu Ile Tyr Trp Ala Ser Thr Arg Glu Ser Gly Val Pro Asp Arg
            100                 105                 110

Phe Ser Gly Ser Gly Ser Gly Thr Asp Phe Thr Leu Thr Ile Ser Ser
```

```
                115                 120                 125
Leu Gln Ala Glu Asp Val Ala Val Tyr Tyr Cys Gln Gln Tyr Tyr Ser
            130                 135                 140

Tyr Pro Leu Thr Phe Gly Gly Gly Thr Lys Val Glu Ile Lys Leu Ser
145                 150                 155                 160

Ala Asp Asp Ala Lys Lys Asp Ala Ala Lys Lys Asp Asp Ala Lys Lys
                165                 170                 175

Asp Asp Ala Lys Lys Asp Leu Gln Val Gln Leu Val Gln Ser Gly Ala
            180                 185                 190

Glu Val Lys Lys Pro Gly Ala Ser Val Lys Val Ser Cys Lys Ala Ser
                195                 200                 205

Gly Tyr Thr Phe Thr Asp His Ala Ile His Trp Val Arg Gln Ala Pro
210                 215                 220

Gly Gln Arg Leu Glu Trp Met Gly Tyr Phe Ser Pro Gly Asn Asp Asp
225                 230                 235                 240

Phe Lys Tyr Ser Gln Lys Phe Gln Gly Arg Val Thr Ile Thr Ala Asp
                245                 250                 255

Lys Ser Ala Ser Thr Ala Tyr Met Glu Leu Ser Ser Leu Arg Ser Glu
            260                 265                 270

Asp Thr Ala Val Tyr Tyr Cys Ala Arg Ser Trp Ile Met Gln Tyr Trp
            275                 280                 285

Gly Gln Gly Thr Leu Val Thr Val Ser Ser
            290                 295

<210> SEQ ID NO 2
<211> LENGTH: 299
<212> TYPE: PRT
<213> ORGANISM: Artificial Sequence
<220> FEATURE:
<223> OTHER INFORMATION: 3E8.scFv.Cys

<400> SEQUENCE: 2

Met Lys Tyr Leu Leu Pro Thr Ala Ala Ala Gly Leu Leu Leu Leu Ala
1               5                   10                  15

Ala Gln Pro Ala Met Ala Ala His His His His His His Gly Ser Ser
            20                  25                  30

Gly Gly Gly Glu Asn Leu Tyr Phe Gln Gly Ser Ser Gly Asp Ile Val
        35                  40                  45

Met Thr Gln Ser Pro Asp Ser Leu Ala Val Ser Leu Gly Glu Arg Ala
    50                  55                  60

Thr Ile Asn Cys Lys Ser Gln Ser Val Leu Tyr Ser Ser Asn Asn
65                  70                  75                  80

Lys Asn Tyr Leu Ala Trp Tyr Gln Gln Lys Pro Gly Gln Pro Pro Lys
                85                  90                  95

Leu Leu Ile Tyr Trp Ala Ser Thr Arg Glu Ser Gly Val Pro Asp Arg
            100                 105                 110

Phe Ser Gly Ser Gly Ser Gly Thr Asp Phe Thr Leu Thr Ile Ser Ser
        115                 120                 125

Leu Gln Ala Glu Asp Val Ala Val Tyr Tyr Cys Gln Gln Tyr Tyr Ser
    130                 135                 140

Tyr Pro Leu Thr Phe Gly Gly Gly Thr Lys Val Glu Ile Lys Leu Ser
145                 150                 155                 160

Ala Asp Asp Ala Lys Lys Asp Ala Ala Lys Lys Asp Asp Ala Lys Lys
                165                 170                 175

Asp Asp Ala Lys Lys Asp Leu Gln Val Gln Leu Val Gln Ser Gly Ala
```

```
            180                 185                 190
Glu Val Lys Lys Pro Gly Ala Ser Val Lys Val Ser Cys Lys Ala Ser
        195                 200                 205

Gly Tyr Thr Phe Thr Asp His Ala Ile His Trp Val Arg Gln Ala Pro
        210                 215                 220

Gly Gln Arg Leu Glu Trp Met Gly Tyr Phe Ser Pro Gly Asn Asp Asp
225                 230                 235                 240

Phe Lys Tyr Ser Gln Lys Phe Gln Gly Arg Val Thr Ile Thr Ala Asp
                245                 250                 255

Lys Ser Ala Ser Thr Ala Tyr Met Glu Leu Ser Ser Leu Arg Ser Glu
            260                 265                 270

Asp Thr Ala Val Tyr Tyr Cys Ala Arg Ser Trp Ile Met Gln Tyr Trp
        275                 280                 285

Gly Gln Gly Thr Leu Val Thr Val Ser Ser Cys
        290                 295
```

<210> SEQ ID NO 3
<211> LENGTH: 22
<212> TYPE: PRT
<213> ORGANISM: Artificial Sequence
<220> FEATURE:
<223> OTHER INFORMATION: Artificial Construct

<400> SEQUENCE: 3

```
Met Lys Tyr Leu Leu Pro Thr Ala Ala Ala Gly Leu Leu Leu Leu Ala
1               5                   10                  15

Ala Gln Pro Ala Met Ala
            20
```

<210> SEQ ID NO 4
<211> LENGTH: 19
<212> TYPE: PRT
<213> ORGANISM: Artificial Sequence
<220> FEATURE:
<223> OTHER INFORMATION: Artificial Construct

<400> SEQUENCE: 4

```
Ala His His His His His His Gly Ser Ser Gly Gly Gly Glu Asn Leu
1               5                   10                  15

Tyr Phe Gln
```

<210> SEQ ID NO 5
<211> LENGTH: 4
<212> TYPE: PRT
<213> ORGANISM: Artificial Sequence
<220> FEATURE:
<223> OTHER INFORMATION: Artificial Construct

<400> SEQUENCE: 5

```
Gly Ser Ser Gly
1
```

<210> SEQ ID NO 6
<211> LENGTH: 25
<212> TYPE: PRT
<213> ORGANISM: Artificial Sequence
<220> FEATURE:
<223> OTHER INFORMATION: Artificial Construct

<400> SEQUENCE: 6

```
Leu Ser Ala Asp Asp Ala Lys Lys Asp Ala Ala Lys Lys Asp Asp Ala
1               5                   10                  15
```

Lys Lys Asp Asp Ala Lys Lys Asp Leu
            20                  25

<210> SEQ ID NO 7
<211> LENGTH: 906
<212> TYPE: DNA
<213> ORGANISM: artificial sequence
<220> FEATURE:
<223> OTHER INFORMATION: 3E8.scFv

<400> SEQUENCE: 7

| catatgaaat | atctgttacc | tactgctgct | gcgggcctgc | tattattagc | ggcacaacca | 60 |
| gcaatggcgg | cgcatcatca | tcatcatcat | gggtcctcgg | gcggtggcga | aaatctgtat | 120 |
| tttcagggta | gcagcggcga | tattgtgatg | acccagagcc | cggatagttt | ggccgttagc | 180 |
| ctgggcgaac | gtgcgacgat | taattgcaag | agcagccaga | gcgtgcttta | cagcagcaac | 240 |
| aataagaatt | acctggcgtg | gtatcagcaa | aaacccggcc | agccgccgaa | acttttgatt | 300 |
| tattgggcga | gcacccgtga | aagcggcgtg | ccggatcgtt | tctcgggctc | aggcagcggg | 360 |
| accgatttta | cgctgaccat | cagcagcctt | caggcggagg | atgtcgcggt | gtactactgc | 420 |
| cagcagtatt | acagctatcc | gttgaccttt | ggggaggcc | ccaaagtgga | gatcaaactg | 480 |
| agcgcggatg | atgctaagaa | agatgcggcg | aagaaggacg | atgcgaaaaa | agacgacgca | 540 |
| aaaaaggatc | tgcaggtgca | gctggtgcag | tcgggtgcgg | aagtgaagaa | acctggggcg | 600 |
| tcggtgaaag | tgagctgcaa | agcgagcggc | tataccttta | ccgatcatgc | gattcattgg | 660 |
| gtgcgtcaag | cgccaggcca | gcgtctggaa | tggatgggct | attttccc | aggcaacgat | 720 |
| gatttcaagt | attcccagaa | gttccaaggg | cgcgtgacca | ttaccgccga | taaaagcgca | 780 |
| agcaccgcgt | atatggagct | gtccagcctg | cgtagcgaag | atacagcggt | ttactattgc | 840 |
| gcacggagct | ggattatgca | atactgggc | cagggcaccc | tggtgaccgt | gagcagctaa | 900 |
| ggatcc | | | | | | 906 |

<210> SEQ ID NO 8
<211> LENGTH: 909
<212> TYPE: DNA
<213> ORGANISM: artificial sequence
<220> FEATURE:
<223> OTHER INFORMATION: 3E8.scFv.Cys

<400> SEQUENCE: 8

| catatgaaat | atctgttacc | tactgctgct | gcgggcctgc | tattattagc | ggcacaacca | 60 |
| gcaatggcgg | cgcatcatca | tcatcatcat | gggtcctcgg | gcggtggcga | aaatctgtat | 120 |
| tttcagggta | gcagcggcga | tattgtgatg | acccagagcc | cggatagttt | ggccgttagc | 180 |
| ctgggcgaac | gtgcgacgat | taattgcaag | agcagccaga | gcgtgcttta | cagcagcaac | 240 |
| aataagaatt | acctggcgtg | gtatcagcaa | aaacccggcc | agccgccgaa | acttttgatt | 300 |
| tattgggcga | gcacccgtga | aagcggcgtg | ccggatcgtt | tctcgggctc | aggcagcggg | 360 |
| accgatttta | cgctgaccat | cagcagcctt | caggcggagg | atgtcgcggt | gtactactgc | 420 |
| cagcagtatt | acagctatcc | gttgaccttt | ggggaggcc | ccaaagtgga | gatcaaactg | 480 |
| agcgcggatg | atgctaagaa | agatgcggcg | aagaaggacg | atgcgaaaaa | agacgacgca | 540 |
| aaaaaggatc | tgcaggtgca | gctggtgcag | tcgggtgcgg | aagtgaagaa | acctggggcg | 600 |
| tcggtgaaag | tgagctgcaa | agcgagcggc | tataccttta | ccgatcatgc | gattcattgg | 660 |
| gtgcgtcaag | cgccaggcca | gcgtctggaa | tggatgggct | attttccc | aggcaacgat | 720 |

```
gatttcaagt attcccagaa gttccaaggg cgcgtgacca ttaccgccga taaaagcgca    780
agcaccgcgt atatggagct gtccagcctg cgtagcgaag atacagcggt ttactattgc    840
gcacggagct ggattatgca atactggggc agggcaccc tggtgaccgt gagcagctgt    900
taaggatcc                                                             909
```

```
<210> SEQ ID NO 9
<211> LENGTH: 48
<212> TYPE: PRT
<213> ORGANISM: Artificial Sequence
<220> FEATURE:
<223> OTHER INFORMATION: Artificial Construct

<400> SEQUENCE: 9

Met Lys Tyr Leu Leu Pro Thr Ala Ala Ala Gly Leu Leu Leu Leu Ala
1               5                   10                  15

Ala Gln Pro Ala Met Ala Ala His His His His His His Gly Ser Ser
            20                  25                  30

Gly Gly Gly Glu Asn Leu Tyr Phe Gln Gly Ser Ser Gly Asp Ile Val
        35                  40                  45

<210> SEQ ID NO 10
<211> LENGTH: 115
<212> TYPE: PRT
<213> ORGANISM: Artificial Sequence
<220> FEATURE:
<223> OTHER INFORMATION: VH Domain

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Ala Ile His Trp Val Arg Gln Ala Pro Gly Gln Arg Leu Glu Trp Met
        35                  40                  45

Gly Tyr Phe Ser Pro Gly Asn Asp Asp Phe Lys Tyr Ser Gln Lys Phe
    50                  55                  60

Gln Gly Arg Val Thr Ile Thr Ala Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Ile Met Gln Tyr Trp Gly Gln Gly Thr Leu Val Thr
            100                 105                 110

Val Ser Ser
        115

<210> SEQ ID NO 11
<211> LENGTH: 113
<212> TYPE: PRT
<213> ORGANISM: Artificial Sequence
<220> FEATURE:
<223> OTHER INFORMATION: VL Domain

<400> SEQUENCE: 11

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
```

```
                35                  40                  45
Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Tyr Pro Leu Thr Phe Gly Gly Gly Thr Lys Val Glu Ile
                100                 105                 110

Lys
```

<210> SEQ ID NO 12
<211> LENGTH: 813
<212> TYPE: DNA
<213> ORGANISM: Artificial Sequence
<220> FEATURE:
<223> OTHER INFORMATION: 3E8HL(GGGGS)his6.diabody

<400> SEQUENCE: 12

```
catatgaaat atttattgcc aacagcagcg gcaggtttgc tgcttttggc tgcgcagccg     60
gccatggccc aggttcagct ggtacaaagc ggagctgagg ttaaaaagcc aggtgcgtcg    120
gtaaaggtgt catgcaaggc ttctggatac acctttacgg accatgccat tcattgggtc    180
agacaagcac tggtcagcg cttagaatgg atggggtact tagtccggg caatgatgac     240
ttcaaatatt cgcaaaagtt tcaaggccgt gtgacaatta cggctgacaa atccagttct    300
actgcatata tggaactctc atcccttaga agcgaggata cagcagtcta ctattgtgcc    360
agatcatgga ttatgcagta ctggggccag gggacgcttg tgactgtatc atccggaggc    420
ggaggtagcg acatagtcat gacccaatcg cctgattcgt tggcggttag tctcggggag    480
cgggctacta taaactgcaa gtcttcccaa tctgtgcttt acagctcaaa taacaaaaat    540
tatttagctt ggtatcagca aaagccgggt cagccgccaa aactcctat atactgggcg    600
agcacgcggg agtctggggt accagacaga ttcagcggaa gtggcagtgg aacagatttc    660
accctgacaa tctcttcatt acaagcgaa gatgtcgcag tatattactg tcagcaatac    720
tatagttacc ctctcacttt cggtggggga accaaagttg aaatcaagag agccgcagca    780
ctggaacacc atcaccatca ccattaagga tcc                                 813
```

<210> SEQ ID NO 13
<211> LENGTH: 267
<212> TYPE: PRT
<213> ORGANISM: Artificial Sequence
<220> FEATURE:
<223> OTHER INFORMATION: 3E8HL(GGGGS)his6.diabody

<400> SEQUENCE: 13

```
Met Lys Tyr Leu Leu Pro Thr Ala Ala Ala Gly Leu Leu Leu Leu Ala
 1               5                  10                  15

Ala Gln Pro Ala Met Ala Gln Val Gln Leu Val Gln Ser Gly Ala Glu
                20                  25                  30

Val Lys Lys Pro Gly Ala Ser Val Lys Val Ser Cys Lys Ala Ser Gly
            35                  40                  45

Tyr Thr Phe Thr Asp His Ala Ile His Trp Val Arg Gln Ala Pro Gly
         50                  55                  60

Gln Arg Leu Glu Trp Met Gly Tyr Phe Ser Pro Gly Asn Asp Asp Phe
 65                  70                  75                  80
```

Lys Tyr Ser Gln Lys Phe Gln Gly Arg Val Thr Ile Thr Ala Asp Lys
                85                  90                  95

Ser Ser Ser Thr Ala Tyr Met Glu Leu Ser Ser Leu Arg Ser Glu Asp
            100                 105                 110

Thr Ala Val Tyr Tyr Cys Ala Arg Ser Trp Ile Met Gln Tyr Trp Gly
        115                 120                 125

Gln Gly Thr Leu Val Thr Val Ser Ser Gly Gly Gly Ser Asp Ile
    130                 135                 140

Val Met Thr Gln Ser Pro Asp Ser Leu Ala Val Ser Leu Gly Glu Arg
145                 150                 155                 160

Ala Thr Ile Asn Cys Lys Ser Ser Gln Ser Val Leu Tyr Ser Ser Asn
                165                 170                 175

Asn Lys Asn Tyr Leu Ala Trp Tyr Gln Gln Lys Pro Gly Gln Pro Pro
            180                 185                 190

Lys Leu Leu Ile Tyr Trp Ala Ser Thr Arg Glu Ser Gly Val Pro Asp
        195                 200                 205

Arg Phe Ser Gly Ser Gly Ser Gly Thr Asp Phe Thr Leu Thr Ile Ser
    210                 215                 220

Ser Leu Gln Ala Glu Asp Val Ala Val Tyr Tyr Cys Gln Gln Tyr Tyr
225                 230                 235                 240

Ser Tyr Pro Leu Thr Phe Gly Gly Gly Thr Lys Val Glu Ile Lys Arg
                245                 250                 255

Ala Ala Ala Leu Glu His His His His His
            260                 265

<210> SEQ ID NO 14
<211> LENGTH: 891
<212> TYPE: DNA
<213> ORGANISM: Artificial Sequence
<220> FEATURE:
<223> OTHER INFORMATION: 3E8LH(GGGGS)4.scFv

<400> SEQUENCE: 14
catatgaaat atctgttacc tactgctgct gcgggcctgc tattattagc ggcacaacca      60
gcaatggcgg cgcatcatca tcatcatcat gggtcctcgg cggtggcga aaatctgtat     120
tttcaggta gcagcggcga tattgtgatg acccagagcc cggatagttt ggccgttagc     180
ctgggcgaac gtgcgacgat taattgcaag agcagccaga gcgtgcttta cagcagcaac     240
aataagaatt acctggcgtg gtatcagcaa aaacccggcc agccgccgaa acttttgatt     300
tattgggcga gcacccgtga aagcggcgtg ccggatcgtt tctcgggctc aggcagcggg     360
accgatttta cgctgaccat cagcagcctt caggcggagg atgtcgcggt gtactactgc     420
cagcagtatt acagctatcc gttgaccttt gggggaggca ccaaagtgga gatcaaaggc     480
ggaggtggca gcggcggagg tggcagcggc ggaggtggca gcggcggagg tggctcacag     540
gtgcagctgg tacagtcggg tgcggaagtg aagaaacctg gggcgtcggt gaaagtgagc     600
tgcaaagcga gcggctatac ctttaccgat catgcgattc attgggtgcg tcaagcgcca     660
ggccagcgtc tggaatggat gggctatttt tccccaggca acgatgattt caagtattcc     720
cagaagttcc aagggcgcgt gaccattacc gccgataaaa gcgcaagcac cgcgtatatg     780
gagctgtcca gcctgcgtag cgaagataca gcggtttact attgcgcacg gagctggatt     840
atgcaatact ggggccaggg caccctggtg accgtgagca gctaaggatc c             891

<210> SEQ ID NO 15
<211> LENGTH: 293

<212> TYPE: PRT
<213> ORGANISM: Artificial Sequence
<220> FEATURE:
<223> OTHER INFORMATION: 3E8LH(GGGGS)4.scFv

<400> SEQUENCE: 15

```
Met Lys Tyr Leu Leu Pro Thr Ala Ala Ala Gly Leu Leu Leu Leu Ala
1               5                   10                  15

Ala Gln Pro Ala Met Ala Ala His His His His His His Gly Ser Ser
            20                  25                  30

Gly Gly Gly Glu Asn Leu Tyr Phe Gln Gly Ser Ser Gly Asp Ile Val
        35                  40                  45

Met Thr Gln Ser Pro Asp Ser Leu Ala Val Ser Leu Gly Glu Arg Ala
    50                  55                  60

Thr Ile Asn Cys Lys Ser Gln Ser Val Leu Tyr Ser Ser Asn Asn
65                  70                  75                  80

Lys Asn Tyr Leu Ala Trp Tyr Gln Gln Lys Pro Gly Gln Pro Pro Lys
                85                  90                  95

Leu Leu Ile Tyr Trp Ala Ser Thr Arg Glu Ser Gly Val Pro Asp Arg
            100                 105                 110

Phe Ser Gly Ser Gly Ser Gly Thr Asp Phe Thr Leu Thr Ile Ser Ser
        115                 120                 125

Leu Gln Ala Glu Asp Val Ala Val Tyr Tyr Cys Gln Gln Tyr Tyr Ser
    130                 135                 140

Tyr Pro Leu Thr Phe Gly Gly Thr Lys Val Glu Ile Lys Gly Gly
145                 150                 155                 160

Gly Gly Ser Gly Gly Gly Ser Gly Gly Gly Gly Ser Gly Gly Gly
                165                 170                 175

Gly Ser Gln Val Gln Leu Val Gln Ser Gly Ala Glu Val Lys Lys Pro
            180                 185                 190

Gly Ala Ser Val Lys Val Ser Cys Lys Ala Ser Gly Tyr Thr Phe Thr
        195                 200                 205

Asp His Ala Ile His Trp Val Arg Gln Ala Pro Gly Gln Arg Leu Glu
    210                 215                 220

Trp Met Gly Tyr Phe Ser Pro Gly Asn Asp Asp Phe Lys Tyr Ser Gln
225                 230                 235                 240

Lys Phe Gln Gly Arg Val Thr Ile Thr Ala Asp Lys Ser Ala Ser Thr
                245                 250                 255

Ala Tyr Met Glu Leu Ser Ser Leu Arg Ser Glu Asp Thr Ala Val Tyr
            260                 265                 270

Tyr Cys Ala Arg Ser Trp Ile Met Gln Tyr Trp Gly Gln Gly Thr Leu
        275                 280                 285

Val Thr Val Ser Ser
    290
```

<210> SEQ ID NO 16
<211> LENGTH: 876
<212> TYPE: DNA
<213> ORGANISM: Artificial Sequence
<220> FEATURE:
<223> OTHER INFORMATION: 3E8LH(GGGGS)3.scFv

<400> SEQUENCE: 16

```
catatgaaat atctgttacc tactgctgct gcgggcctgc tattattagc ggcacaacca      60
gcaatggcgg cgcatcatca tcatcatcat gggtcctcgg gcggtggcga aaatctgtat     120 tttcaggggta gcagcggcga tattgtgatg acccagagcc cggatagttt ggccgttagc    180
```

```
ctgggcgaac gtgcgacgat taattgcaag agcagccaga gcgtgcttta cagcagcaac      240
aataagaatt acctggcgtg gtatcagcaa aaacccggcc agccgccgaa acttttgatt      300
tattgggcga gcacccgtga aagcggcgtg ccggatcgtt tctcgggctc aggcagcggg      360
accgatttta cgctgaccat cagcagcctt caggcggagg atgtcgcggt gtactactgc      420
cagcagtatt acagctatcc gttgaccttt ggggaggca ccaaagtgga gatcaaaggc       480
ggaggtggca gcggcggagg tggcagcggc ggaggtggct cacaggtgca gctggtgcag      540
tcgggtgcgg aagtgaagaa acctggggcg tcggtgaaag tgagctgcaa agcgagcggc      600
tataccttta ccgatcatgc gattcattgg gtgcgtcaag cgccaggcca gcgtctggaa      660
tggatgggct attttcccc aggcaacgat gatttcaagt attcccagaa gttccaaggg       720
cgcgtgacca ttaccgccga taaaagcgca agcaccgcgt atatggagct gtccagcctg      780
cgtagcgaag atacagcggt ttactattgc gcacggagct ggattatgca atactggggc      840
cagggcaccc tggtgaccgt gagcagctaa ggatcc                                876
```

<210> SEQ ID NO 17
<211> LENGTH: 288
<212> TYPE: PRT
<213> ORGANISM: Artificial Sequence
<220> FEATURE:
<223> OTHER INFORMATION: 3E8LH(GGGGS)3.scFv

<400> SEQUENCE: 17

```
Met Lys Tyr Leu Leu Pro Thr Ala Ala Ala Gly Leu Leu Leu Leu Ala
1               5                   10                  15

Ala Gln Pro Ala Met Ala Ala His His His His His His Gly Ser Ser
            20                  25                  30

Gly Gly Gly Glu Asn Leu Tyr Phe Gln Gly Ser Ser Gly Asp Ile Val
        35                  40                  45

Met Thr Gln Ser Pro Asp Ser Leu Ala Val Ser Leu Gly Glu Arg Ala
    50                  55                  60

Thr Ile Asn Cys Lys Ser Ser Gln Ser Val Leu Tyr Ser Ser Asn Asn
65                  70                  75                  80

Lys Asn Tyr Leu Ala Trp Tyr Gln Gln Lys Pro Gly Gln Pro Pro Lys
                85                  90                  95

Leu Leu Ile Tyr Trp Ala Ser Thr Arg Glu Ser Gly Val Pro Asp Arg
            100                 105                 110

Phe Ser Gly Ser Gly Ser Gly Thr Asp Phe Thr Leu Thr Ile Ser Ser
        115                 120                 125

Leu Gln Ala Glu Asp Val Ala Val Tyr Tyr Cys Gln Gln Tyr Tyr Ser
    130                 135                 140

Tyr Pro Leu Thr Phe Gly Gly Gly Thr Lys Val Glu Ile Lys Gly Gly
145                 150                 155                 160

Gly Gly Ser Gly Gly Gly Gly Ser Gly Gly Gly Gly Ser Gln Val Gln
                165                 170                 175

Leu Val Gln Ser Gly Ala Glu Val Lys Lys Pro Gly Ala Ser Val Lys
            180                 185                 190

Val Ser Cys Lys Ala Ser Gly Tyr Thr Phe Thr Asp His Ala Ile His
        195                 200                 205

Trp Val Arg Gln Ala Pro Gly Gln Arg Leu Glu Trp Met Gly Tyr Phe
    210                 215                 220

Ser Pro Gly Asn Asp Asp Phe Lys Tyr Ser Gln Lys Phe Gln Gly Arg
225                 230                 235                 240
```

```
Val Thr Ile Thr Ala Asp Lys Ser Ala Ser Thr Ala Tyr Met Glu Leu
                245                 250                 255

Ser Ser Leu Arg Ser Glu Asp Thr Ala Val Tyr Tyr Cys Ala Arg Ser
            260                 265                 270

Trp Ile Met Gln Tyr Trp Gly Gln Gly Thr Leu Val Thr Val Ser Ser
        275                 280                 285

<210> SEQ ID NO 18
<211> LENGTH: 834
<212> TYPE: DNA
<213> ORGANISM: Artificial Sequence
<220> FEATURE:
<223> OTHER INFORMATION: 3E8LH(G).multimer

<400> SEQUENCE: 18
catatgaaat atctgttacc tactgctgct gcgggcctgc tattattagc ggcacaacca      60
gcaatggcgg cgcatcatca tcatcatcat gggtcctcgg cggtggcga aaatctgtat      120 tttcaggta gcagcggcga tattgtgatg acccagagcc cggatagttt ggccgttagc      180
ctgggcgaac gtgcgacgat taattgcaag agcagccaga gcgtgcttta cagcagcaac      240
aataagaatt acctggcgtg gtatcagcaa aaacccggcc agccgccgaa acttttgatt      300
tattgggcga gcacccgtga agcggcgtg ccggatcgtt tctcgggctc aggcagcggg      360
accgatttta cgctgaccat cagcagcctt caggcggagg atgtcgcggt gtactactgc      420
cagcagtatt acagctatcc gttgaccttt gggggaggca ccaaagtgga gatcaaaggt      480
caggtacagc tagtacagtc gggtgcggaa gtgaagaaac tgggggcgtc ggtgaaagtg      540
agctgcaaag cgagcggcta cctttacc gatcatgcga ttcattgggt cgtcaagcg      600 ccaggccagc gtctggaatg gatgggctat ttttccccag caacgatga tttcaagtat      660 tcccagaagt tccaagggcg cgtgaccatt accgccgata aaagcgcaag caccgcgtat      720
atggagctgt ccagcctgcg tagcgaagat acagcggttt actattgcgc acggagctgg      780
attatgcaat actggggcca gggcaccctg gtgaccgtga gcagctaagg atcc      834

<210> SEQ ID NO 19
<211> LENGTH: 274
<212> TYPE: PRT
<213> ORGANISM: Artificial Sequence
<220> FEATURE:
<223> OTHER INFORMATION: 3E8LH(G).multimer

<400> SEQUENCE: 19

Met Lys Tyr Leu Leu Pro Thr Ala Ala Ala Gly Leu Leu Leu Leu Ala
1               5                  10                  15

Ala Gln Pro Ala Met Ala His His His His His Gly Ser Ser
            20                  25                  30

Gly Gly Gly Glu Asn Leu Tyr Phe Gln Gly Ser Ser Gly Asp Ile Val
        35                  40                  45

Met Thr Gln Ser Pro Asp Ser Leu Ala Val Ser Leu Gly Glu Arg Ala
    50                  55                  60

Thr Ile Asn Cys Lys Ser Ser Gln Ser Val Leu Tyr Ser Ser Asn Asn
65                  70                  75                  80

Lys Asn Tyr Leu Ala Trp Tyr Gln Gln Lys Pro Gly Gln Pro Pro Lys
                85                  90                  95

Leu Leu Ile Tyr Trp Ala Ser Thr Arg Glu Ser Gly Val Pro Asp Arg
            100                 105                 110
```

Phe Ser Gly Ser Gly Ser Gly Thr Asp Phe Thr Leu Thr Ile Ser Ser
            115                 120                 125

Leu Gln Ala Glu Asp Val Ala Val Tyr Tyr Cys Gln Gln Tyr Tyr Ser
        130                 135                 140

Tyr Pro Leu Thr Phe Gly Gly Gly Thr Lys Val Glu Ile Lys Gly Gln
145                 150                 155                 160

Val Gln Leu Val Gln Ser Gly Ala Glu Val Lys Lys Pro Gly Ala Ser
            165                 170                 175

Val Lys Val Ser Cys Lys Ala Ser Gly Tyr Thr Phe Thr Asp His Ala
        180                 185                 190

Ile His Trp Val Arg Gln Ala Pro Gly Gln Arg Leu Glu Trp Met Gly
    195                 200                 205

Tyr Phe Ser Pro Gly Asn Asp Asp Phe Lys Tyr Ser Gln Lys Phe Gln
    210                 215                 220

Gly Arg Val Thr Ile Thr Ala Asp Lys Ser Ala Ser Thr Ala Tyr Met
225                 230                 235                 240

Glu Leu Ser Ser Leu Arg Ser Glu Asp Thr Ala Val Tyr Tyr Cys Ala
            245                 250                 255

Arg Ser Trp Ile Met Gln Tyr Trp Gly Gln Gly Thr Leu Val Thr Val
        260                 265                 270

Ser Ser

<210> SEQ ID NO 20
<211> LENGTH: 837
<212> TYPE: DNA
<213> ORGANISM: Artificial Sequence
<220> FEATURE:
<223> OTHER INFORMATION: 3E8LH(GG).multimer

<400> SEQUENCE: 20
catatgaaat atctgttacc tactgctgct gcgggcctgc tattattagc ggcacaacca      60
gcaatggcgg cgcatcatca tcatcatcat gggtcctcgg cggtggcga aaatctgtat     120 tttcaggtta gcagcggcga tattgtgatg acccagagcc cggatagttt ggccgttagc     180
ctgggcgaac gtgcgacgat taattgcaag agcagccaga gcgtgcttta cagcagcaac     240
aataagaatt acctggcgtg gtatcagcaa aaacccggcc agccgccgaa acttttgatt     300
tattgggcga gcacccgtga aagcggcgtg ccggatcgtt tctcgggctc aggcagcggg     360
accgatttta cgctgaccat cagcagcctt caggcggagg atgtcgcggt gtactactgc     420
cagcagtatt acagctatcc gttgaccttt gggggaggca ccaaagtgga gatcaaaggt     480
ggtcaggtac agctagtaca gtcgggtgcg gaagtgaaga aacctggggc gtcggtgaaa     540
gtgagctgca aagcgagcgg ctatacctt accgatcatg cgattcattg ggtgcgtcaa     600
gcgccaggcc agcgtctgga atggatgggc tatttttccc caggcaacga tgatttcaag     660
tattcccaga gttccaagg gcgcgtgacc attaccgccg ataaaagcgc aagcaccgcg     720
tatatggagc tgtccagcct gcgtagcgaa gatacagcgg tttactattg cgcacggagc     780
tggattatgc aatactgggg ccagggcacc ctggtgaccg tgagcagcta aggatcc       837

<210> SEQ ID NO 21
<211> LENGTH: 275
<212> TYPE: PRT
<213> ORGANISM: Artificial Sequence
<220> FEATURE:
<223> OTHER INFORMATION: 3E8LH(GG).multimer

<400> SEQUENCE: 21

Met Lys Tyr Leu Leu Pro Thr Ala Ala Ala Gly Leu Leu Leu Ala
1               5                   10                  15

Ala Gln Pro Ala Met Ala Ala His His His His His Gly Ser Ser
            20                  25                  30

Gly Gly Gly Glu Asn Leu Tyr Phe Gln Gly Ser Ser Gly Asp Ile Val
            35                  40                  45

Met Thr Gln Ser Pro Asp Ser Leu Ala Val Ser Leu Gly Glu Arg Ala
    50                  55                  60

Thr Ile Asn Cys Lys Ser Ser Gln Ser Val Leu Tyr Ser Ser Asn Asn
65                  70                  75                  80

Lys Asn Tyr Leu Ala Trp Tyr Gln Gln Lys Pro Gly Gln Pro Pro Lys
                85                  90                  95

Leu Leu Ile Tyr Trp Ala Ser Thr Arg Glu Ser Gly Val Pro Asp Arg
            100                 105                 110

Phe Ser Gly Ser Gly Ser Gly Thr Asp Phe Thr Leu Thr Ile Ser Ser
            115                 120                 125

Leu Gln Ala Glu Asp Val Ala Val Tyr Tyr Cys Gln Gln Tyr Tyr Ser
    130                 135                 140

Tyr Pro Leu Thr Phe Gly Gly Gly Thr Lys Val Glu Ile Lys Gly Gly
145                 150                 155                 160

Gln Val Gln Leu Val Gln Ser Gly Ala Glu Val Lys Lys Pro Gly Ala
                165                 170                 175

Ser Val Lys Val Ser Cys Lys Ala Ser Gly Tyr Thr Phe Thr Asp His
            180                 185                 190

Ala Ile His Trp Val Arg Gln Ala Pro Gly Gln Arg Leu Glu Trp Met
            195                 200                 205

Gly Tyr Phe Ser Pro Gly Asn Asp Asp Phe Lys Tyr Ser Gln Lys Phe
    210                 215                 220

Gln Gly Arg Val Thr Ile Thr Ala Asp Lys Ser Ala Ser Thr Ala Tyr
225                 230                 235                 240

Met Glu Leu Ser Ser Leu Arg Ser Glu Asp Thr Ala Val Tyr Tyr Cys
                245                 250                 255

Ala Arg Ser Trp Ile Met Gln Tyr Trp Gly Gln Gly Thr Leu Val Thr
            260                 265                 270

Val Ser Ser
    275

<210> SEQ ID NO 22
<211> LENGTH: 840
<212> TYPE: DNA
<213> ORGANISM: Artificial Sequence
<220> FEATURE:
<223> OTHER INFORMATION: 3E8LH(GGG).multimer

<400> SEQUENCE: 22
catatgaaat atctgttacc tactgctgct gcgggcctgc tattattagc ggcacaacca     60
gcaatggcgg cgcatcatca tcatcatcat gggtcctcgg gcggtggcga aaatctgtat    120
tttcagggta gcagcggcga tattgtgatg acccagagcc cggatagttt ggccgttagc    180
ctgggcgaac gtgcgacgat taattgcaag agcagccaga gcgtgcttta cagcagcaac    240
aataagaatt acctggcgtg gtatcagcaa aaacccggcc agccgccgaa acttttgatt    300
tattgggcga gcacccgtga aagcggcgtg ccggatcgtt tctcgggctc aggcagcggg    360
accgatttta cgctgaccat cagcagcctt caggcggagg atgtcgcggt gtactactgc    420

```
cagcagtatt acagctatcc gttgaccttt gggggaggca ccaaagtgga gatcaaaggt    480
ggaggtcagg tacagctagt acagtcgggt gcggaagtga agaaacctgg ggcgtcggtg    540
aaagtgagct gcaaagcgag cggctatacc tttaccgatc atgcgattca ttgggtgcgt    600
caagcgccag ccagcgtct ggaatggatg gctattttt ccccaggcaa cgatgatttc     660
aagtattccc agaagttcca agggcgcgtg accattaccg ccgataaaag cgcaagcacc    720
gcgtatatgg agctgtccag cctgcgtagc gaagatacag cggtttacta ttgcgcacgg    780
agctggatta tgcaatactg gggccagggc accctggtga ccgtgagcag ctaaggatcc    840
```

<210> SEQ ID NO 23
<211> LENGTH: 276
<212> TYPE: PRT
<213> ORGANISM: Artificial Sequence
<220> FEATURE:
<223> OTHER INFORMATION: 3E8LH(GGG).multimer

<400> SEQUENCE: 23

```
Met Lys Tyr Leu Leu Pro Thr Ala Ala Ala Gly Leu Leu Leu Leu Ala
1               5                   10                  15

Ala Gln Pro Ala Met Ala Ala His His His His His His Gly Ser Ser
            20                  25                  30

Gly Gly Gly Glu Asn Leu Tyr Phe Gln Gly Ser Ser Gly Asp Ile Val
        35                  40                  45

Met Thr Gln Ser Pro Asp Ser Leu Ala Val Ser Leu Gly Glu Arg Ala
    50                  55                  60

Thr Ile Asn Cys Lys Ser Gln Ser Val Leu Tyr Ser Ser Asn Asn
65                  70                  75                  80

Lys Asn Tyr Leu Ala Trp Tyr Gln Gln Lys Pro Gly Gln Pro Pro Lys
                85                  90                  95

Leu Leu Ile Tyr Trp Ala Ser Thr Arg Glu Ser Gly Val Pro Asp Arg
            100                 105                 110

Phe Ser Gly Ser Gly Ser Gly Thr Asp Phe Thr Leu Thr Ile Ser Ser
        115                 120                 125

Leu Gln Ala Glu Asp Val Ala Val Tyr Tyr Cys Gln Gln Tyr Tyr Ser
    130                 135                 140

Tyr Pro Leu Thr Phe Gly Gly Thr Lys Val Glu Ile Lys Gly Gly
145                 150                 155                 160

Gly Gln Val Gln Leu Val Gln Ser Gly Ala Glu Val Lys Lys Pro Gly
                165                 170                 175

Ala Ser Val Lys Val Ser Cys Lys Ala Ser Gly Tyr Thr Phe Thr Asp
            180                 185                 190

His Ala Ile His Trp Val Arg Gln Ala Pro Gly Gln Arg Leu Glu Trp
        195                 200                 205

Met Gly Tyr Phe Ser Pro Gly Asn Asp Asp Phe Lys Tyr Ser Gln Lys
    210                 215                 220

Phe Gln Gly Arg Val Thr Ile Thr Ala Asp Lys Ser Ala Ser Thr Ala
225                 230                 235                 240

Tyr Met Glu Leu Ser Ser Leu Arg Ser Glu Asp Thr Ala Val Tyr Tyr
                245                 250                 255

Cys Ala Arg Ser Trp Ile Met Gln Tyr Trp Gly Gln Gly Thr Leu Val
            260                 265                 270

Thr Val Ser Ser
        275
```

<210> SEQ ID NO 24
<211> LENGTH: 843
<212> TYPE: DNA
<213> ORGANISM: Artificial Sequence
<220> FEATURE:
<223> OTHER INFORMATION: 3E8LH(GGGG).diabody

<400> SEQUENCE: 24

```
catatgaaat atctgttacc tactgctgct gcgggcctgc tattattagc ggcacaacca      60
gcaatggcgg cgcatcatca tcatcatcat gggtcctcgg cggtggcga aaatctgtat      120
tttcaggta gcagcggcga tattgtgatg acccagagcc ggatagttt ggccgttagc      180
ctgggcgaac gtgcgacgat taattgcaag agcagccaga gcgtgcttta cagcagcaac      240
aataagaatt acctggcgtg gtatcagcaa aaacccggcc agccgccgaa acttttgatt      300
tattgggcga gcacccgtga agcggcgtg ccggatcgtt tctcgggctc aggcagcggg      360
accgatttta cgctgaccat cagcagcctt caggcggagg atgtcgcggt gtactactgc      420
cagcagtatt acagctatcc gttgacctt ggggaggca ccaaagtgga gatcaaaggt      480
ggaggaggtc aggtacagct agtacagtcg ggtgcggaag tgaagaaacc tggggcgtcg      540
gtgaaagtga gctgcaaagc gagcggctat accttaccg atcatgcgat tcattgggtg      600
cgtcaagcgc aggccagcg tctggaatgg atgggctatt ttccccagg caacgatgat      660
ttcaagtatt cccagaagtt ccaagggcgc gtgaccatta ccgccgataa agcgcaagc      720
accgcgtata tggagctgtc cagcctgcgt agcgaagata cagcggttta ctattgcgca      780
cggagctgga ttatgcaata ctggggccag ggcaccctgg tgaccgtgag cagctaagga      840
tcc                                                                    843
```

<210> SEQ ID NO 25
<211> LENGTH: 277
<212> TYPE: PRT
<213> ORGANISM: Artificial Sequence
<220> FEATURE:
<223> OTHER INFORMATION: 3E8LH(GGGG).diabody

<400> SEQUENCE: 25

```
Met Lys Tyr Leu Leu Pro Thr Ala Ala Ala Gly Leu Leu Leu Leu Ala
1               5                   10                  15

Ala Gln Pro Ala Met Ala Ala His His His His His His Gly Ser Ser
            20                  25                  30

Gly Gly Gly Glu Asn Leu Tyr Phe Gln Gly Ser Ser Gly Asp Ile Val
        35                  40                  45

Met Thr Gln Ser Pro Asp Ser Leu Ala Val Ser Leu Gly Glu Arg Ala
    50                  55                  60

Thr Ile Asn Cys Lys Ser Gln Ser Val Leu Tyr Ser Ser Asn Asn
65                  70                  75                  80

Lys Asn Tyr Leu Ala Trp Tyr Gln Gln Lys Pro Gly Gln Pro Pro Lys
                85                  90                  95

Leu Leu Ile Tyr Trp Ala Ser Thr Arg Glu Ser Gly Val Pro Asp Arg
            100                 105                 110

Phe Ser Gly Ser Gly Ser Gly Thr Asp Phe Thr Leu Thr Ile Ser Ser
        115                 120                 125

Leu Gln Ala Glu Asp Val Ala Val Tyr Tyr Cys Gln Gln Tyr Tyr Ser
    130                 135                 140

Tyr Pro Leu Thr Phe Gly Gly Gly Thr Lys Val Glu Ile Lys Gly Gly
145                 150                 155                 160
```

Gly Gly Gln Val Gln Leu Val Gln Ser Gly Ala Glu Val Lys Lys Pro
            165                 170                 175

Gly Ala Ser Val Lys Val Ser Cys Lys Ala Ser Gly Tyr Thr Phe Thr
        180                 185                 190

Asp His Ala Ile His Trp Val Arg Gln Ala Pro Gly Gln Arg Leu Glu
        195                 200                 205

Trp Met Gly Tyr Phe Ser Pro Gly Asn Asp Asp Phe Lys Tyr Ser Gln
210                 215                 220

Lys Phe Gln Gly Arg Val Thr Ile Thr Ala Asp Lys Ser Ala Ser Thr
225                 230                 235                 240

Ala Tyr Met Glu Leu Ser Ser Leu Arg Ser Glu Asp Thr Ala Val Tyr
            245                 250                 255

Tyr Cys Ala Arg Ser Trp Ile Met Gln Tyr Trp Gly Gln Gly Thr Leu
        260                 265                 270

Val Thr Val Ser Ser
        275

<210> SEQ ID NO 26
<211> LENGTH: 843
<212> TYPE: DNA
<213> ORGANISM: Artificial Sequence
<220> FEATURE:
<223> OTHER INFORMATION: 3E8LH(GSSG).diabody

<400> SEQUENCE: 26

```
catatgaaat atctgttacc tactgctgct gcgggcctgc tattattagc ggcacaacca      60
gcaatggcgg cgcatcatca tcatcatcat gggtcctcgg cggtggcga aaatctgtat     120
tttcaggtta gcagcggcga tattgtgatg acccagagcc cggatagttt ggccgttagc     180
ctgggcgaac gtgcgacgat taattgcaag agcagccaga gcgtgcttta cagcagcaac     240
aataagaatt acctggcgtg gtatcagcaa aaacccggcc agccgccgaa acttttgatt     300
tattgggcga gcacccgtga aagcggcgtg ccggatcgtt tctcgggctc aggcagcggg     360
accgatttta cgctgaccat cagcagcctt caggcggagg atgtcgcggt gtactactgc     420
cagcagtatt acagctatcc gttgaccttt ggggagggca ccaaagtgga gatcaaaggt     480
tcttctggtc aggtacagct agtacagtcg ggtgcggaag tgaagaaacc tggggcgtcg     540
gtgaaagtga gctgcaaagc gagcggctat acctttaccg atcatgcgat tcattgggtg     600
cgtcaagcgc aggccagcg tctggaatgg atgggctatt ttcccccagg caacgatgat     660
ttcaagtatt cccagaagtt ccaagggcgc gtgaccatta ccgccgataa agcgcaagc     720
accgcgtata tggagctgtc cagcctgcgt agcgaagata cagcggttta ctattgcgca     780
cggagctgga ttatgcaata ctggggccag ggcaccctgg tgaccgtgag cagctaagga     840
tcc                                                                 843
```

<210> SEQ ID NO 27
<211> LENGTH: 277
<212> TYPE: PRT
<213> ORGANISM: Artificial Sequence
<220> FEATURE:
<223> OTHER INFORMATION: 3E8LH(GSSG).diabody

<400> SEQUENCE: 27

Met Lys Tyr Leu Leu Pro Thr Ala Ala Ala Gly Leu Leu Leu Leu Ala
1               5                   10                  15

Ala Gln Pro Ala Met Ala Ala His His His His His His Gly Ser Ser
            20                  25                  30

Gly Gly Gly Glu Asn Leu Tyr Phe Gln Gly Ser Ser Gly Asp Ile Val
        35                  40                  45

Met Thr Gln Ser Pro Asp Ser Leu Ala Val Ser Leu Gly Glu Arg Ala
    50                  55                  60

Thr Ile Asn Cys Lys Ser Ser Gln Ser Val Leu Tyr Ser Ser Asn Asn
65                  70                  75                  80

Lys Asn Tyr Leu Ala Trp Tyr Gln Gln Lys Pro Gly Gln Pro Pro Lys
                85                  90                  95

Leu Leu Ile Tyr Trp Ala Ser Thr Arg Glu Ser Gly Val Pro Asp Arg
            100                 105                 110

Phe Ser Gly Ser Gly Ser Gly Thr Asp Phe Thr Leu Thr Ile Ser Ser
        115                 120                 125

Leu Gln Ala Glu Asp Val Ala Val Tyr Tyr Cys Gln Gln Tyr Tyr Ser
    130                 135                 140

Tyr Pro Leu Thr Phe Gly Gly Gly Thr Lys Val Glu Ile Lys Gly Ser
145                 150                 155                 160

Ser Gly Gln Val Gln Leu Val Gln Ser Gly Ala Glu Val Lys Lys Pro
                165                 170                 175

Gly Ala Ser Val Lys Val Ser Cys Lys Ala Ser Gly Tyr Thr Phe Thr
            180                 185                 190

Asp His Ala Ile His Trp Val Arg Gln Ala Pro Gly Gln Arg Leu Glu
        195                 200                 205

Trp Met Gly Tyr Phe Ser Pro Gly Asn Asp Asp Phe Lys Tyr Ser Gln
    210                 215                 220

Lys Phe Gln Gly Arg Val Thr Ile Thr Ala Asp Lys Ser Ala Ser Thr
225                 230                 235                 240

Ala Tyr Met Glu Leu Ser Ser Leu Arg Ser Glu Asp Thr Ala Val Tyr
                245                 250                 255

Tyr Cys Ala Arg Ser Trp Ile Met Gln Tyr Trp Gly Gln Gly Thr Leu
            260                 265                 270

Val Thr Val Ser Ser
        275

<210> SEQ ID NO 28
<211> LENGTH: 846
<212> TYPE: DNA
<213> ORGANISM: Artificial Sequence
<220> FEATURE:
<223> OTHER INFORMATION: 3E8LH(GGGGS).diabody

<400> SEQUENCE: 28
catatgaaat atctgttacc tactgctgct gcgggcctgc tattattagc ggcacaacca      60
gcaatggcgg cgcatcatca tcatcatcat gggtcctcgg cggtggcga aaatctgtat     120 tttcagggta gcagcggcga tattgtgatg acccagagcc cggatagttt ggccgttagc     180
ctgggcgaac gtgcgacgat taattgcaag agcagccaga gcgtgcttta cagcagcaac     240
aataagaatt acctggcgtg gtatcagcaa aaacccggcc agccgccgaa acttttgatt     300
tattgggcga gcacccgtga aagcggcgtg ccggatcgtt tctcgggctc aggcagcggg     360 accgattta cgctgaccat cagcagcctt caggcggagg atgtcgcggt gtactactgc     420
cagcagtatt acagctatcc gttgaccttt gggggaggca ccaaagtgga gatcaaaggt     480
ggaggaggtt ctcaggtaca gctagtacag tcgggtgcgg aagtgaagaa acctggggcg     540
tcggtgaaag tgagctgcaa agcgagcggc tataccttta ccgatcatgc gattcattgg     600

```
gtgcgtcaag cgccaggcca gcgtctggaa tggatgggct attttcccc aggcaacgat      660 gatttcaagt attcccagaa gttccaaggg cgcgtgacca ttaccgccga taaaagcgca      720
agcaccgcgt atatggagct gtccagcctg cgtagcgaag atacagcggt ttactattgc      780
gcacggagct ggattatgca atactggggc cagggcaccc tggtgaccgt gagcagctaa      840
ggatcc                                                                 846
```

<210> SEQ ID NO 29
<211> LENGTH: 278
<212> TYPE: PRT
<213> ORGANISM: Artificial Sequence
<220> FEATURE:
<223> OTHER INFORMATION: 3E8LH(GGGGS).diabody

<400> SEQUENCE: 29

```
Met Lys Tyr Leu Leu Pro Thr Ala Ala Ala Gly Leu Leu Leu Leu Ala
1               5                   10                  15

Ala Gln Pro Ala Met Ala Ala His His His His His His Gly Ser Ser
            20                  25                  30

Gly Gly Gly Glu Asn Leu Tyr Phe Gln Gly Ser Ser Gly Asp Ile Val
        35                  40                  45

Met Thr Gln Ser Pro Asp Ser Leu Ala Val Ser Leu Gly Glu Arg Ala
    50                  55                  60

Thr Ile Asn Cys Lys Ser Gln Ser Val Leu Tyr Ser Ser Asn Asn
65                  70                  75                  80

Lys Asn Tyr Leu Ala Trp Tyr Gln Gln Lys Pro Gly Gln Pro Pro Lys
                85                  90                  95

Leu Leu Ile Tyr Trp Ala Ser Thr Arg Glu Ser Gly Val Pro Asp Arg
            100                 105                 110

Phe Ser Gly Ser Gly Ser Gly Thr Asp Phe Thr Leu Thr Ile Ser Ser
        115                 120                 125

Leu Gln Ala Glu Asp Val Ala Val Tyr Tyr Cys Gln Gln Tyr Tyr Ser
    130                 135                 140

Tyr Pro Leu Thr Phe Gly Gly Gly Thr Lys Val Glu Ile Lys Gly Gly
145                 150                 155                 160

Gly Gly Ser Gln Val Gln Leu Val Gln Ser Gly Ala Glu Val Lys Lys
                165                 170                 175

Pro Gly Ala Ser Val Lys Val Ser Cys Lys Ala Ser Gly Tyr Thr Phe
            180                 185                 190

Thr Asp His Ala Ile His Trp Val Arg Gln Ala Pro Gly Gln Arg Leu
        195                 200                 205

Glu Trp Met Gly Tyr Phe Ser Pro Gly Asn Asp Asp Phe Lys Tyr Ser
    210                 215                 220

Gln Lys Phe Gln Gly Arg Val Thr Ile Thr Ala Asp Lys Ser Ala Ser
225                 230                 235                 240

Thr Ala Tyr Met Glu Leu Ser Ser Leu Arg Ser Glu Asp Thr Ala Val
                245                 250                 255

Tyr Tyr Cys Ala Arg Ser Trp Ile Met Gln Tyr Trp Gly Gln Gly Thr
            260                 265                 270

Leu Val Thr Val Ser Ser
        275
```

<210> SEQ ID NO 30
<211> LENGTH: 846
<212> TYPE: DNA
<213> ORGANISM: Artificial Sequence
<220> FEATURE:
<223> OTHER INFORMATION: 3E8LH(SGGGG).diabody

<400> SEQUENCE: 30

```
catatgaaat atctgttacc tactgctgct gcgggcctgc tattattagc ggcacaacca    60
gcaatggcgg cgcatcatca tcatcatcat gggtcctcgg gcggtggcga aaatctgtat   120
tttcaggta gcagcggcga tattgtgatg acccagagcc cggatagttt ggccgttagc   180
ctgggcgaac gtgcgacgat taattgcaag agcagccaga gcgtgcttta cagcagcaac   240
aataagaatt acctggcgtg gtatcagcaa aaacccggcc agccgccgaa acttttgatt   300
tattgggcga gcacccgtga aagcggcgtg ccggatcgtt tctcgggctc aggcagcggg   360
accgatttta cgctgaccat cagcagcctt caggcggagg atgtcgcggt gtactactgc   420
cagcagtatt acagctatcc gttgacccttt gggaggca ccaaagtgga gatcaaatca   480
ggtggaggag gtcaggtaca gctagtacag tcgggtgcgg aagtgaagaa acctggggcg   540
tcggtgaaag tgagctgcaa agcgagcggc tataccttta ccgatcatgc gattcattgg   600
gtgcgtcaag cgccaggcca gcgtctggaa tggatgggct attttttccc aggcaacgat   660
gatttcaagt attcccagaa gttccaaggg cgcgtgacca ttaccgccga taaaagcgca   720
agcaccgcgt atatggagct gtccagcctg cgtagcgaag atacagcggt ttactattgc   780
gcacggagct ggattatgca atactggggc cagggcaccc tggtgaccgt gagcagctaa   840
ggatcc                                                              846
```

<210> SEQ ID NO 31
<211> LENGTH: 278
<212> TYPE: PRT
<213> ORGANISM: Artificial Sequence
<220> FEATURE:
<223> OTHER INFORMATION: 3E8LH(SGGGG).diabody

<400> SEQUENCE: 31

```
Met Lys Tyr Leu Leu Pro Thr Ala Ala Ala Gly Leu Leu Leu Leu Ala
1               5                   10                  15

Ala Gln Pro Ala Met Ala Ala His His His His His His Gly Ser Ser
            20                  25                  30

Gly Gly Gly Glu Asn Leu Tyr Phe Gln Gly Ser Ser Gly Asp Ile Val
        35                  40                  45

Met Thr Gln Ser Pro Asp Ser Leu Ala Val Ser Leu Gly Glu Arg Ala
    50                  55                  60

Thr Ile Asn Cys Lys Ser Ser Gln Ser Val Leu Tyr Ser Ser Asn Asn
65                  70                  75                  80

Lys Asn Tyr Leu Ala Trp Tyr Gln Gln Lys Pro Gly Gln Pro Pro Lys
                85                  90                  95

Leu Leu Ile Tyr Trp Ala Ser Thr Arg Glu Ser Gly Val Pro Asp Arg
            100                 105                 110

Phe Ser Gly Ser Gly Ser Gly Thr Asp Phe Thr Leu Thr Ile Ser Ser
        115                 120                 125

Leu Gln Ala Glu Asp Val Ala Val Tyr Tyr Cys Gln Gln Tyr Tyr Ser
    130                 135                 140

Tyr Pro Leu Thr Phe Gly Gly Gly Thr Lys Val Glu Ile Lys Ser Gly
145                 150                 155                 160

Gly Gly Gly Gln Val Gln Leu Val Gln Ser Gly Ala Glu Val Lys Lys
                165                 170                 175

Pro Gly Ala Ser Val Lys Val Ser Cys Lys Ala Ser Gly Tyr Thr Phe
```

Thr Asp His Ala Ile His Trp Val Arg Gln Ala Pro Gly Gln Arg Leu
        180             185                 190

Glu Trp Met Gly Tyr Phe Ser Pro Gly Asn Asp Asp Phe Lys Tyr Ser
    195                 200                 205

Gln Lys Phe Gln Gly Arg Val Thr Ile Thr Ala Asp Lys Ser Ala Ser
210             215                 220

225         Phe Gln Gly Arg Val Thr Ile Thr Ala Asp Lys Ser Ala Ser
                230                 235                 240

Thr Ala Tyr Met Glu Leu Ser Ser Leu Arg Ser Glu Asp Thr Ala Val
                245                 250                 255

Tyr Tyr Cys Ala Arg Ser Trp Ile Met Gln Tyr Trp Gly Gln Gly Thr
                260                 265                 270

Leu Val Thr Val Ser Ser
        275

<210> SEQ ID NO 32
<211> LENGTH: 846
<212> TYPE: DNA
<213> ORGANISM: Artificial Sequence
<220> FEATURE:
<223> OTHER INFORMATION: 3E8HL(GGGGS).diabody

<400> SEQUENCE: 32
catatgaaat acttgctgcc aacggcagct gccggactac tcctattagc cgctcaacct      60
gctatggccg cacatcacca tcaccatcac ggaagcagtg gaggcggtga gaacctatac     120
ttccagggaa gttccggcca agtacaacta gtacagtcgg gggcggaagt caagaaaccg     180
ggtgcaagcg tgaaggtgag ttgtaaagca tctggtttta cattcacaga ccatgcgata     240
cattgggtca gacaagcacc ggggcaacgt ctggaatgga tggggtactt tagccctggg     300
aatgacgatt tcaagtactc tcaaaaattt caaggccggg ttacaatcac cgccgataaa     360
tcatcgtcaa cagcctatat ggagctttcg tccttgagat ctgaggatac ggctgtttac     420
tattgcgcga gatcttggat aatgcagtat tggggacaag gtaccctcgt aactgtgtca     480
tctggcggag gtggctccga cattgtgatg acacagagtc ctgactcatt agcggtttcc     540
ttgggggaac gggcaactat taactgtaag tccagtcaat cggtcctgta ctcgtcaaat     600
aacaagaatt atttagcttg gtaccagcaa aagcctgggc agccgcctaa acttttgatc     660
tactgggcga gcactagaga gtccggagta ccagaccgct ttagtgggtc aggttctgga     720
acggatttta ccctcactat ttcgagctta caggcggaag atgtagctgt ctattactgc     780
cagcagtatt atagctatcc acttacgttc ggcggtggca ccaaggttga aataaaataa     840
ggatcc     846

<210> SEQ ID NO 33
<211> LENGTH: 278
<212> TYPE: PRT
<213> ORGANISM: Artificial Sequence
<220> FEATURE:
<223> OTHER INFORMATION: 3E8HL(GGGGS).diabody

<400> SEQUENCE: 33

Met Lys Tyr Leu Leu Pro Thr Ala Ala Ala Gly Leu Leu Leu Leu Ala
1               5                   10                  15

Ala Gln Pro Ala Met Ala Ala His His His His His His Gly Ser Ser
            20                  25                  30

Gly Gly Gly Glu Asn Leu Tyr Phe Gln Gly Ser Ser Gly Gln Val Gln
        35                  40                  45

Leu Val Gln Ser Gly Ala Glu Val Lys Lys Pro Gly Ala Ser Val Lys
 50                  55                  60

Val Ser Cys Lys Ala Ser Gly Tyr Thr Phe Thr Asp His Ala Ile His
 65                  70                  75                  80

Trp Val Arg Gln Ala Pro Gly Gln Arg Leu Glu Trp Met Gly Tyr Phe
                 85                  90                  95

Ser Pro Gly Asn Asp Asp Phe Lys Tyr Ser Gln Lys Phe Gln Gly Arg
             100                 105                 110

Val Thr Ile Thr Ala Asp Lys Ser Ser Thr Ala Tyr Met Glu Leu
             115                 120                 125

Ser Ser Leu Arg Ser Glu Asp Thr Ala Val Tyr Tyr Cys Ala Arg Ser
130                 135                 140

Trp Ile Met Gln Tyr Trp Gly Gln Gly Thr Leu Val Thr Val Ser Ser
145                 150                 155                 160

Gly Gly Gly Gly Ser Asp Ile Val Met Thr Gln Ser Pro Asp Ser Leu
                165                 170                 175

Ala Val Ser Leu Gly Glu Arg Ala Thr Ile Asn Cys Lys Ser Ser Gln
            180                 185                 190

Ser Val Leu Tyr Ser Ser Asn Asn Lys Asn Tyr Leu Ala Trp Tyr Gln
            195                 200                 205

Gln Lys Pro Gly Gln Pro Pro Lys Leu Leu Ile Tyr Trp Ala Ser Thr
        210                 215                 220

Arg Glu Ser Gly Val Pro Asp Arg Phe Ser Gly Ser Gly Ser Gly Thr
225                 230                 235                 240

Asp Phe Thr Leu Thr Ile Ser Ser Leu Gln Ala Glu Asp Val Ala Val
            245                 250                 255

Tyr Tyr Cys Gln Gln Tyr Tyr Ser Tyr Pro Leu Thr Phe Gly Gly Gly
            260                 265                 270

Thr Lys Val Glu Ile Lys
        275

<210> SEQ ID NO 34
<211> LENGTH: 906
<212> TYPE: DNA
<213> ORGANISM: Artificial Sequence
<220> FEATURE:
<223> OTHER INFORMATION: 3E8HL(205C).scFv

<400> SEQUENCE: 34
catatgaaat acttgctgcc aacggcagct gccggactac tcctattagc cgctcaacct      60
gctatggccg cacatcacca tcaccatcac ggaagcagtg gaggcggtga gaacctatac     120
ttccagggaa gttccggcca agtacaacta gtacagtcgg gggcggaagt caagaaaccg     180
ggtgcaagcg tgaaggtgag ttgtaaagca tctggtttta cattcacaga ccatgcgata     240
cattgggtca gacaagcacc ggggcaacgt ctggaatgga tggggtactt tagccctggg     300
aatgacgatt tcaagtactc tcaaaaattt caaggccggg ttacaatcac cgccgataaa     360
tcatcgtcaa cagcctatat ggagcttcg tccttgagat ctgaggatac ggctgtttac     420
tattgcgcga atcttggat aatgcagtat tggggacaag gtaccctcgt aactgtgtca     480
tctctgagcg cggatgatgc taagaaagat gcggcgaaga aggacgatgc acaaaaagac     540
gacgcaaaaa aggatctgga cattgtgatg acacagagtc ctgactcatt agcggttcc     600 ttgggggaac gggcaactat taactgtaag tccagtcaat cggtcctgta ctcgtcaaat     660
aacaagaatt atttagcttg gtaccagcaa aagcctgggc agccgcctaa acttttgatc     720

```
tactgggcga gcactagaga gtccggagta ccagaccgct ttagtgggtc aggttctgga    780
acggatttta ccctcactat ttcgagctta caggcggaag atgtagctgt ctattactgc    840
cagcagtatt atagctatcc acttacgttc ggcggtggca ccaaggttga aataaaataa    900
ggatcc                                                               906
```

<210> SEQ ID NO 35
<211> LENGTH: 298
<212> TYPE: PRT
<213> ORGANISM: Artificial Sequence
<220> FEATURE:
<223> OTHER INFORMATION: 3E8HL(205C).scFv

<400> SEQUENCE: 35

```
Met Lys Tyr Leu Leu Pro Thr Ala Ala Ala Gly Leu Leu Leu Leu Ala
1               5                   10                  15

Ala Gln Pro Ala Met Ala Ala His His His His His His Gly Ser Ser
            20                  25                  30

Gly Gly Gly Glu Asn Leu Tyr Phe Gln Gly Ser Ser Gly Gln Val Gln
        35                  40                  45

Leu Val Gln Ser Gly Ala Glu Val Lys Lys Pro Gly Ala Ser Val Lys
50                  55                  60

Val Ser Cys Lys Ala Ser Gly Tyr Thr Phe Thr Asp His Ala Ile His
65                  70                  75                  80

Trp Val Arg Gln Ala Pro Gly Gln Arg Leu Glu Trp Met Gly Tyr Phe
                85                  90                  95

Ser Pro Gly Asn Asp Asp Phe Lys Tyr Ser Gln Lys Phe Gln Gly Arg
            100                 105                 110

Val Thr Ile Thr Ala Asp Lys Ser Ser Thr Ala Tyr Met Glu Leu
        115                 120                 125

Ser Ser Leu Arg Ser Glu Asp Thr Ala Val Tyr Tyr Cys Ala Arg Ser
130                 135                 140

Trp Ile Met Gln Tyr Trp Gly Gln Gly Thr Leu Val Thr Val Ser Ser
145                 150                 155                 160

Leu Ser Ala Asp Asp Ala Lys Lys Asp Ala Ala Lys Lys Asp Asp Ala
                165                 170                 175

Lys Lys Asp Asp Ala Lys Lys Asp Leu Asp Ile Val Met Thr Gln Ser
            180                 185                 190

Pro Asp Ser Leu Ala Val Ser Leu Gly Glu Arg Ala Thr Ile Asn Cys
        195                 200                 205

Lys Ser Ser Gln Ser Val Leu Tyr Ser Ser Asn Asn Lys Asn Tyr Leu
210                 215                 220

Ala Trp Tyr Gln Gln Lys Pro Gly Gln Pro Lys Leu Leu Ile Tyr
225                 230                 235                 240

Trp Ala Ser Thr Arg Glu Ser Gly Val Pro Asp Arg Phe Ser Gly Ser
                245                 250                 255

Gly Ser Gly Thr Asp Phe Thr Leu Thr Ile Ser Ser Leu Gln Ala Glu
            260                 265                 270

Asp Val Ala Val Tyr Tyr Cys Gln Gln Tyr Tyr Ser Tyr Pro Leu Thr
        275                 280                 285

Phe Gly Gly Gly Thr Lys Val Glu Ile Lys
    290                 295
```

<210> SEQ ID NO 36
<211> LENGTH: 891
<212> TYPE: DNA

<213> ORGANISM: Artificial Sequence
<220> FEATURE:
<223> OTHER INFORMATION: 3E8HL(GGGGS)4.scFv

<400> SEQUENCE: 36

```
catatgaaat acttgctgcc aacggcagct gccggactac tcctattagc cgctcaacct    60
gctatggccg cacatcacca tcaccatcac ggaagcagtg gaggcggtga gaacctatac   120
ttccagggaa gttccggcca agtacaacta gtacagtcgg gggcggaagt caagaaaccg   180
ggtgcaagcg tgaaggtgag ttgtaaagca tctggttata cattcacaga ccatgcgata   240
cattgggtca gacaagcacc ggggcaacgt ctggaatgga tggggtactt tagccctggg   300
aatgacgatt tcaagtactc tcaaaaattt caaggccggg ttacaatcac cgccgataaa   360
tcatcgtcaa cagcctatat ggagctttcg tccttgagat ctgaggatac ggctgtttac   420
tattgcgcga gatcttggat aatgcagtat tggggacaag gtaccctcgt aactgtatca   480
tctggcggag gtggcagcgg cggaggtggc agcggcggag gtggcagcgg cggaggtggc   540
agcgacattg taatgacaca gagtcctgac tcattagcgg tttccttggg ggaacgggca   600
actattaact gtaagtccag tcaatcggtc ctgtactcgt caaataacaa gaattattta   660
gcttggtacc agcaaaagcc tgggcagccg cctaaacttt tgatctactg ggcgagcact   720
agagagtccg gagtaccaga ccgctttagt gggtcaggtt ctggaacgga tttaccctc   780
actatttcga gcttacaggc ggaagatgta gctgtctatt actgccagca gtattatagc   840
tatccactta cgttcggcgg tggcaccaag gttgaaataa aataaggatc c            891
```

<210> SEQ ID NO 37
<211> LENGTH: 293
<212> TYPE: PRT
<213> ORGANISM: Artificial Sequence
<220> FEATURE:
<223> OTHER INFORMATION: 3E8HL(GGGGS)4.scFv

<400> SEQUENCE: 37

```
Met Lys Tyr Leu Leu Pro Thr Ala Ala Ala Gly Leu Leu Leu Leu Ala
1               5                   10                  15

Ala Gln Pro Ala Met Ala Ala His His His His His Gly Ser Ser
            20                  25                  30

Gly Gly Gly Glu Asn Leu Tyr Phe Gln Gly Ser Ser Gly Gln Val Gln
        35                  40                  45

Leu Val Gln Ser Gly Ala Glu Val Lys Lys Pro Gly Ala Ser Val Lys
    50                  55                  60

Val Ser Cys Lys Ala Ser Gly Tyr Thr Phe Thr Asp His Ala Ile His
65                  70                  75                  80

Trp Val Arg Gln Ala Pro Gly Gln Arg Leu Glu Trp Met Gly Tyr Phe
                85                  90                  95

Ser Pro Gly Asn Asp Asp Phe Lys Tyr Ser Gln Lys Phe Gln Gly Arg
            100                 105                 110

Val Thr Ile Thr Ala Asp Lys Ser Ser Ser Thr Ala Tyr Met Glu Leu
        115                 120                 125

Ser Ser Leu Arg Ser Glu Asp Thr Ala Val Tyr Tyr Cys Ala Arg Ser
    130                 135                 140

Trp Ile Met Gln Tyr Trp Gly Gln Gly Thr Leu Val Thr Val Ser Ser
145                 150                 155                 160

Gly Gly Gly Gly Ser Gly Gly Gly Ser Gly Gly Gly Gly Ser Gly
                165                 170                 175
```

```
Gly Gly Gly Ser Asp Ile Val Met Thr Gln Ser Pro Asp Ser Leu Ala
            180                 185                 190

Val Ser Leu Gly Glu Arg Ala Thr Ile Asn Cys Lys Ser Gln Ser
        195                 200                 205

Val Leu Tyr Ser Ser Asn Asn Lys Asn Tyr Leu Ala Trp Tyr Gln Gln
        210                 215                 220

Lys Pro Gly Gln Pro Pro Lys Leu Leu Ile Tyr Trp Ala Ser Thr Arg
225                 230                 235                 240

Glu Ser Gly Val Pro Asp Arg Phe Ser Gly Ser Gly Ser Gly Thr Asp
                245                 250                 255

Phe Thr Leu Thr Ile Ser Ser Leu Gln Ala Glu Asp Val Ala Val Tyr
            260                 265                 270

Tyr Cys Gln Gln Tyr Tyr Ser Tyr Pro Leu Thr Phe Gly Gly Gly Thr
        275                 280                 285

Lys Val Glu Ile Lys
    290
```

<210> SEQ ID NO 38
<211> LENGTH: 875
<212> TYPE: DNA
<213> ORGANISM: Artificial Sequence
<220> FEATURE:
<223> OTHER INFORMATION: 3E8HL(GGGGS)4.scFv

<400> SEQUENCE: 38

```
catatgaaat acttgctgcc aacggcagct gccggactac tcctattagc cgctcaacct      60
gctatggccg cacatcacca tcaccatcac ggaagcagtg gaggcggtga gaacctatac     120
ttccagggaa gttccggcca agtacaacta gtacagtcgg gggcggaagt caagaaaccg     180
ggtgcaagcg tgaaggtgag ttgtaaagca tctggtttata cattcacaga ccatgcgata     240
cattgggtca gacaagcacc ggggcaacgt ctggaatgga tggggtactt tagccctggg     300
aatgacgatt tcaagtactc tcaaaaattt caaggccggg ttacaatcac cgccgataaa     360
tcatcgtcaa cagcctatat ggagctttcg tccttgagat ctgaggatac ggctgtttac     420
tattgcgcga tcttggat aatgcagtat tggggacaag gtaccctcgt aactgtatca     480
tctggcggag gtggcagcgg cggaggtggc agcggcggag gtggcagcga cattgtaatg     540
acacagagtc ctgactcatt agcggtttcc ttggggaac gggcaactat taactgtaag     600
tccagtcaat cggtcctgta ctcgtcaaat aacaagaatt atttagcttg gtaccagcaa     660
aagcctgggc agccgcctaa acttttgatc tactgggcga gcactagaga gtccggagta     720
ccagaccgct ttagtgggtc aggttctgga acggattta ccctcactat ttcgagctta     780
caggcggaag atgtagctgt ctattactgc cagcagtatt atagctatcc acttacgttg     840
gcggtggcac aaggttgaa ataaataag gatcc                                 875
```

<210> SEQ ID NO 39
<211> LENGTH: 288
<212> TYPE: PRT
<213> ORGANISM: Artificial Sequence
<220> FEATURE:
<223> OTHER INFORMATION: 3E8HL(GGGGS)3.scFv

<400> SEQUENCE: 39

```
Met Lys Tyr Leu Leu Pro Thr Ala Ala Ala Gly Leu Leu Leu Leu Ala
1               5                   10                  15

Ala Gln Pro Ala Met Ala Ala His His His His His His Gly Ser Ser
            20                  25                  30
```

Gly Gly Gly Glu Asn Leu Tyr Phe Gln Gly Ser Ser Gly Gln Val Gln
            35                  40                  45

Leu Val Gln Ser Gly Ala Glu Val Lys Lys Pro Gly Ala Ser Val Lys
    50                  55                  60

Val Ser Cys Lys Ala Ser Gly Tyr Thr Phe Thr Asp His Ala Ile His
65                  70                  75                  80

Trp Val Arg Gln Ala Pro Gly Gln Arg Leu Glu Trp Met Gly Tyr Phe
                85                  90                  95

Ser Pro Gly Asn Asp Asp Phe Lys Tyr Ser Gln Lys Phe Gln Gly Arg
            100                 105                 110

Val Thr Ile Thr Ala Asp Lys Ser Ser Thr Ala Tyr Met Glu Leu
            115                 120                 125

Ser Ser Leu Arg Ser Glu Asp Thr Ala Val Tyr Tyr Cys Ala Arg Ser
            130                 135                 140

Trp Ile Met Gln Tyr Trp Gly Gln Gly Thr Leu Val Thr Val Ser Ser
145                 150                 155                 160

Gly Gly Gly Gly Ser Gly Gly Gly Ser Gly Gly Gly Gly Ser Asp
            165                 170                 175

Ile Val Met Thr Gln Ser Pro Asp Ser Leu Ala Val Ser Leu Gly Glu
            180                 185                 190

Arg Ala Thr Ile Asn Cys Lys Ser Ser Gln Ser Val Leu Tyr Ser Ser
            195                 200                 205

Asn Asn Lys Asn Tyr Leu Ala Trp Tyr Gln Gln Lys Pro Gly Gln Pro
            210                 215                 220

Pro Lys Leu Leu Ile Tyr Trp Ala Ser Thr Arg Glu Ser Gly Val Pro
225                 230                 235                 240

Asp Arg Phe Ser Gly Ser Gly Ser Gly Thr Asp Phe Thr Leu Thr Ile
            245                 250                 255

Ser Ser Leu Gln Ala Glu Asp Val Ala Val Tyr Tyr Cys Gln Gln Tyr
            260                 265                 270

Tyr Ser Tyr Pro Leu Thr Phe Gly Gly Gly Thr Lys Val Glu Ile Lys
            275                 280                 285

<210> SEQ ID NO 40
<211> LENGTH: 842
<212> TYPE: DNA
<213> ORGANISM: Artificial Sequence
<220> FEATURE:
<223> OTHER INFORMATION: 3E8HL(GGGG).diabody

<400> SEQUENCE: 40
catatgaaat acttgctgcc aacggcagct gccggactac tcctattagc cgctcaacct      60
gctatggccg cacatcacca tcaccatcac ggaagcagtg gaggcggtga gaacctatac     120
ttccagggaa gttccggcca agtacaacta gtacagtcgg gggcggaagt caagaaaccg     180
ggtgcaagcg tgaaggtgag ttgtaaagca tctggttata cattcacaga ccatgcgata     240
cattgggtca gacaagcacc ggggcaacgt ctggaatgga tggggtactt tagccctggg     300
aatgacgatt tcaagtactc tcaaaaattt caaggccggg ttacaatcac cgccgataaa     360
tcatcgtcaa cagcctatat ggagctttcg tccttgagat ctgaggatac ggctgtttac     420
tattgcgcga gatcttggat aatgcagtat ggggacaagg taccctcgt aactgtatca     480
tctggcggag gtggcgacat tgtaatgaca cagagtcctg actcattagc ggtttccttg     540
ggggaacggg caactattaa ctgtaagtcc agtcaatcgg tcctgtactc gtcaaataac     600

```
aagaattatt tagcttggta ccagcaaaag cctgggcagc cgcctaaact tttgatctac    660
tgggcgagca ctagagagtc cggagtacca gaccgcttta gtgggtcagg ttctggaacg    720
gattttacct cactatttcg agcttacagg cggaagatgt agctgtctat tactgccagc    780
agtattatag ctatccactt acgttcggcg gtgggcaccaa ggttgaaata aaataaggat    840
cc    842
```

<210> SEQ ID NO 41
<211> LENGTH: 277
<212> TYPE: PRT
<213> ORGANISM: Artificial Sequence
<220> FEATURE:
<223> OTHER INFORMATION: 3E8HL(GGGG).diabody

<400> SEQUENCE: 41

```
Met Lys Tyr Leu Leu Pro Thr Ala Ala Ala Gly Leu Leu Leu Leu Ala
1               5                   10                  15

Ala Gln Pro Ala Met Ala Ala His His His His His His Gly Ser Ser
            20                  25                  30

Gly Gly Gly Glu Asn Leu Tyr Phe Gln Gly Ser Ser Gly Gln Val Gln
        35                  40                  45

Leu Val Gln Ser Gly Ala Glu Val Lys Lys Pro Gly Ala Ser Val Lys
    50                  55                  60

Val Ser Cys Lys Ala Ser Gly Tyr Thr Phe Thr Asp His Ala Ile His
65                  70                  75                  80

Trp Val Arg Gln Ala Pro Gly Gln Arg Leu Glu Trp Met Gly Tyr Phe
                85                  90                  95

Ser Pro Gly Asn Asp Asp Phe Lys Tyr Ser Gln Lys Phe Gln Gly Arg
            100                 105                 110

Val Thr Ile Thr Ala Asp Lys Ser Ser Thr Ala Tyr Met Glu Leu
        115                 120                 125

Ser Ser Leu Arg Ser Glu Asp Thr Ala Val Tyr Tyr Cys Ala Arg Ser
    130                 135                 140

Trp Ile Met Gln Tyr Trp Gly Gln Gly Thr Leu Val Thr Val Ser Ser
145                 150                 155                 160

Gly Gly Gly Gly Asp Ile Val Met Thr Gln Ser Pro Asp Ser Leu Ala
                165                 170                 175

Val Ser Leu Gly Glu Arg Ala Thr Ile Asn Cys Lys Ser Ser Gln Ser
            180                 185                 190

Val Leu Tyr Ser Ser Asn Asn Lys Asn Tyr Leu Ala Trp Tyr Gln Gln
        195                 200                 205

Lys Pro Gly Gln Pro Pro Lys Leu Leu Ile Tyr Trp Ala Ser Thr Arg
    210                 215                 220

Glu Ser Gly Val Pro Asp Arg Phe Ser Gly Ser Gly Ser Gly Thr Asp
225                 230                 235                 240

Phe Thr Leu Thr Ile Ser Ser Leu Gln Ala Glu Asp Val Ala Val Tyr
                245                 250                 255

Tyr Cys Gln Gln Tyr Tyr Ser Tyr Pro Leu Thr Phe Gly Gly Gly Thr
            260                 265                 270

Lys Val Glu Ile Lys
        275
```

<210> SEQ ID NO 42
<211> LENGTH: 843
<212> TYPE: DNA
<213> ORGANISM: Artificial Sequence
<220> FEATURE:
<223> OTHER INFORMATION: 3E8HL(GSSG).diabody

<400> SEQUENCE: 42

```
catatgaaat acttgctgcc aacggcagct gccggactac tcctattagc cgctcaacct    60
gctatggccg cacatcacca tcaccatcac ggaagcagtg gaggcggtga gaacctatac   120
ttccagggaa gttccggcca agtacaacta gtacagtcgg gggcggaagt caagaaaccg   180
ggtgcaagcg tgaaggtgag ttgtaaagca tctggtttata cattcacaga ccatgcgata   240
cattgggtca gacaagcacc ggggcaacgt ctggaatgga tggggtactt tagccctggg   300
aatgacgatt tcaagtactc tcaaaaattt caaggccggg ttacaatcac cgccgataaa   360
tcatcgtcaa cagcctatat ggagctttcg tccttgagat ctgaggatac ggctgtttac   420
tattgcgcga tcttggat aatgcagtat ggggacaag gtaccctcgt aactgtatca   480
tctggcagct ccggagacat tgtaatgaca cagagtcctg actcattagc ggtttccttg   540
ggggaacggg caactattaa ctgtaagtcc agtcaatcgg tcctgtactc gtcaaataac   600
aagaattatt tagcttggta ccagcaaaag cctgggcagc cgcctaaact tttgatctac   660
tgggcgagca ctagagagtc cggagtacca gaccgcttta gtgggtcagg ttctggaacg   720
gattttaccc tcactatttc gagcttacag gcggaagatg tagctgtcta ttactgccag   780
cagtattata gctatccact tacgttcggc ggtggcacca aggttgaaat aaaataagga   840
tcc                                                                  843
```

<210> SEQ ID NO 43
<211> LENGTH: 277
<212> TYPE: PRT
<213> ORGANISM: Artificial Sequence
<220> FEATURE:
<223> OTHER INFORMATION: 3E8HL(GSSG).diabody

<400> SEQUENCE: 43

```
Met Lys Tyr Leu Leu Pro Thr Ala Ala Ala Gly Leu Leu Leu Leu Ala
1               5                   10                  15

Ala Gln Pro Ala Met Ala Ala His His His His His His Gly Ser Ser
            20                  25                  30

Gly Gly Gly Glu Asn Leu Tyr Phe Gln Gly Ser Ser Gly Gln Val Gln
        35                  40                  45

Leu Val Gln Ser Gly Ala Glu Val Lys Lys Pro Gly Ala Ser Val Lys
    50                  55                  60

Val Ser Cys Lys Ala Ser Gly Tyr Thr Phe Thr Asp His Ala Ile His
65                  70                  75                  80

Trp Val Arg Gln Ala Pro Gly Gln Arg Leu Glu Trp Met Gly Tyr Phe
                85                  90                  95

Ser Pro Gly Asn Asp Asp Phe Lys Tyr Ser Gln Lys Phe Gln Gly Arg
            100                 105                 110

Val Thr Ile Thr Ala Asp Lys Ser Ser Thr Ala Tyr Met Glu Leu
        115                 120                 125

Ser Ser Leu Arg Ser Glu Asp Thr Ala Val Tyr Tyr Cys Ala Arg Ser
    130                 135                 140

Trp Ile Met Gln Tyr Trp Gly Gln Gly Thr Leu Val Thr Val Ser Ser
145                 150                 155                 160

Gly Ser Ser Gly Asp Ile Val Met Thr Gln Ser Pro Asp Ser Leu Ala
                165                 170                 175

Val Ser Leu Gly Glu Arg Ala Thr Ile Asn Cys Lys Ser Ser Gln Ser
```

```
              180             185             190
Val Leu Tyr Ser Ser Asn Asn Lys Asn Tyr Leu Ala Trp Tyr Gln Gln
            195                 200                 205

Lys Pro Gly Gln Pro Pro Lys Leu Leu Ile Tyr Trp Ala Ser Thr Arg
        210                 215                 220

Glu Ser Gly Val Pro Asp Arg Phe Ser Gly Ser Gly Ser Gly Thr Asp
225                 230                 235                 240

Phe Thr Leu Thr Ile Ser Ser Leu Gln Ala Glu Asp Val Ala Val Tyr
                245                 250                 255

Tyr Cys Gln Gln Tyr Tyr Ser Tyr Pro Leu Thr Phe Gly Gly Gly Thr
            260                 265                 270

Lys Val Glu Ile Lys
        275

<210> SEQ ID NO 44
<211> LENGTH: 845
<212> TYPE: DNA
<213> ORGANISM: Artificial Sequence
<220> FEATURE:
<223> OTHER INFORMATION: 3E8HL(SGGGG).diabody

<400> SEQUENCE: 44
catatgaaat acttgctgcc aacggcagct gccggactac tcctattagc cgctcaacct    60
gctatggccg cacatcacca tcaccatcac ggaagcagtg gaggcggtga gaacctatac   120
ttccagggaa gttccggcca agtacaacta gtacagtcgg gggcggaagt caagaaaccg   180
ggtgcaagcg tgaaggtgag ttgtaaagca tctggtttat cattcacaga ccatgcgata   240
cattgggtca gacaagcacc ggggcaacgt ctggaatgga tggggtactt tagccctggg   300
aatgacgatt tcaagtactc tcaaaaattt caaggccggg ttacaatcac cgccgataaa   360
tcatcgtcaa cagcctatat ggagctttcg tccttgagat ctgaggatac ggctgtttac   420
tattgcgcga gatcttggat aatgcagtat tggggacaag gtaccctcgt aactgtatca   480
tcttccggcg gaggtggcga cattgtaatg acacagagtc ctgactcatt agcggtttcc   540
ttgggggaac gggcaactat taactgtaag tccagtcaat cggtcctgta ctcgtcaaat   600
aacaagaatt atttagcttg gtaccagcaa aagcctgggc agccgcctaa acttttgatc   660
tactgggcga gcactagaga gtccggagta ccagaccgct ttagtgggtc aggttctgga   720
acggatttta ccctcactat ttcgagctta caggcggaag atgtagctgt ctattactgc   780
cagcagtatt atagctatcc acttacgttc ggcggtggca ccaaggttga aataaaataa   840
gatcc                                                              845

<210> SEQ ID NO 45
<211> LENGTH: 278
<212> TYPE: PRT
<213> ORGANISM: Artificial Sequence
<220> FEATURE:
<223> OTHER INFORMATION: 3E8HL(SGGGG).diabody

<400> SEQUENCE: 45

Met Lys Tyr Leu Leu Pro Thr Ala Ala Ala Gly Leu Leu Leu Leu Ala
1               5                   10                  15

Ala Gln Pro Ala Met Ala Ala His His His His His His Gly Ser Ser
            20                  25                  30

Gly Gly Gly Glu Asn Leu Tyr Phe Gln Gly Ser Ser Gly Gln Val Gln
        35                  40                  45
```

Leu Val Gln Ser Gly Ala Glu Val Lys Lys Pro Gly Ala Ser Val Lys
 50                  55                  60

Val Ser Cys Lys Ala Ser Gly Tyr Thr Phe Thr Asp His Ala Ile His
 65                  70                  75                  80

Trp Val Arg Gln Ala Pro Gly Gln Arg Leu Glu Trp Met Gly Tyr Phe
                 85                  90                  95

Ser Pro Gly Asn Asp Asp Phe Lys Tyr Ser Gln Lys Phe Gln Gly Arg
                100                 105                 110

Val Thr Ile Thr Ala Asp Lys Ser Ser Thr Ala Tyr Met Glu Leu
                115                 120                 125

Ser Ser Leu Arg Ser Glu Asp Thr Ala Val Tyr Tyr Cys Ala Arg Ser
130                 135                 140

Trp Ile Met Gln Tyr Trp Gly Gln Gly Thr Leu Val Thr Val Ser Ser
145                 150                 155                 160

Ser Gly Gly Gly Gly Asp Ile Val Met Thr Gln Ser Pro Asp Ser Leu
                165                 170                 175

Ala Val Ser Leu Gly Glu Arg Ala Thr Ile Asn Cys Lys Ser Ser Gln
                180                 185                 190

Ser Val Leu Tyr Ser Ser Asn Asn Lys Asn Tyr Leu Ala Trp Tyr Gln
                195                 200                 205

Gln Lys Pro Gly Gln Pro Pro Lys Leu Leu Ile Tyr Trp Ala Ser Thr
210                 215                 220

Arg Glu Ser Gly Val Pro Asp Arg Phe Ser Gly Ser Gly Ser Gly Thr
225                 230                 235                 240

Asp Phe Thr Leu Thr Ile Ser Ser Leu Gln Ala Glu Asp Val Ala Val
                245                 250                 255

Tyr Tyr Cys Gln Gln Tyr Tyr Ser Tyr Pro Leu Thr Phe Gly Gly Gly
                260                 265                 270

Thr Lys Val Glu Ile Lys
            275

<210> SEQ ID NO 46
<211> LENGTH: 255
<212> TYPE: PRT
<213> ORGANISM: Artificial Sequence
<220> FEATURE:
<223> OTHER INFORMATION: 3E8HL(SGGGG).diabody

<400> SEQUENCE: 46

Met Lys Tyr Leu Leu Pro Thr Ala Ala Ala Gly Leu Leu Leu Leu Ala
 1               5                  10                  15

Ala Gln Pro Ala Met Ala Gln Val Gln Leu Val Gln Ser Gly Ala Glu
                 20                  25                  30

Val Lys Lys Pro Gly Ala Ser Val Lys Val Ser Cys Lys Ala Ser Gly
             35                  40                  45

Tyr Thr Phe Thr Asp His Ala Ile His Trp Val Arg Gln Ala Pro Gly
 50                  55                  60

Gln Arg Leu Glu Trp Met Gly Tyr Phe Ser Pro Gly Asn Asp Asp Phe
 65                  70                  75                  80

Lys Tyr Ser Gln Lys Phe Gln Gly Arg Val Thr Ile Thr Ala Asp Lys
                 85                  90                  95

Ser Ser Ser Thr Ala Tyr Met Glu Leu Ser Ser Leu Arg Ser Glu Asp
                100                 105                 110

Thr Ala Val Tyr Tyr Cys Ala Arg Ser Trp Ile Met Gln Tyr Trp Gly
                115                 120                 125

```
Gln Gly Thr Leu Val Thr Val Ser Ser Gly Gly Gly Gly Ser Asp Ile
    130                 135                 140
Val Met Thr Gln Ser Pro Asp Ser Leu Ala Val Ser Leu Gly Glu Arg
145                 150                 155                 160
Ala Thr Ile Asn Cys Lys Ser Ser Gln Ser Val Leu Tyr Ser Ser Asn
                165                 170                 175
Asn Lys Asn Tyr Leu Ala Trp Tyr Gln Gln Lys Pro Gly Gln Pro Pro
            180                 185                 190
Lys Leu Leu Ile Tyr Trp Ala Ser Thr Arg Glu Ser Gly Val Pro Asp
        195                 200                 205
Arg Phe Ser Gly Ser Gly Ser Gly Thr Asp Phe Thr Leu Thr Ile Ser
    210                 215                 220
Ser Leu Gln Ala Glu Asp Val Ala Val Tyr Tyr Cys Gln Gln Tyr Tyr
225                 230                 235                 240
Ser Tyr Pro Leu Thr Phe Gly Gly Gly Thr Lys Val Glu Ile Lys
                245                 250                 255
```

```
<210> SEQ ID NO 47
<211> LENGTH: 768
<212> TYPE: DNA
<213> ORGANISM: Artificial Sequence
<220> FEATURE:
<223> OTHER INFORMATION: Artificial Construct

<400> SEQUENCE: 47
atgaaatact tgttaccaac ggcagctgct ggactactcc tattggcggc tcaacctgct      60
atggctcaag tacaactagt acagtcgggg gcggaagtca agaaaccggg tgcaagcgtg     120
aaggtgagtt gtaaagcatc tggttataca ttcacagacc atgcgataca ttgggtcaga     180
caagcaccgg gcaacgtct  ggaatggatg gggtacttta gccctgggaa tgacgatttc     240
aagtactctc aaaaatttca aggccgggtt acaatcaccg ccgataaatc atcgtcaaca     300
gcctatatgg agctttcgtc cttgagatct gaggatacgg ctgtttacta ttgcgcgaga     360
tcttggataa tgcagtattg gggacaaggt accctcgtaa ctgtgtcatc tggcggaggt     420
ggctccgaca ttgtgatgac acagagtcct gactcattag cggtttcctt gggggaacgg     480
gcaactatta actgtaagtc cagtcaatcg gtcctgtact cgtcaaataa caagaattat     540
ttagcttggt accagcaaaa gcctgggcag ccgcctaaac ttttgatcta ctgggcgagc     600
actagagagt ccggagtacc agaccgcttt agtgggtcag gttctggaac ggattttacc     660
ctcactattt cgagcttaca ggcggaagat gtagctgtct attactgcca gcagtattat     720
agctatccac ttacgttcgg cggtggcacc aaggttgaaa taaaataa                  768
```

```
<210> SEQ ID NO 48
<211> LENGTH: 7321
<212> TYPE: DNA
<213> ORGANISM: Artificial Sequence
<220> FEATURE:
<223> OTHER INFORMATION: Complete Plasmid

<400> SEQUENCE: 48
tacgactcac tatagggaa ttgtgagcgg ataacaattc ccctctagaa ataattttgt       60
ttaactttaa gaaggagata tacatatgaa atacttgtta ccaacggcag ctgctggact     120
actcctattg gcggctcaac ctgctatggc tcaagtacaa ctagtacagt cgggggcgga     180
agtcaagaaa ccgggtgcaa gcgtgaaggt gagttgtaaa gcatctggtt atacattcac     240
agaccatgcg atacattggg tcagacaagc accggggcaa cgtctggaat ggatgggta     300
```

```
ctttagccct gggaatgacg atttcaagta ctctcaaaaa tttcaaggcc gggttacaat    360
caccgccgat aaatcatcgt caacagccta tatggagctt tcgtccttga gatctgagga    420
tacggctgtt tactattgcg cgagatcttg gataatgcag tattggggac aaggtaccct    480
cgtaactgtg tcatctggcg gaggtggctc cgacattgtg atgacacaga gtcctgactc    540
attagcggtt tccttggggg aacgggcaac tattaactgt aagtccagtc aatcggtcct    600
gtactcgtca ataacaaga attatttagc ttggtaccag caaaagcctg gcagccgcc     660 taaactttg atctactggg cgagcactag agagtccgga gtaccagacc gctttagtgg     720
gtcaggttct ggaacggatt ttaccctcac tatttcgagc ttacaggcgg aagatgtagc    780
tgtctattac tgccagcagt attatagcta tccacttacg ttcggcggtg gcaccaaggt    840
tgaaataaaa taaggatccg gctgctaaca agcccgaaa ggaagctgag ttggctgctg     900
ccaccgctga gcaataacta gcataacccc ttggggcctc taaacgggtc ttgaggggtt    960
ttttgctgaa aggaggaact atatccggat atcccgcaag aggcccggca gtaccggcat   1020
aaccaagcct atgcctacag catccagggt gacggtgccg aggatgacga tgagcgcatt   1080
gttagatttc atacacggtg cctgactgcg ttagcaattt aactgtgata aactaccgca   1140
ttaaagctta tcgatgataa gctgtcaaac atgagaattc gaggtctgcc ttgtgaagaa   1200
ggtgttgctg actcatacca ggcctgaatc gccccatcat ccagccagaa agtgagggag   1260
ccacggttga tgagagcttt gttgtaggtg gaccagttgg tgattttgaa cttttgcttt   1320
gccacggaac ggtctgcgtt gtcgggaaga tgcgtgatct gatccttcaa ctcagcaaaa   1380
gttcgattta ttcaacaaag ccacgttgtg tctcaaaatc tctgatgtta cattgcacaa   1440
gataaaaata tatcatcatg aacaataaaa ctgtctgctt acataaacag taatacaagg   1500
ggtgttatga gccatattca acgggaaacg tcttgctcga ggccgcgatt aaattccaac   1560
atggatgctg atttatatgg gtataaatgg ctcgcgata atgtcgggca atcaggtgcg   1620
acaatctatc gattgtatgg gaagcccgat gcgccagagt tgtttctgaa acatggcaaa   1680
ggtagcgttg ccaatgatgt tacagatgag atggtcagac taaactggct gacggaattt   1740
atgcctcttc cgaccatcaa gcattttatc cgtactcctg atgatgcatg gttactcacc   1800
actgcgatcc ccgggaaaac agcattccag gtattagaag aatatcctga ttcaggtgaa   1860
aatattgctg atgcgctggc agtgttcctg cgccggttgc attcgattcc tgtttgtaat   1920 tgtccttttta acagcgatcg cgtatttcgt ctcgctcagg cgcaatcacg aatgaataac   1980
ggtttggttt atgcgagtga ttttgatgac gagcgtaatg gctggcctgt tgaacaagtc   2040
tggaaagaaa tgcataagct tttgccattc tcaccggatt cagtcgtcac tcatggtgat   2100
ttctcacttg ataaccttat ttttgacgag gggaaattaa taggttgtat tgatgttgga   2160
cgagtcggaa tcgcagaccg ataccaggat cttgccatcc tatggaactg cctcggtgag   2220
ttttctcctt cattacagaa acggctttt caaaaatatg gtattgataa tcctgatatg   2280
aataaattgc agtttcattt gatgctcgat gagttttct aatcagaatt ggttaattgg   2340
ttgtaacact ggcagagcat tacgctgact tgacgggacg gcggctttgt tgaataaatc   2400
gaacttttgc tgagttgaag gatcagatca cgcatcttcc cgacaacgca gaccgttccg   2460
tggcaaagca aaagttcaaa atcaccaact ggtccaccta caacaaagct ctcatcaacc   2520
gtggctccct cactttctgg ctggatgatg ggcgattca ggcctggtat gagtcagcaa   2580
caccttcttc acgaagcaga cctcagtact caccagtcac agaaaagcat cttacggatg   2640
```

```
gcatgacagt aagagaatta tgcagtgctg ccataaccat gagtgataac actgcggcca    2700
acttacttct gacaacgatc ggaggaccga aggagctaac cgcttttttg cacaacatgg    2760
gggatcatgt aactcgcctt gatcgttggg aaccggagct gaatgaagcc ataccaaacg    2820
acgagcgtga caccacgatg cctgcagcaa tggcaacaac gttgcgcaaa ctattaactg    2880
gcgaactact tactctagct tcccggcaac aattaataga ctggatggag gcggataaag    2940
ttgcaggacc acttctgcgc tcggcccttc cggctggctg gtttattgct gataaatctg    3000
gagccggtga gcgtggttct cgtggtatca ttgcagcact ggggccagat ggtaagccct    3060
cccgtatcgt agttatctac acgacgggga gtcaggcaac tatggatgaa cgaaatagac    3120
agatcgctga gataggtgcc tcactgatta agcattggta actgtcagac caagtttact    3180
catatatact ttagattgat ttaaaacttc attttttaatt taaaaggatc taggtgaaga    3240
tcctttttga taatctcatg accaaaatcc cttaacgtga gttttcgttc cactgagcgt    3300
cagaccccgt agaaaagatc aaaggatctt cttgagatcc ttttttttctg cgcgtaatct    3360
gctgcttgca acaaaaaaa ccaccgctac cagcggtggt ttgtttgccg gatcaagagc    3420
taccaactct ttttccgaag gtaactggct tcagcagagc gcagatacca aatactgtcc    3480
ttctagtgta gccgtagtta ggccaccact tcaagaactc tgtagcaccg cctacatacc    3540
tcgctctgct aatcctgtta ccagtggctg ctgccagtgg cgataagtcg tgtcttaccg    3600
ggttggactc aagacgatag ttaccggata aggcgcagcg gtcgggctga acggggggtt    3660
cgtgcacaca gcccagcttg gagcgaacga cctacaccga actgagatac ctacagcgtg    3720
agctatgaga agcgccacg cttcccgaag ggagaaaggc ggacaggtat ccggtaagcg    3780
gcagggtcgg aacaggagag cgcacgaggg agcttccagg gggaaacgcc tggtatcttt    3840
atagtcctgt cgggtttcgc cacctctgac ttgagcgtcg atttttgtga tgctcgtcag    3900
gggggcggag cctatggaaa aacgccagca acgcggcctt tttacggttc ctggcctttt    3960
gctgcccttt tgctcacatg ttctttcctg cgttatcccc tgattctgtg ataaccgta    4020
ttaccgcctt tgagtgagct gataccgctc gccgcagccg aacgaccgag cgcagcgagt    4080
cagtgagcga ggaagcggaa gagcgcctga tgcggtattt tctccttacg catctgtgcg    4140
gtatttcaca ccgcaatggt gcactctcag tacaatctgc tctgatgccg catagttaag    4200
ccagtataca ctccgctatc gctacgtgac tgggtcatgg ctgcgccccg acacccgcca    4260
acacccgctg acgcgccctg acgggcttgt ctgctcccgg catccgctta cagacaagct    4320
gtgaccgtct ccgggagctg catgtgtcag aggttttcac cgtcatcacc gaaacgcgcg    4380
aggcagctgc ggtaaagctc atcagcgtgg tcgtgaagcg attcacagat gtctgcctgt    4440
tcatccgcgt ccagctcgtt gagtttctcc agaagcgtta atgtctggct tctgataaag    4500
cgggccatgt taagggcggt ttttttcctgt ttggtcactg atgcctccgt gtaaggggga    4560
tttctgttca tggggtaat gataccgatg aaacgagaga ggatgctcac gatacgggtt    4620
actgatgatg aacatgcccg gttactggaa cgttgtgagg gtaaacaact ggcggtatgg    4680
atgcggcggg accagagaaa aatcactcag ggtcaatgcc agcgcttcgt taatacagat    4740
gtaggtgttc cacagggtag ccagcagcat cctgcgatgc agatccggaa cataatggtg    4800
cagggcgctg acttccgcgt ttccagactt tacgaaacac ggaaaccgaa gaccattcat    4860
gttgttgctc aggtcgcaga cgttttgcag cagcagtcgc ttcacgttcg ctcgcgtatc    4920
ggtgattcat tctgctaacc agtaaggcaa ccccgccagc ctagccgggt cctcaacgac    4980
aggagcacga tcatgcgcac ccgtggccag gacccaacgc tgcccgagat gcgccgcgtg    5040
```

```
cggctgctgg agatggcgga cgcgatggat atgttctgcc aagggttggt ttgcgcattc    5100
acagttctcc gcaagaattg attggctcca attcttggag tggtgaatcc gttagcgagg    5160
tgccgccggc ttccattcag gtcgaggtgg cccggctcca tgcaccgcga cgcaacgcgg    5220
ggaggcagac aaggtatagg gcggcgccta caatccatgc caacccgttc catgtgctcg    5280
ccgaggcggc ataaatcgcc gtgacgatca gcggtccaat gatcgaagtt aggctggtaa    5340
gagccgcgag cgatccttga agctgtccct gatggtcgtc atctacctgc ctggacagca    5400
tggcctgcaa cgcgggcatc ccgatgccgc cggaagcgag aagaatcata tggggaagg    5460
ccatccagcc tcgcgtcgcg aacgccagca agacgtagcc cagcgcgtcg gccgccatgc    5520
cggcgataat ggcctgcttc tcgccgaaac gtttggtggc gggaccagtg acgaaggctt    5580
gagcgagggc gtgcaagatt ccgaataccg caagcgacag gccgatcatc gtcgcgctcc    5640
agcgaaagcg gtcctcgccg aaaatgaccc agagcgctgc cggcacctgt cctacgagtt    5700
gcatgataaa gaagacagtc ataagtgcgg cgacgatagt catgccccgc gcccaccgga    5760
aggagctgac tgggttgaag gctctcaagg gcatcggtcg agatcccggt gcctaatgag    5820
tgagctaact tacattaatt gcgttgcgct cactgcccgc tttccagtcg ggaaacctgt    5880
cgtgccagct gcattaatga atcggccaac gcgcggggag aggcggtttg cgtattgggc    5940
gccagggtgg ttttctttt caccagtgag acgggcaaca gctgattgcc cttcaccgcc    6000
tggccctgag agagttgcag caagcggtcc acgctggttt gccccagcag gcgaaaatcc    6060
tgtttgatgg tggttaacgg cgggatataa catgagctgt cttcggtatc gtcgtatccc    6120
actaccgaga tatccgcacc aacgcgcagc ccggactcgg taatggcgcg cattgcgccc    6180
agcgccatct gatcgttggc aaccagcatc gcagtgggaa cgatgccctc attcagcatt    6240
tgcatggttt gttgaaaacc ggacatggca ctccagtcgc cttcccgttc cgctatcggc    6300
tgaatttgat tgcgagtgag atatttatgc cagccagcca gacgcagacg cgccgagaca    6360
gaacttaatg ggcccgctaa cagcgcgatt tgctggtgac ccaatgcgac cagatgctcc    6420
acgcccagtc gcgtaccgtc ttcatgggag aaaataatac tgttgatggg tgtctggtca    6480
gagacatcaa gaaataacgc cggaacatta gtgcaggcag cttccacagc aatggcatcc    6540
tggtcatcca gcggatagtt aatgatcagc ccactgacgc gttgcgcgag aagattgtgc    6600
accgccgctt tacaggcttc gacgccgctt cgttctacca tcgacaccac cacgctggca    6660
cccagttgat cggcgcgaga tttaatcgcc gcgacaattt gcgacggcgc gtgcagggcc    6720
agactggagg tggcaacgcc aatcagcaac gactgtttgc ccgccagttg ttgtgccacg    6780
cggttgggaa tgtaattcag ctccgccatc gccgcttcca ctttttcccg cgttttcgca    6840
gaaacgtggc tggcctggtt caccacgcgg gaaacggtct gataagagac accggcatac    6900
tctgcgacat cgtataacgt tactggtttc acattcacca ccctgaattg actctcttcc    6960
gggcgctatc atgccatacc gcgaaaggtt ttgcgccatt cgatggtgtc cgggatctcg    7020
acgctctccc ttatgcgact cctgcattag gaagcagccc agtagtaggt tgaggccgtt    7080
gagcaccgcc gccgcaagga atggtgcatg caaggagatg gcgcccaaca gtcccccggc    7140
cacggggcct gccaccatac ccacgccgaa acaagcgctc atgagcccga agtggcgagc    7200
ccgatcttcc ccatcggtga tgtcggcgat ataggcgcca gcaaccgcac ctgtggcgcc    7260
ggtgatgccg gccacgatgc gtccggcgta gaggatcgag atctcgatcc cgcgaaatta    7320
a                                                                    7321
```